(12) United States Patent
Panoskaltsis-Mortari et al.

(10) Patent No.: US 11,781,101 B2
(45) Date of Patent: Oct. 10, 2023

(54) 3D-PRINTED MODELS OF BIOLOGICAL MICROENVIRONMENTS

(71) Applicant: Regents of the University of Minnesota, Minneapolis, MN (US)

(72) Inventors: Angela Panoskaltsis-Mortari, Woodbury, MN (US); Michael C. McAlpine, Minneapolis, MN (US); Fanben Meng, Saint Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 799 days.

(21) Appl. No.: 16/674,815

(22) Filed: Nov. 5, 2019

(65) Prior Publication Data
US 2020/0140801 A1 May 7, 2020

Related U.S. Application Data

(60) Provisional application No. 62/756,039, filed on Nov. 5, 2018.

(51) Int. Cl.
*B29C 64/00* (2017.01)
*C12M 1/12* (2006.01)
(Continued)

(52) U.S. Cl.
CPC .......... *C12M 25/14* (2013.01); *A61K 9/4825* (2013.01); *A61K 9/4833* (2013.01);
(Continued)

(58) Field of Classification Search
CPC .............................. C12M 25/14; B33Y 30/00
See application file for complete search history.

(56) References Cited

U.S. PATENT DOCUMENTS

2012/0226265 A1* 9/2012 Chiao ................. A61M 31/002
                                                          604/131
2018/0280578 A1* 10/2018 Hwang ............... A61L 27/3813
(Continued)

OTHER PUBLICATIONS

Cao et al., "Spatiotemporal control over growth factor signaling for therapeutic neovascularization," NIH Public Access, Advanced Drug Delivery Reivew, No. 59, No. 13, Nov. 10, 2007, pp. 1340-1350.
(Continued)

*Primary Examiner* — Nicholas R Krasnow
(74) *Attorney, Agent, or Firm* — Shumaker & Sieffert, P.A.

(57) ABSTRACT

A 3D-printed in vitro model biological microenvironment in examples discussed below may have one or more of the following features: (a) a gel matrix 3D-printed scaffold, wherein the gel matrix comprises a chemical composition configured to culture a first type of live cells, (b) a target chemical disposed at one or more locations within the gel matrix, the target chemical forming a chemical depot from which a chemical gradient is created within the gel matrix, (c) a conduit disposed within the gel matrix and defining a lumen comprising a second type of live cells, wherein the conduit is configured to enable at least some of the first type of live cells to migrate through the conduit and facilitate flow of at least: some of the live cells to an outlet of the conduit, or enable introduction of at least one of other cells, Achemical mediators, or drugs into the 3D-printed microenvironment.

26 Claims, 52 Drawing Sheets

(51) Int. Cl.
| | |
|---|---|
| C12N 5/00 | (2006.01) |
| A61K 9/48 | (2006.01) |
| B33Y 30/00 | (2015.01) |
| C12N 5/071 | (2010.01) |
| B33Y 99/00 | (2015.01) |
| B22F 12/00 | (2021.01) |
| B29C 64/255 | (2017.01) |
| B29C 64/386 | (2017.01) |
| B33Y 40/00 | (2020.01) |
| B22F 12/82 | (2021.01) |
| B29C 64/40 | (2017.01) |
| B29C 64/182 | (2017.01) |
| B33Y 50/02 | (2015.01) |
| B29C 64/20 | (2017.01) |
| B29C 64/227 | (2017.01) |
| B33Y 40/10 | (2020.01) |
| B29C 64/25 | (2017.01) |
| B22F 10/85 | (2021.01) |
| B29C 64/205 | (2017.01) |
| B29C 64/393 | (2017.01) |
| B29C 64/10 | (2017.01) |
| B33Y 50/00 | (2015.01) |
| B29C 64/30 | (2017.01) |
| B29C 64/245 | (2017.01) |
| B29C 64/176 | (2017.01) |
| B29C 64/307 | (2017.01) |
| B33Y 40/20 | (2020.01) |
| B33Y 10/00 | (2015.01) |
| B22F 10/00 | (2021.01) |
| G01N 33/483 | (2006.01) |
| B33Y 80/00 | (2015.01) |
| B33Y 70/00 | (2020.01) |

(52) U.S. Cl.
CPC ............ *A61K 9/4866* (2013.01); *B22F 10/00* (2021.01); *B22F 10/85* (2021.01); *B22F 12/00* (2021.01); *B22F 12/82* (2021.01); *B29C 64/00* (2017.08); *B29C 64/10* (2017.08); *B29C 64/176* (2017.08); *B29C 64/182* (2017.08); *B29C 64/20* (2017.08); *B29C 64/205* (2017.08); *B29C 64/227* (2017.08); *B29C 64/245* (2017.08); *B29C 64/25* (2017.08); *B29C 64/255* (2017.08); *B29C 64/30* (2017.08); *B29C 64/307* (2017.08); *B29C 64/386* (2017.08); *B29C 64/393* (2017.08); *B29C 64/40* (2017.08); *B33Y 10/00* (2014.12); *B33Y 30/00* (2014.12); *B33Y 40/00* (2014.12); *B33Y 40/10* (2020.01); *B33Y 40/20* (2020.01); *B33Y 50/00* (2014.12); *B33Y 50/02* (2014.12); *B33Y 99/00* (2014.12); *C12N 5/0068* (2013.01); *C12N 5/0691* (2013.01); *B33Y 70/00* (2014.12); *B33Y 80/00* (2014.12); *G01N 33/4833* (2013.01)

(56) References Cited

U.S. PATENT DOCUMENTS

| | | | | |
|---|---|---|---|---|
| 2019/0185818 | A1* | 6/2019 | Sikora | G01N 33/5088 |
| 2019/0345439 | A1* | 11/2019 | Skardal | G01N 33/502 |

OTHER PUBLICATIONS

Meng et al., "4D Engineered in vitro Metastatic Models via Guided Cell Migration," Department of Mechanical Engineering, University of Minnesota, MRS Spring Meeting at Phoenix, Apr. 5, 2018, 17 pp.

Debnath et al., "Modelling Glandular Epithelial Cancers in Three-Dimensional Cultures," Nature Publishing Group, Nature Reivews | Cancer, vol. 5, Sep. 2005, pp. 675-687.

Zhang et al., "Biodegradable scaffold with built-in vasculature for organ-on-a-chip engineering and direct surgical anastomosis," PMC, HHS Public Access, Nature Materials, vol. 15, No. 6, Mar. 7, 2016, pp. 669-678.

Gorden et al., "Identification of Three Molecular and Functional Subtypes in Canine Hemangiosarcoma through Gene Expression Profiling and Progenitor Cell Characterization," Elsevier, The American Journal of Pathology, vol. 184, No. 4, Apr. 2014, pp. 985-995.

Kim et al. "Interleukin-8 Promotes Canine Hemangiosarcoma Growth by Regulating the Tumor Microenvironment," NIH Public Access, Experimental Cell Research, vol. 323, No. 1, Apr. 15, 2014, pp. 155-164.

Li et al., "4D bioprinting: the next-generation technology for biofabrication enabled by stimuli-responsive materials," IOP Publishing, Biofabrication, vol. 9, Dec. 1, 2016, 17 pp.

Scott et al., "Heterotypic mouse models of canine osteosarcoma recapitulate tumor heterogeneity and biological behavior," The Company of Biologists, Disease Models & Mechanisms, vol. 9, Sep. 23, 2016, pp. 1435-1444.

Scott et al., "Molecular subtypes of osteosarcoma identified by reducing tumor heterogeneity through an interspecies comparative approach," PMC, HHS Public Access, Bone, vol. 43, No. 3, Sep. 2011, pp. 356-367.

Sugiyama et al., "Maintenance of the Hematopoietic Stem Cell Pool by CXCL12-CXCR4 Chemokine Signaling in Bone Marrow Stromal Cell Niches," ScienceDirect, Immunity, vol. 25, Issue 6, Dec. 2006, pp. 977-988.

Im et al., "Interactions between CXCR4 and CXCL12 promote cell migration and invasion of canine hemangiosarcoma," HHS Public Access, Veterinary and Comparative Oncology, vol. 15, No. 2, Jun. 2017, pp. 315-327.

Alemany-Ribes et al., "Bioengineering 3D environments for cancer models," Elsevier, Advanced Drug Delivery Reviews, vol. 79-80, Jul. 1, 2014, pp. 40-49.

Zhang et al., "Bioprinting the Cancer Microenvironment," HHS Public Access, ACS Biomaterials Science & Engineering, vol. 2, No. 10, Oct. 10, 2016, pp. 1710-1721.

Zanoni et al., "3D tumor spheroid models for in vitro therapeutic screening: a systemic approach to enhance the biological relevance of data obtained," PMC, Scientific Reports, vol. 6, Jan. 11, 2016.

McCracken et al., "Programming Mechanical and Physiochemical Properties of 3D Hydrogel Cellular Microcultures via Direct Ink Writing," Wiley, Advanced Healthcare Materials, vol. 5, Issue 9, Feb. 29, 2016, pp. 1025-1039.

Kolesky et al., "3D Bioprinting of Vascularized, Heterogeneous Cell-Laden Tissue Contstructs," Advanced Materials, vol. 26, Issue 19, Feb. 18, 2017, pp. 3124-3130.

Lee et al., "Hydrogels for Tissue Engineering," The American Chemical Society, Chemical Reviews, vol. 101, No. 7, Jul. 2001, 1869-1880.

Liu et al., "Carcinoma-associated fibroblasts promoted tumor spheroid invasion on a microfluidic 3D co-culture device," The Royal Society of Chemistry, Lab Chip, vol. 10, Apr. 23, 2010, 1671-1677.

Du et al., "Microfluidic system for modelling 3D tumour invasion into surround stroma and drug screening," IOP Publishing, Biofabrication, vol. 10, No. 3, Jun. 6, 2018, 14 pp.

Zhao et al., "Three-dimensional printing of Hela cells for cervical tumor model in vitro," IOP Publishing, Biofabrication, vol. 6, No. 3, Apr. 11, 2014, 11 pp.

Pang et al., "TGF-β induced epithelial-mesenchymal transition in an advanced cervical tumor model by 3D printing," IOP Publishing, Biofabrication, vol. 10, No. 4, Sep. 10, 2018, 13 pp.

Griffith et al., "Capturing complex 3D tissue physiology in vitro," Nature Publishing Group, Nature Reviews, Molecular Cell Biology, vol. 7, Mar. 2006, pp. 211-223.

(56) References Cited

OTHER PUBLICATIONS

Hakanson et al., "Engineered 3D environments to elucidate the effect of environmental parameters on drug response in cancer," RSC Publishing, The Royal Society of Chemistry, Integrative Biology, vol. 3, No. 1, Oct. 7, 2010, pp. 31-38.
Horning et al., "3-D Tumor Model for In Vitro Evaluation of Anticancer Drugs," The American Chemical Society, Molecular Pharmaceutics, vol. 5, No. 5, Jun. 3, 2009, pp. 849-862.
Reymond et al., "Crossing the endothelial barrier during metastasis," Macmillan Publishers Limited, Nature Reviews | Cancer, vol. 13, Dec. 2013, pp. 858-870.
Chaffer et al., "A Perspective on Cancer Cell Metastasis," Science Mag, Science, vol. 331, Mar. 25, 2011, pp. 1559-1564.
Joung et al., "3D Printed Stem-Cell Derived Neural Progenitors Generate Spinal Cord Scaffolds," Wiley, Advanced Functional Materials, vol. 28, Issue 39, Sep. 26, 2018, 10 pp.
Kang et al., "A 3D bioprinting system to produce human-scale tissue constructs with structural integrity," Nature Biotechnology, vol. 34, No. 3, Mar. 2016, pp. 312-319.
Arwert et al., "Epithelial stem cells, wound healing and cancer," Macmillan Publishers Limited, Nature Reviews | Cancer, vol. 12, Mar. 2012, pp. 170-180.
Seliktar,"Designing Cell-Compatible Hydrogels for Biomedical Applications," Science Mag, Science, vol. 336, Jun. 1, 2012, pp. 1124-1128.
Condeelis et al., "Intravital Imagine of Cell Movement in Tumours," Nature Reviews | Cancer, vol. 3, Dec. 2003, pp. 921-930.
Zhu et al., "Stabilization of proteins encapsulated in injectable poly (lactide-co-glycolide)," Nature America Inc., Nature Biotechnology, vol. 18, Sep. 22, 1999, pp. 52-57.
Kinstlinger et al., "3D-printed fluidic networks as vasculature for engineered tissue," Royal Society of Chemistry, Lab on a Chip, vol. 16, May 3, 2016, pp. 2025-2043.
Gao et al., "4D Bioprinting for Biomedical Applications," CellPress, Trends in Biotechnology, TIBTEC, 1367, vol. 34, Issue 9, Sep. 2016, pp. 746-756.
Scott et al., "Comparative transcriptome analysis quantifies immune cell transcript levels, metastatic progression and survival in osteosarcoma," HHS Public Access, Cancer Search, vol. 78, Issue 2, Jan. 15, 2018, pp. 326-337.
Jo et al., "WHO Classification of Soft Tissue Tumours: An Update Based on the 2013 (4th) Edition," Abstract only, PubMed, NIH, National Library of Medicine, Pathology, vol. 46, No. 2, Feb. 2014, pp. 95-104.
Gupta et al., "3D Printed Programmable Release Capsules," ACS Publications, American Chemical Society, Nano Letters, vol. 15, Jun. 4, 2015, 9 pp.
Gupta et al., "3D Printed Programmable Release Capsules," ACS Publications, American Chemical Society, Nano Letters, vol. 15, Jun. 5, 2015, pp. 5321-5329.
Meng et al., "3D Bioprinted In Vitro Metastatic Models via Reconstruction of tumor Microenvironments," Advanced Materials, vol. 31, Issue 10, Mar. 8, 2019, 10 pp.
Vanderburgh et al., "3D Printing of Tissue Engineered Constructs for In Vitro Modeling of Disease Progression and Drug Screening," HHS Public Access, Annals of Biomedical Engineering, vol. 45, Issue 1, Jan. 2017, pp. 164-179.
Pampaloni et al., "The third dimension bridges the gap between cell culture and live tissue," ResearchGate, Advance Online Publication, Nature Publishing Group, Nature Reviews Molecular Cell Biology, Aug. 8, 2007.
Bian et al., "Genetically engineered cerebral organoids model brain tumor formation," Europe PMC Funders Group, Europe PubMed Central, Nature Methods, vol. 15, Issue 9, Sep. 2018, 24 pp.
Fischbach et al., "Engineering tumors with 3D scaffolds," Nature Methods, vol. 4, No. 10, Oct. 2007, pp. 855-860.
Rijal et al., "A versatile 3D tissue matrix scaffold system for tumor modeling and drug screening," PMC, AAAS, Science Advances, vol. 7, Issue 9, Sep. 2017.

Lee et al., "Three-dimensional Culture Models of Normal and Malignant Breast Epithelial Cells," PubMed, PMC, Nature Methods, vol. 4, Issue 4, Apr. 2007, pp. 359-365.
Todhunter et al., "Programmed synthesis of 3D tissues," HHS Public Access, PMC, Nature Methods, vol. 12, No. 10, Oct. 2015, pp. 975-981.
Kalluri et al., "Fibroblasts in cancer," Nature Publishing Group, Nature Reviews | Cancer, vol. 6, May 2006, pp. 392-401.
Joyce et al., "Microenvironmental regulation of metastasis," PMC, NIH Public Access, Nature Reviews | Cancer, vol. 9, Issue 4, Apr. 2009, pp. 239-252.
Roussos et al., "Chemotaxis in cancer," PubMed, NIH Public Access, Nature Reviews | Cancer, vol. 11, Issue 8, Aug. 2011, pp. 573-587.
Murphy et al., "3D Bioprinting of Tissues and Organs," ResearchGate, Nature Biotechnology, vol. 32, No. 8, Aug. 2014, pp. 773-785.
Mannoor et al., "3D Printed Bionic Ears," HIB Public Access, Nano Letters, vol. 13, Issue 6, Jun. 12, 2013, pp. 2634-2639.
Kolesky et al., "Three-dimensional bioprinting of thick vascularized tissues," PMC, PNAS, Proceedings of the National Academy of Sciences of the United States of America, vol. 113, Issue 12, Mar. 22, 2016, pp. 3179-3184.
Cui et al., "3D Bioprinting for Organ Regeneration," PubMed, PMC, HHS Public Access, Advanced Healthcare Materials, vol. 6, Issue 1, Jan. 2017, 54 pp.
Villar et al., "A Tissue-Like Printed Material," NIH Public Access, Science, vol. 340, Issue 6128, Apr. 5, 2013, pp. 48-52.
Pati et al., "Printing three-dimensional tissue analogues with decellularized extracellular matrix bioink," Macmillan Publishers Limited, Nature Communications, vol. 5, No. 3935, Jun. 2, 2014, 11 pp.
Colosi et al., "Microfluidic Bioprinting of Heterogeneous 3D Tissue Constructs Using Low-Viscosity Bioink," PubMed, PMC, HHS Public Access, Advanced Materials, vol. 28, Issue 4, Jan. 27, 2016, pp. 677-684.
Miller et al., "Rapid casting of patterned vascular networks for perfusable engineered 3D tissues," PMC, HHS Public Access, Nature Materials, vol. 11, Issue 9, Sep. 2012, pp. 768-774.
Johnson et al., "3D Printed Anatomical Nerve Regeneration Pathways," PMC, HHS Public Access, Advanced Functional Materials, vol. 25, No. 39, Oct. 21, 2015, pp. 6205-6217.
Gupta et al., "3D Printed Programmable Release Capsules," HHS Public Access, Nano Letters, vol. 15, No. 8, Aug. 12, 2015 pp. 5321-5329.
Moroni et al., "Biofabrication strategies for 3D in vitro models and regenerative medicine," PMC, HHS Public Access, Nature Review Materials, vol. 3, No. 5, May 2018, pp. 21-37.
Bost et al., "The JUN Kinase/Stress-activated Protein Kinase Pathway Is Required for Epidermal Growth Factor Stimulation of Growth of Human A549 Lung Carcinoma Cells," The American Society for Biochemistry and Molecular Biology, Inc., The Journal of Biological Chemistry, vol. 272, No. 52, Dec. 26, 1997, pp. 33422-33429.
Cristofanilli et al., "Angiogenesis Modulation in Cancer Research: Novel Clinical Approaches," Nature Publishing Group, Nature Reviews, Drug Discovery, vol. 1, Jun. 2002, pp. 415-426.
Shamloo et al., "Mechanisms of Vascular Endothelial Growth Factor-Induced Pathfinding by Endothelial Sprouts in Biomaterials," PMC, Tissue Engineering Part A, vol. 18, No. 3-4, Feb. 2012, pp. 320-330.
Stish et al., "Design and modification of EGF4KDEL 7Mut, a novel bispecific ligand-directed toxin, with decreased immunogenicity and potent anti-mesothelioma activity," PMC, British Journal of Cancer, vol. 101, No. 7, Oct. 6, 2009, pp. 1114-1123.
Oh et al., "A novel 'reduced immunogenicity' bispecific targeted toxin simultaneously recognizing human EGF and IL-4 receptors in a mouse model of metastatic breast carcinoma," PMC, HHS Public Access, Clinical Cancer Research, vol. 15, No. 19, Oct. 1, 2009, pp. 6137-6147.
Vallera et al., "Bioengineering a unique deimmunized bispecific targeted toxin that simultaneously recognizes human CD22 and CD 19 receptors in a mouse model of B cell metastases," PMC, HHS Public Access, Molecular Cancer Therapeutics, vol. 9, No. 6, Jun. 2010, pp. 1872-1883.

(56) References Cited

OTHER PUBLICATIONS

Hutchinson et al., "High drug attrition rates—where are we going wrong?," Macmillan Publishers Limited, Nature Reviews, Clinical Oncology, vol. 8, Apr. 2011, pp. 189-190.
Nichol et al., "Cell-laden microengineered gelatin methacrylate hydorgels," PMC, HHS Public Access, Biomaterials, vol. 3, No. 21, Jul. 2010, pp. 5536 5544.
Mura et al., "Stimuli-responsive nanocarriers for drug delivery," ResearchGate, Nature Materials, vol. 12, Nov. 2013, pp. 991-1003.
Wong et al., "Artificial lymphatic drainage systems for vascularized microfluidic scaffolds," Wiley Periodicals, Inc., Society for Biomaterials, Dec. 24, 2012, pp. 2181-2190.
Tian et al., "Organ-specific Metastases Obtained by Culturing Colorectal Cancer Cells on Tissue-Specific Decelluarized Scaffolds," PMC, HHS Public Access, National Biomedical Engineering, vol. 2, Oct. 23, 2018, pp. 443-452.
Jeong et al., "Co-Culture of Tumor Spheroids and Fibrobblasts in a Collagen Matrix-Incorporated Microfluidic Chip Mimics Reciprocal Activation in Solid Tumor Microenvironment," PMC, PLoS One, vol. 11, No. 7, Jul. 8, 2016, 17 pp.
Jaganathan et al., "Three-Dimensional In Vitro Co-Culture Model of Breast Tumor using Magnetic Levitation," PMC, Nature Research Scientific Reports, vol. 4, Oct. 1, 2014, 9 pp.
Jeon et al., "Human 3D vascularized organotypic microfluidic assays to study breast cancer cell extravasation," PMC, Proceedings of the National Academy of Sciences of the United States of America, PNAS, vol. 112, No. 1, Jan. 6, 2015, pp. 214-219.
Chen et al., "On-chip human microvasculature assay for visualization and quantitation of tumor cell extravasation dynamics," PMC, HHS Public Access, Nature Protocols, vol. 12, No. 5, May 2017, pp. 865-880.
Zervantonakis et al., "Three-dimensional microfluidic model for tumor cell intravasation and endothelial barrier function," Proceedings of the National Academy of Sciences of the United States of America, PNAS, vol. 109, No. 34, Aug. 21, 2012, pp. 13515-13520.
Infanger et al., "Engineered Culture Models for Studies of Tumor-Microenvironment Interactions," PubMed, Annual Review of Biomedical Engineering, vol. 15, Apr. 29, 2013, pp. 29-53.
Liu et al., "Rapid Continuous Multi-Material Extrusion Bioprinting," PMC, HHS Public Access, Advanced Materials, vol. 29, No. 3, Jan. 2017, 18 pp.
Miri et al., "Microfluidics-Enabled Multi-Material Maskless Stereolithographic Bioprinting," PMC, HHS Public Access, Advanced Materials, vol. 30, No. 27, Jul. 2018, 16 pp.
Pi et al., "Digitally Tunable Microfluidic Bioprinting of Multilayered Cannular Tissues," PMC, HHS Public Access, Advanced Materials, vol. 30, No. 43, Oct. 2018, 18 pp.
Larue et al., "Epithelial-mesenchymal transition in development and cancer: Role of phosphatidylinositol 3'kinase/AKT pathways," ResearchGate, Nature Publishing Group, Oncogene, vol. 24, Dec. 2005, pp. 7443 7454.
Nieman et al., "N-Cadherin Promotes Mobility in Human Breast Cancer Cells Regardless of Their E-Cadherin Expression," JCB, Journal of Cell Biology, vol. 147, No. 3, Nov. 1, 1999, pp. 631-644.
Shintani et al., "Epithelial to Mesenchymal Transition Is a Determinant of Sensitivity to Chemoradiotherapy in Non-Small Cell Lung Cancer," The Annals of Thoracic Surgery, vol. 92, Issue 5, Nov. 1, 2011, pp. 1794-1804.
Seo et al., "In vitro models of tumor vessels and matrix: Engineering approaches to investigate transport limitations and drug delivery in cancer," PMC, HHS Public Access, Advanced Drug Delivery Reviews, vol. 69-70, Apr. 20, 2014, pp. 205-216.
Meng et al., "4D Engineering in vitro Metastatic Models via Guided Cell Migration," Department of Mechanical Engineering & Department of Pediatrics and Medicine, UMN, IEM Annual Conference and Retreat at UMN Campus, Nov. 6, 2017, 1 pp.
Roussos et al., "Mena invasive (MenaINV) promotes multicellular streaming mobility and transendothelial migration in a mouse model of breast cancer," Journal of Cell Science, vol. 124, Feb. 18, 2011, pp. 2120-2131.
Lutolf et al., "Synthetic biomaterials as instructive extracellular microenvironments for morphogenesis in tissue engineering," Nature Biotechnology, vol. 23, No. 1, Jan. 2002, pp. 47-55.

\* cited by examiner

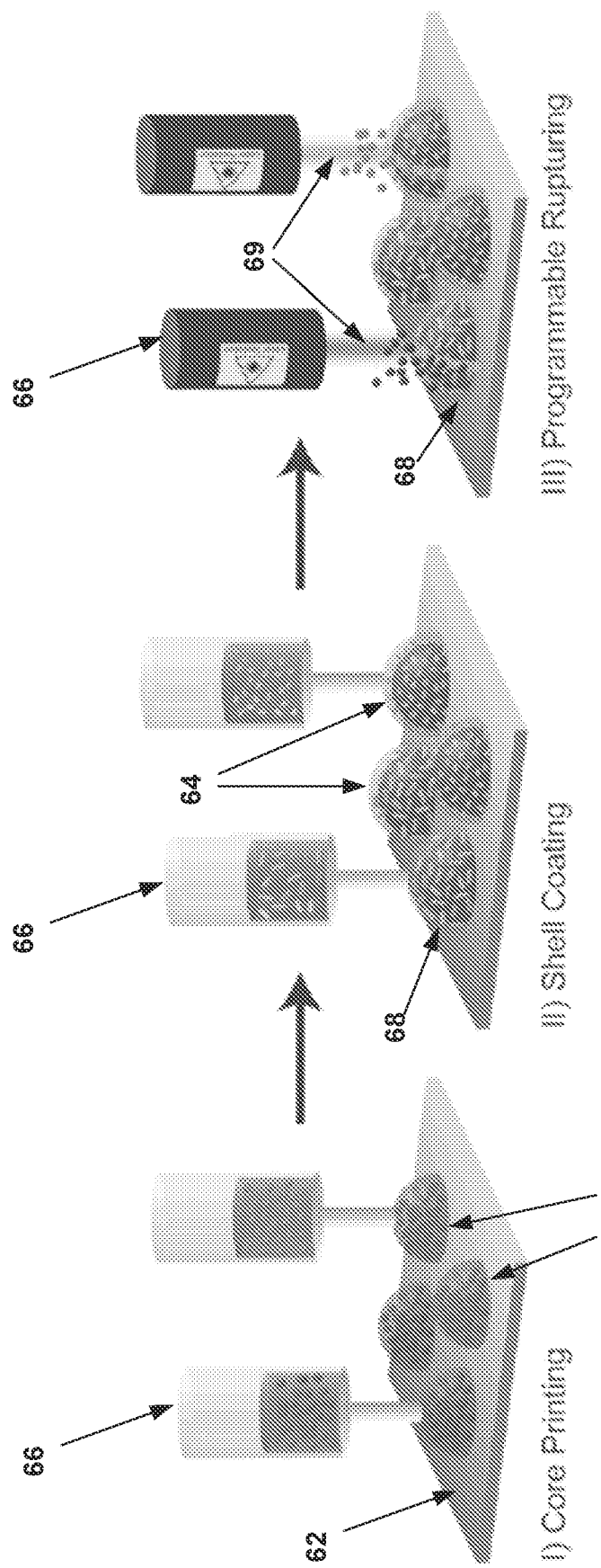

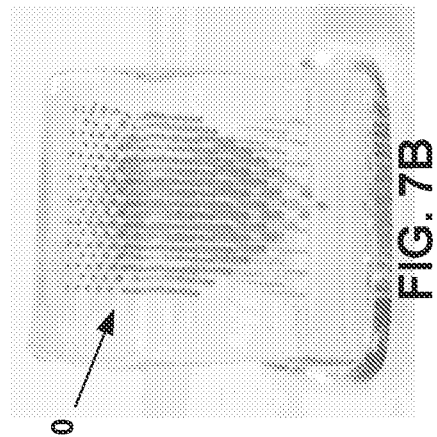
FIG. 7B
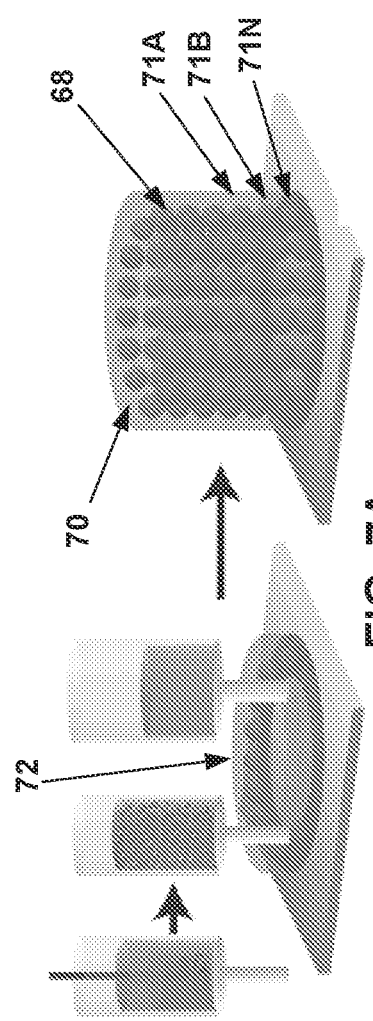
FIG. 7A
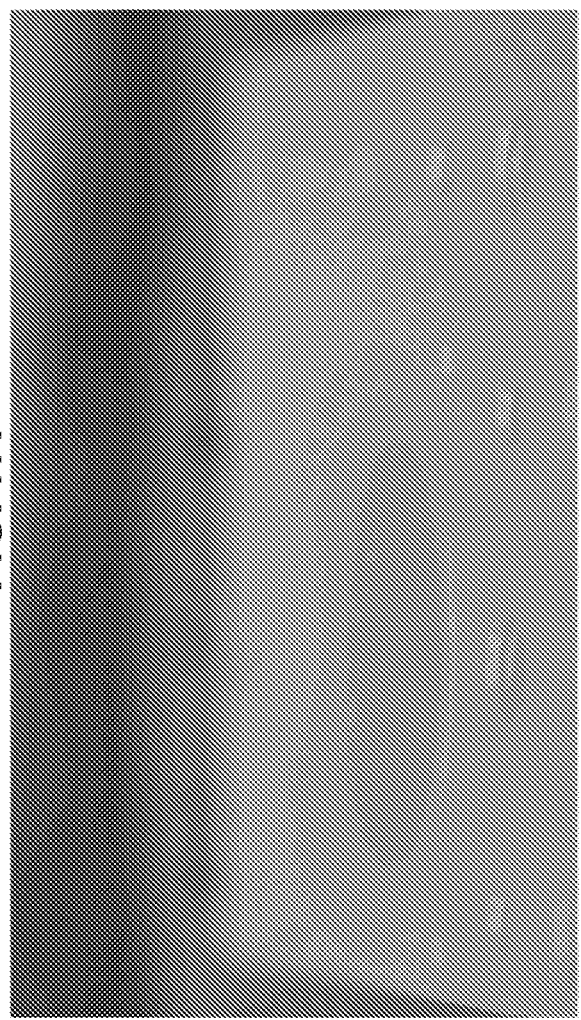
FIG. 7C
Complex Multiple Capsule Arrays
FIG. 7D

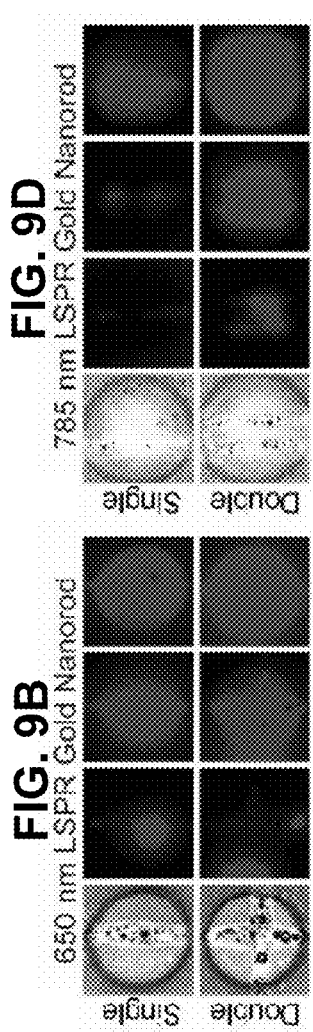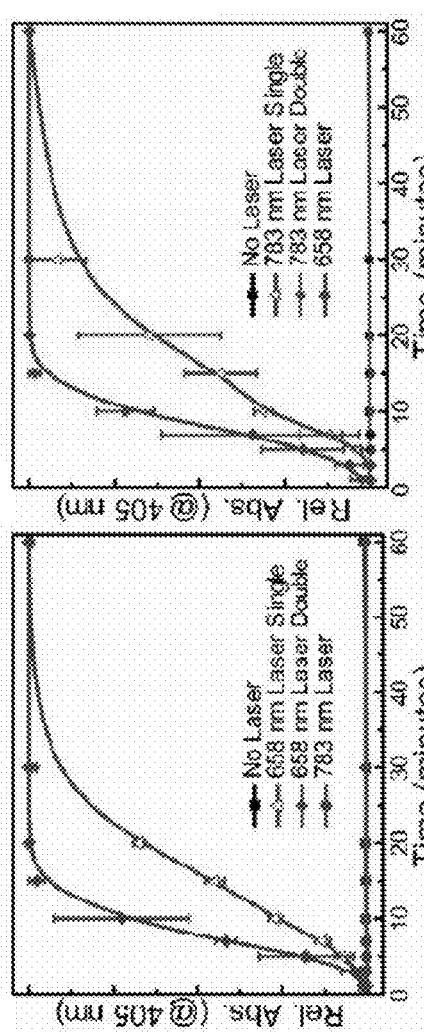
FIG. 9D
FIG. 9E
FIG. 9B
FIG. 9C
FIG. 9A

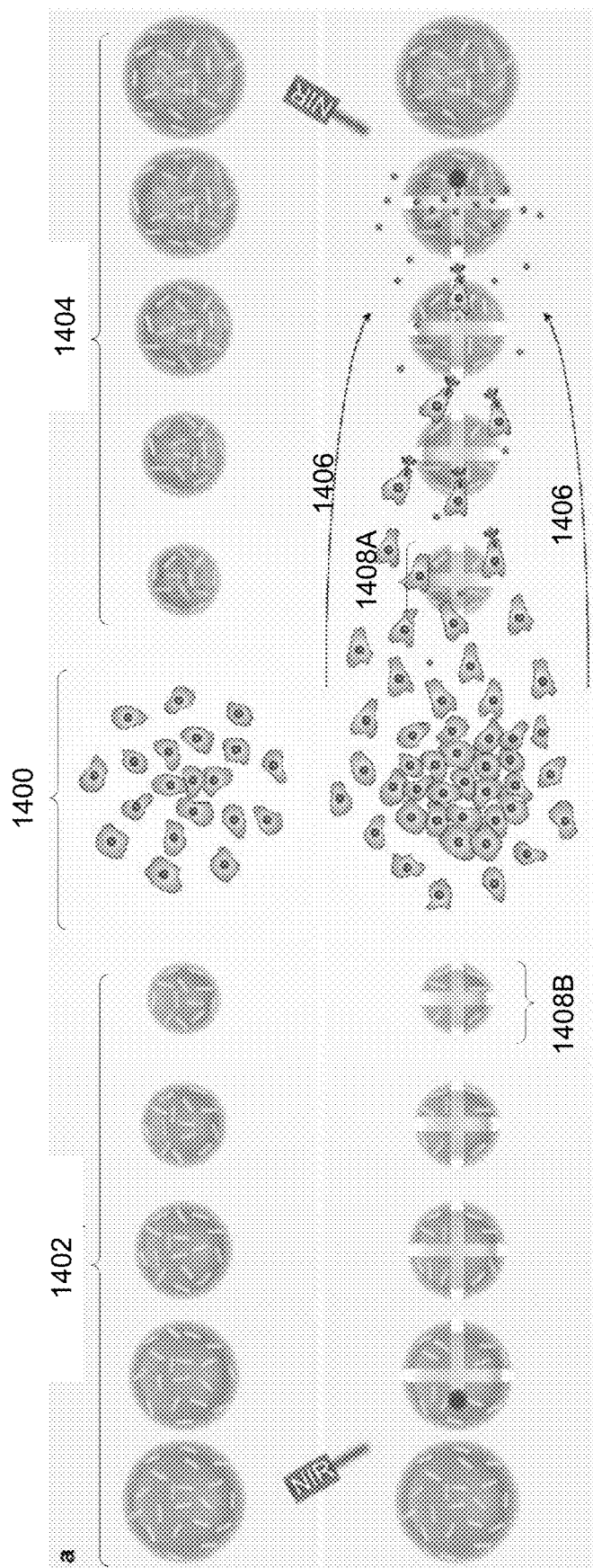

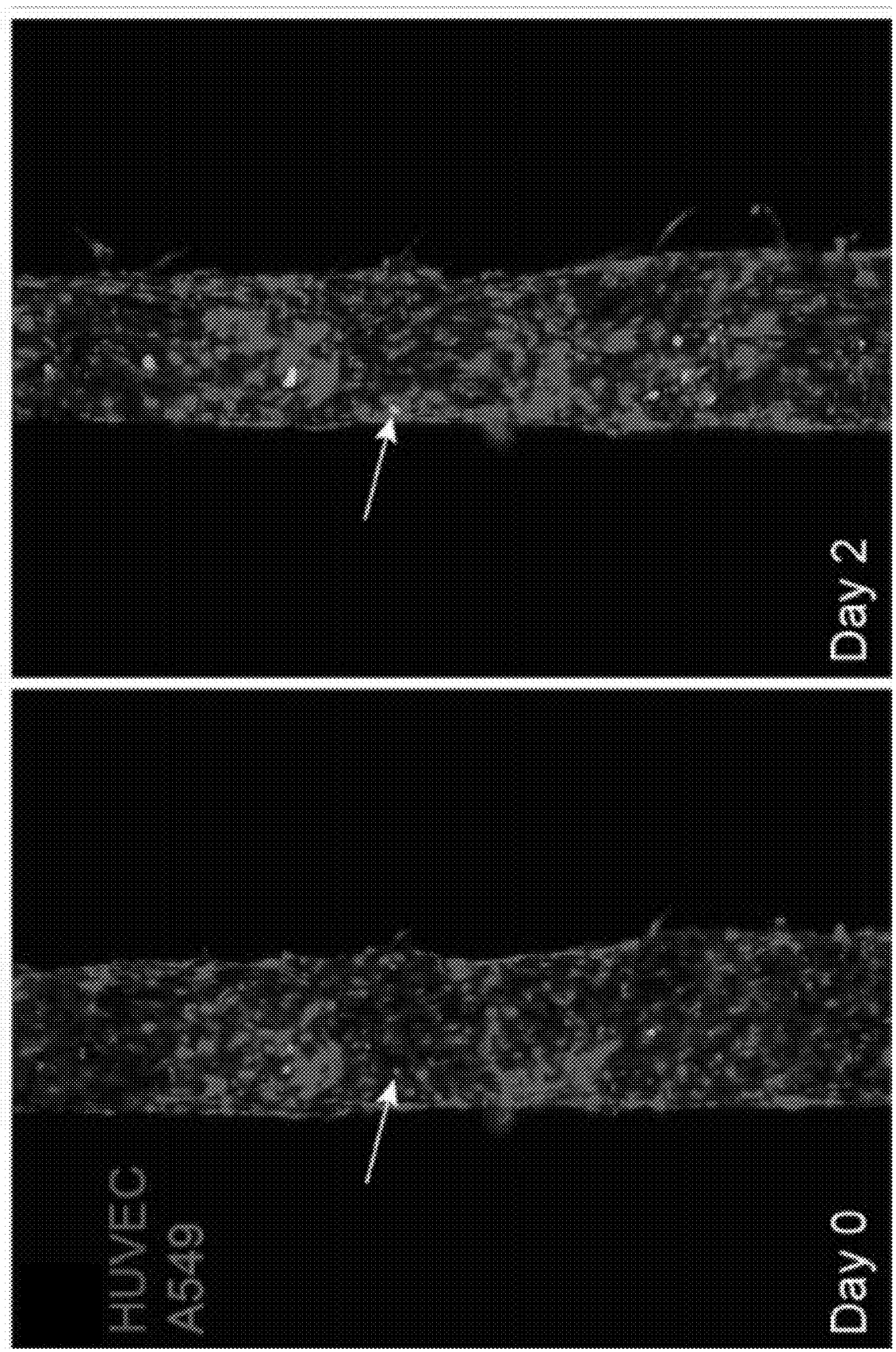

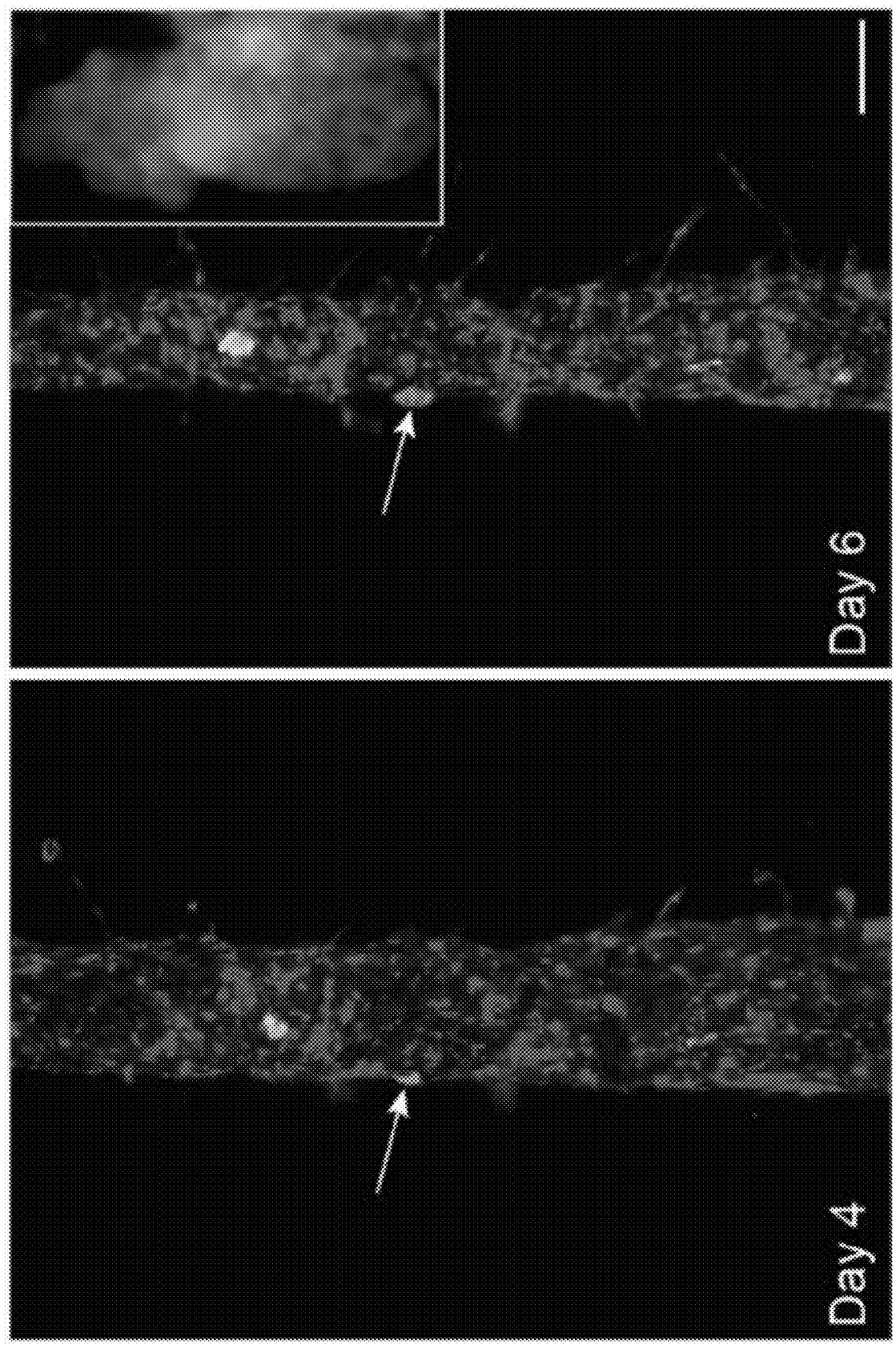

Metastasis + Proliferation

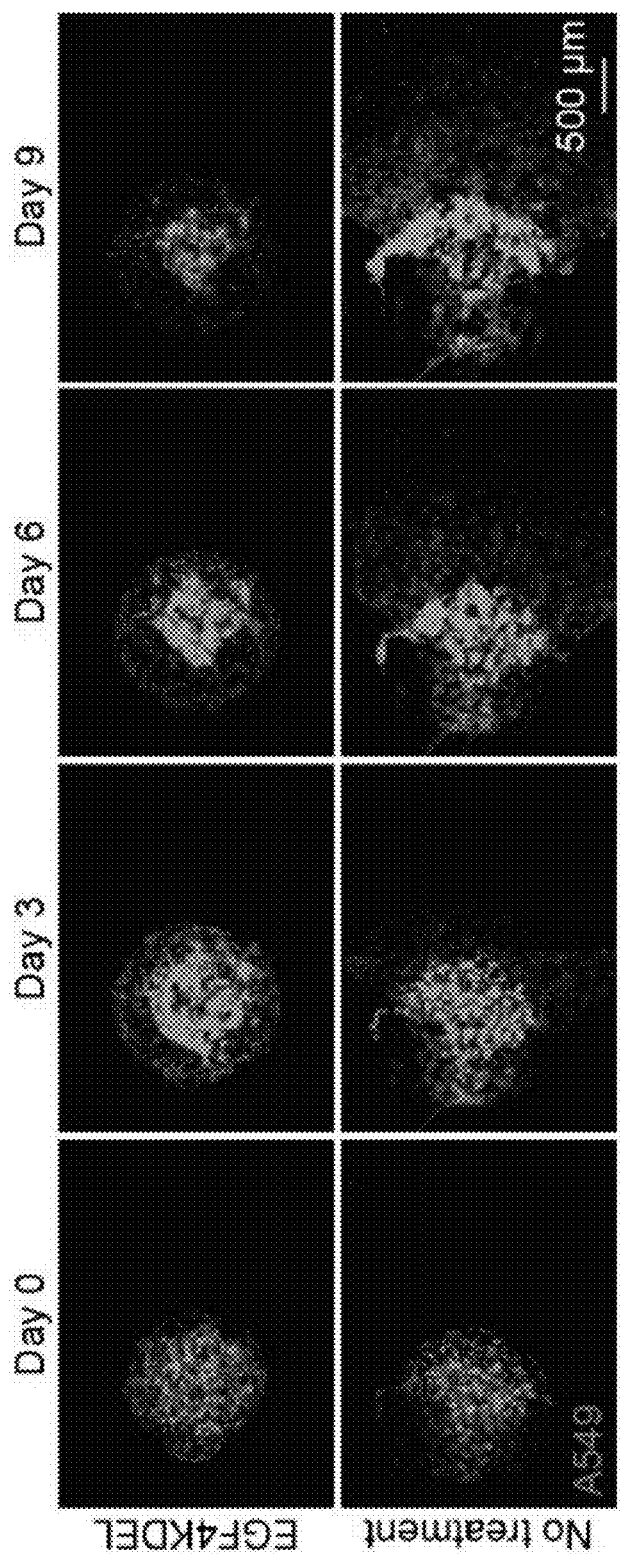
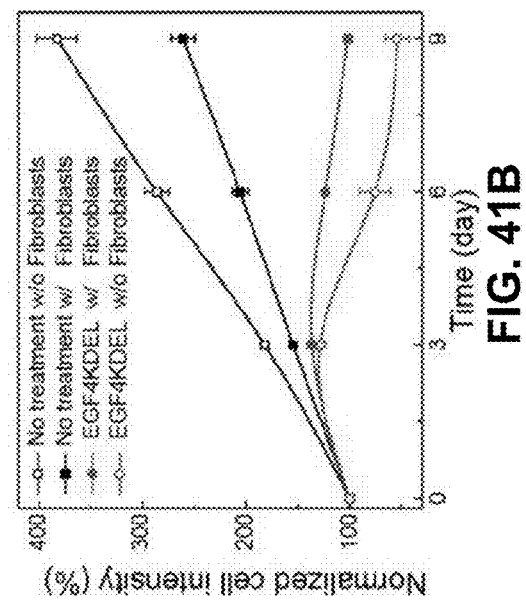
FIG. 41A
FIG. 41B

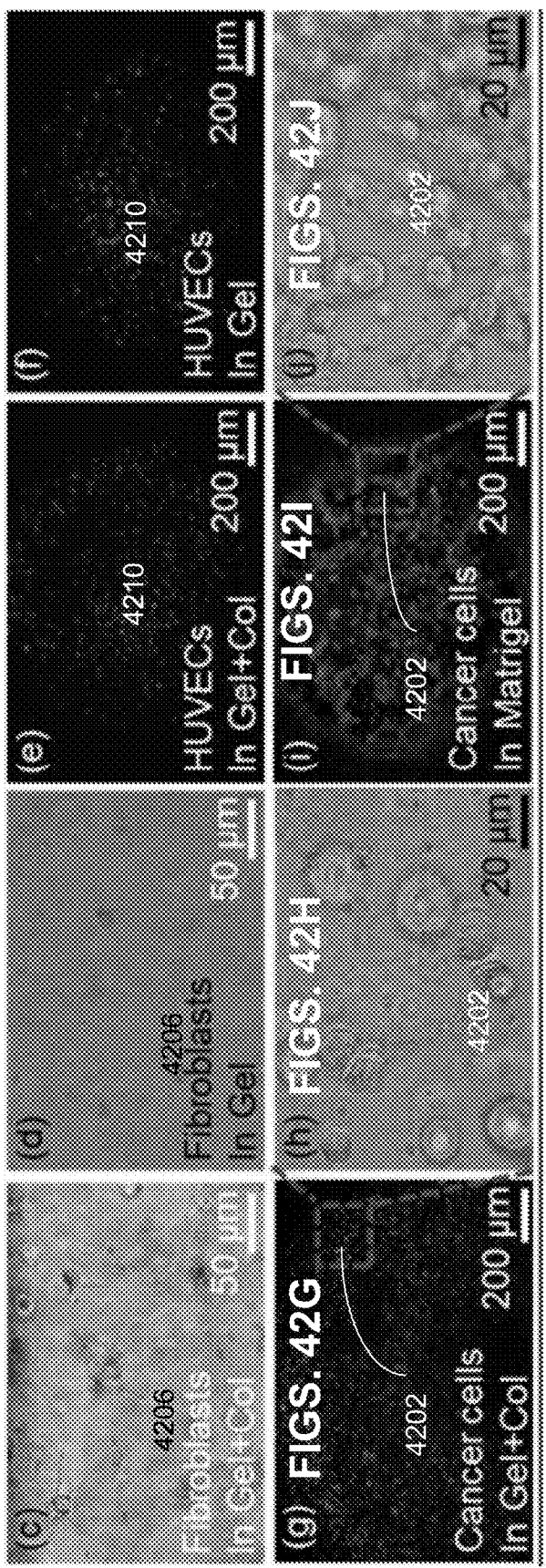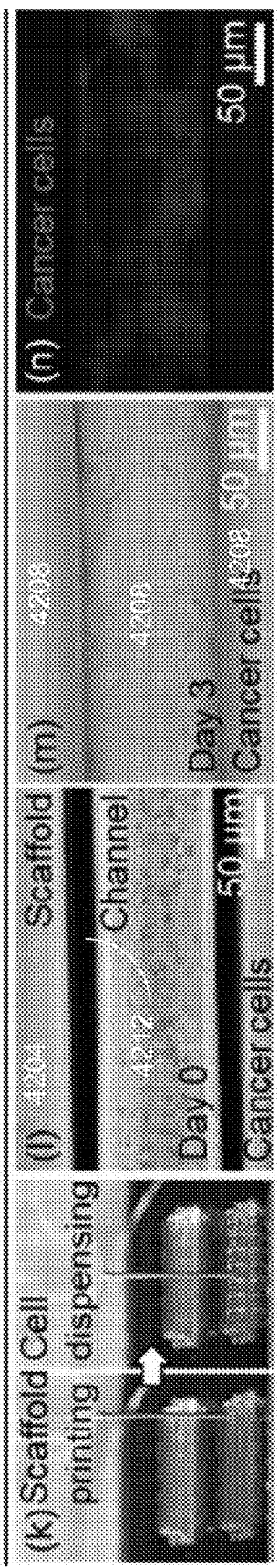

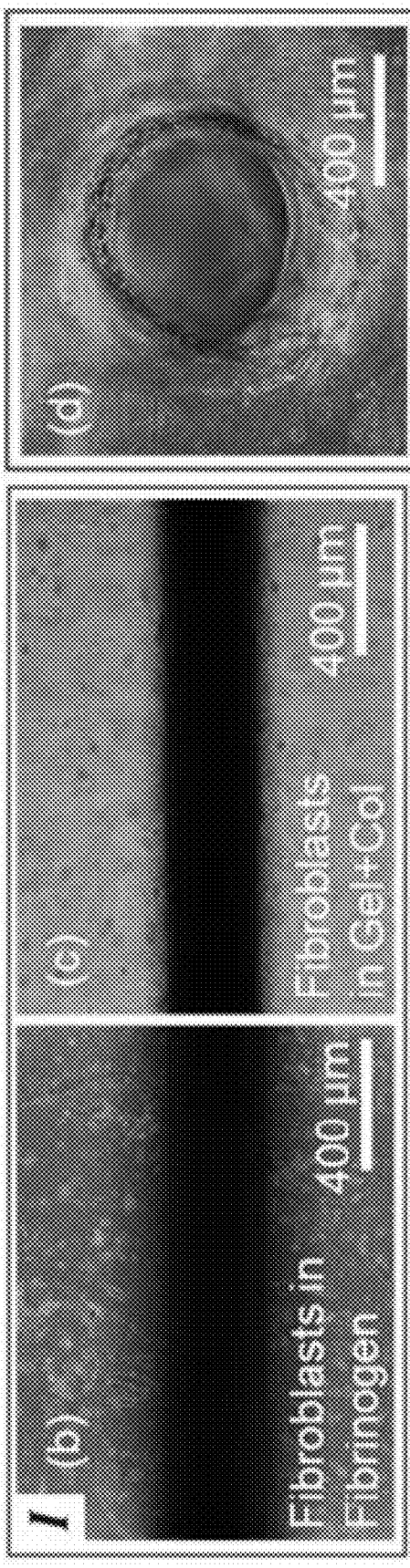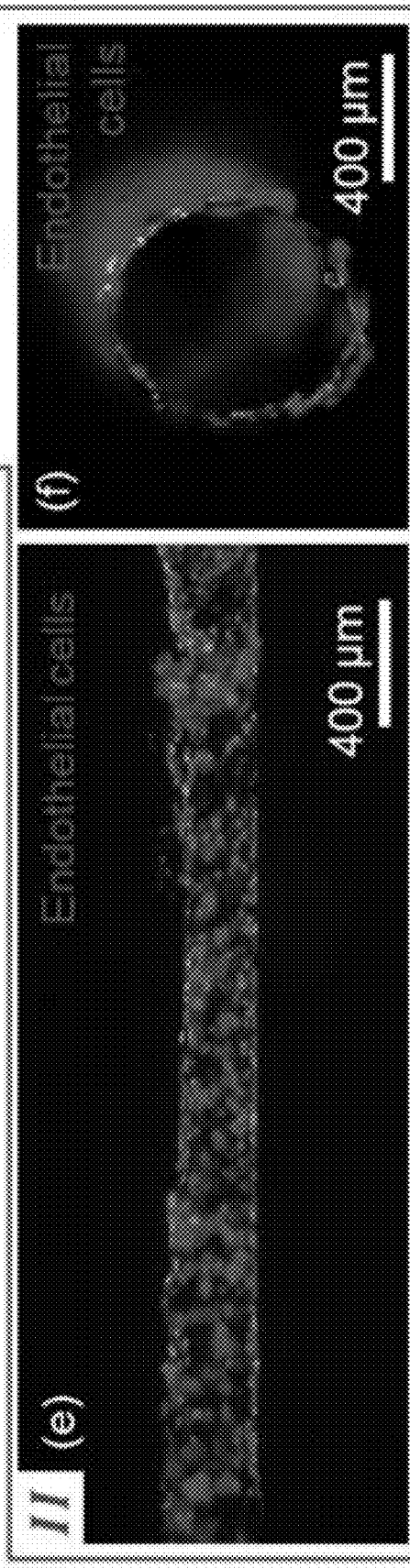

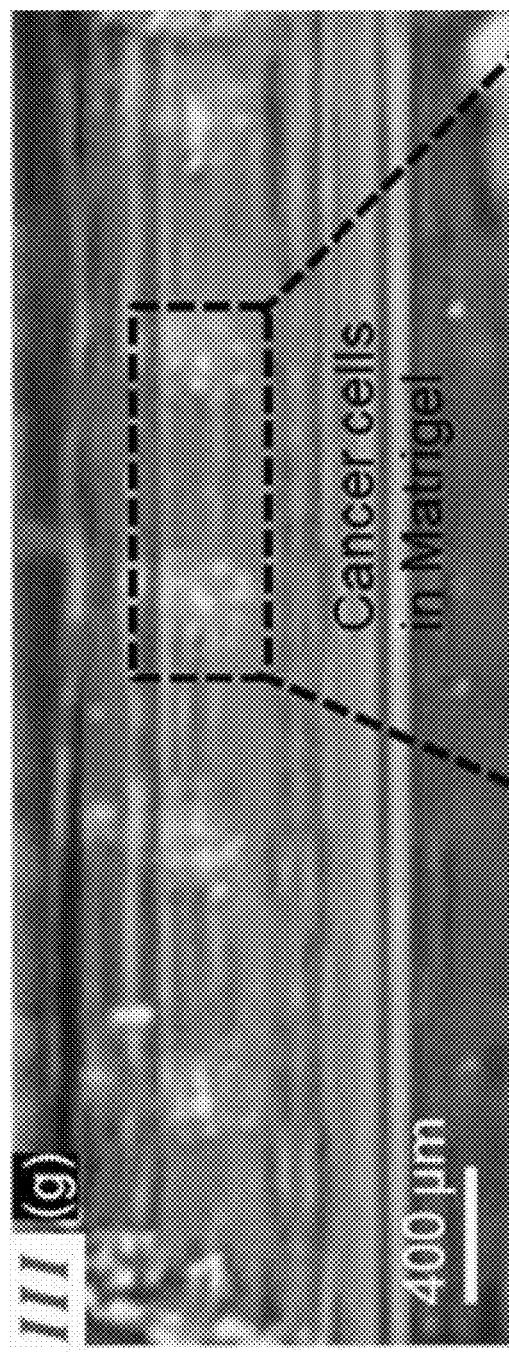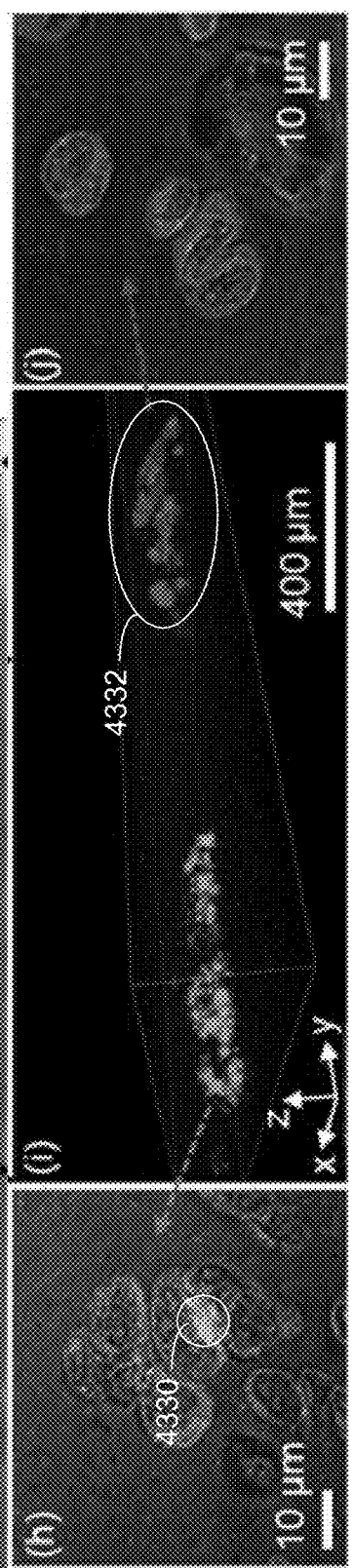
FIGS. 43G    FIGS. 43H    FIGS. 43I    FIGS. 43J

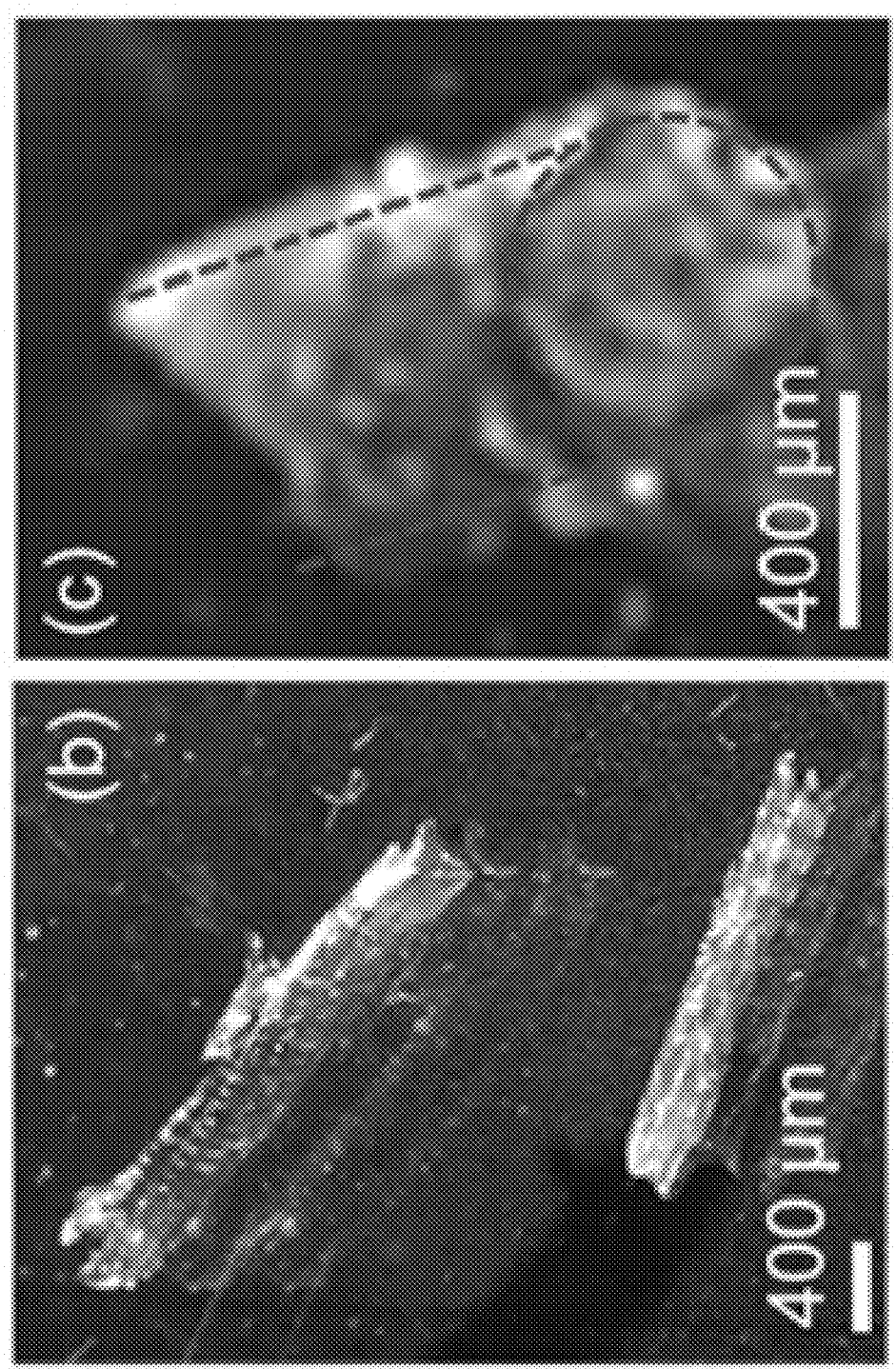

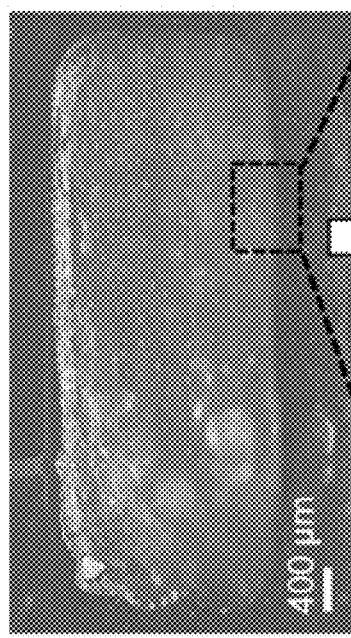
FIG. 44D
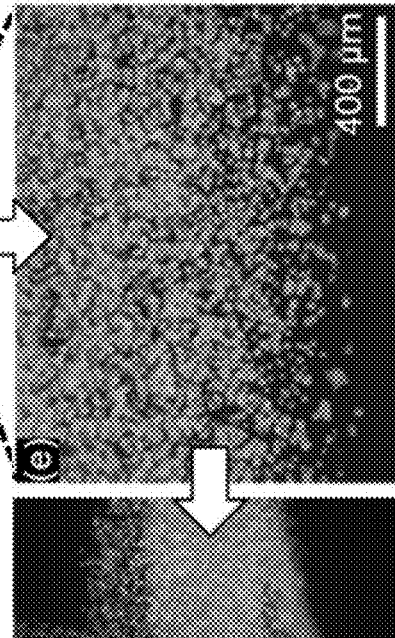
FIG. 44E
FIG. 44F
FIG. 44H
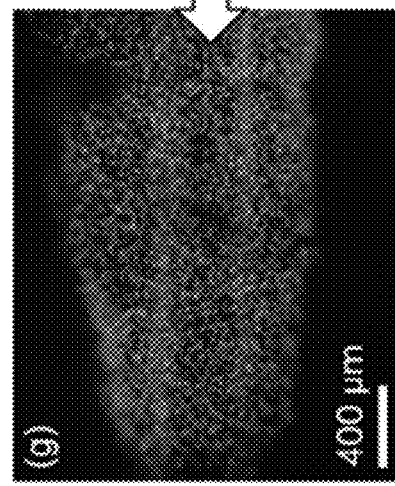
FIG. 44G
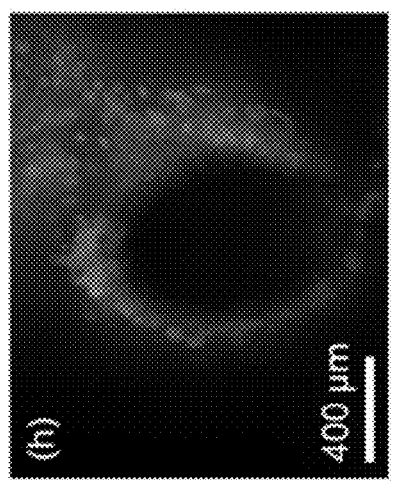

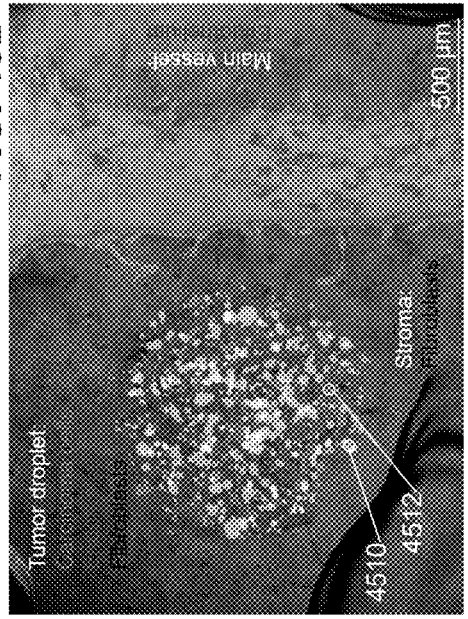
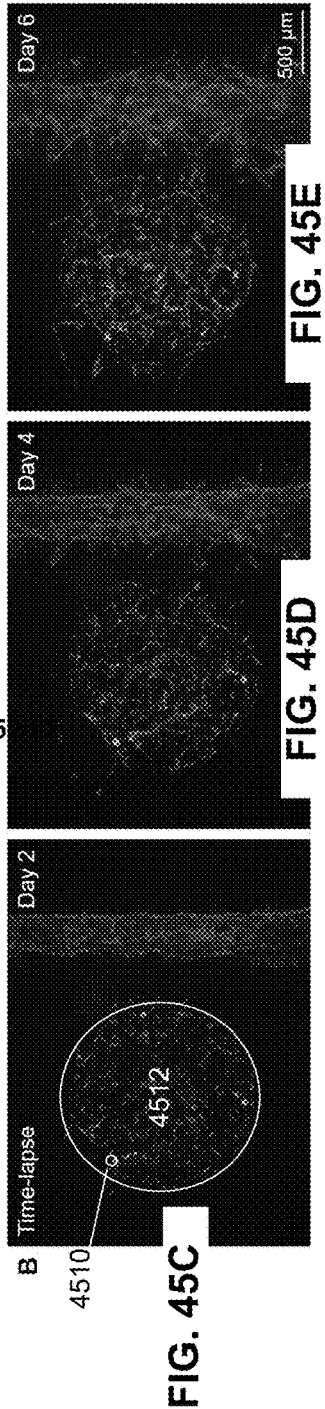
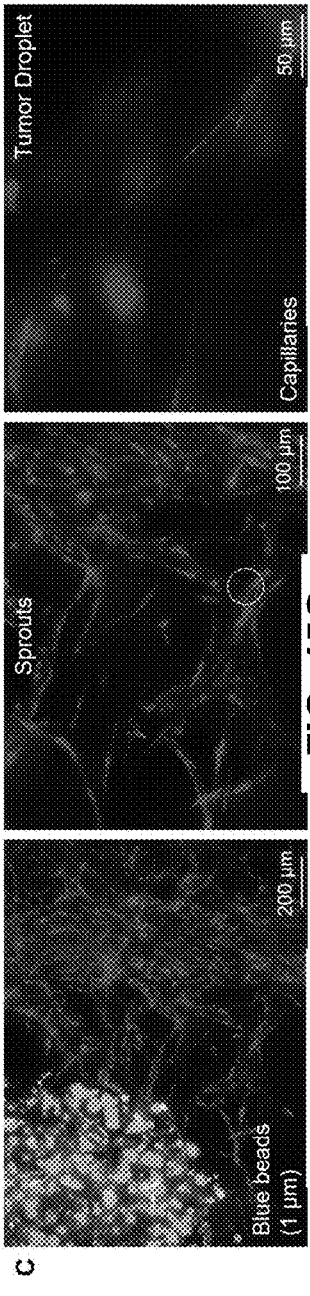

3D-PRINTED MODELS OF BIOLOGICAL MICROENVIRONMENTS

PRIORITY CLAIM

This application claims the benefit of U.S. Provisional Patent Application No. 62/756,039 filed Nov. 5, 2018, the entire content of which is incorporated herein by reference.

GOVERNMENT INTEREST

This invention was made with government support under EB022830 and EB020537 awarded by National Institutes of Health. The government has certain rights in the invention.

TECHNICAL FIELD

This disclosure relates generally to methods for making and using 3D-printed models for biological microenvironments.

BACKGROUND

Biological phenomena may be modeled in vitro using model microenvironments. Such model microenvironments may include physical and/or chemical components associated with the in vivo occurrence of a biological phenomenon of interest. Biological phenomena that may be modeled in model microenvironments include behaviors of living cells, such as cell response to chemical components of the microenvironment.

SUMMARY

This disclosure describes example techniques and systems for making and using 3D-printed model biological microenvironments configured to recapitulate chemical, physical, and/or spatiotemporal aspects of in vivo biological microenvironments. In some examples, such 3D-printed models may enable modeling of biological phenomena of interest (e.g., cancer metastasis), and/or may improve the translatability of potential treatments for diseases or other physiological conditions to in vivo applications. Example techniques described herein include 3D-printing techniques for generating model 3D-printed biological microenvironments that include tissue constructs (e.g., tumor tissue and/or vasculature) via precise placement of living cells, functional biomaterials, and programmable-release capsules. Such model biological microenvironments may enable the spatiotemporal control of signaling molecule gradients, which may dynamically modulate cellular behaviors at a local level.

A 3D-printed in vitro model biological microenvironment in examples discussed below may have one or more of the following features: (a) a gel matrix 3D-printed scaffold, wherein the gel matrix comprises a chemical composition configured to culture a first type of live cells, (b) a target chemical disposed at one or more locations within the gel matrix, the target chemical forming a chemical depot from which a chemical gradient is created within the gel matrix, (c) a conduit disposed within the gel matrix and defining a lumen comprising a second type of live cells, wherein the conduit is configured to enable at least some of the first type of live cells to migrate through the conduit and facilitate flow of at least: some of the live cells to an outlet of the conduit, or enable introduction of at least one of other cells, chemical mediators, or drugs into the 3D-printed microenvironment, (d) a plurality of 3D-printed programmable-release capsules 3D-printed into the gel matrix, each programmable-release capsule may have one or more of the following features: (i) a core 3D-printed into the gel matrix, wherein the core comprises at least one of a target chemical, a molecule, or one or more cells, (ii) a shell coating that may comprise a plurality of localized surface plasmon resonance (LSPR) particles 3D-printed onto the core, wherein the shell coating is configured to be rupturable by laser irradiation with substantially a resonance wavelength of the LSPR particles, and wherein rupture of the shell coating releases the at least one of the target chemical, the molecule, or the one or more cells into the gel matrix such that the target chemical forms the chemical depot within the gel matrix, and (e) the first type of live cells positioned within the 3D-printed microenvironment.

A method of 3D-printing a 3D-printed microenvironment in examples discussed below may have one or more of the following steps: (a) 3D-printing a gel matrix scaffold, wherein the gel matrix comprises a chemical composition configured to culture a first type of live cells, (b) sequentially introducing a target chemical to respective locations within the gel matrix, wherein the target chemical present at the respective locations creates at least one chemical gradient within the gel matrix, (c) introducing a conduit within the gel matrix, (d) defining a lumen comprising a second type of live cells, wherein the conduit is configured to enable at least some of the first type of live cells to migrate through the conduit and facilitate flow of the at least some of the live cells to an outlet of the conduit, (e) injecting a secondary chemical through the conduit, (f) collecting the cells that migrated through the conduit at an outlet of the conduit, (g) 3D-printing a plurality of programmable-release capsules into the gel matrix, wherein 3D-printing each programmable-release capsule can have one or more of the following steps: (i) 3D-printing a core into the gel matrix, wherein the core comprises the target chemical, (ii) 3D-printing a shell coating comprising a plurality of localized surface plasmon resonance (LSPR) particles 3D-printed onto the core, wherein the shell coating is configured to be rupturable by laser irradiation with substantially a resonance wavelength of the LSPR particles, and wherein rupture of the shell coating releases the target chemical into the gel matrix such that the target chemical forms a chemical depot within the gel matrix, (h) positioning a plurality of a first type of live cells within the 3D-printed microenvironment, and (i) positioning a model conduit defining a lumen and positioned within the gel matrix, wherein the model conduit comprises a plurality of a second type of live cells.

A method of determining an effect of a chemical agent on a plurality of live cells using a 3D-printed in vitro model biological microenvironment in examples discussed below may have one or more the following steps: (a) introducing the chemical agent into a lumen defined by a model conduit of the 3D-printed in vitro model biological environment, wherein the 3D-printed in vitro model biological environment may have one or more of the following features: (i) a gel matrix 3D-printed scaffold, wherein the gel matrix comprises a chemical composition configured to culture the plurality of live cells, (ii) the model conduit, wherein the model conduit is positioned within the gel matrix, (iii) the plurality of live cells, wherein the plurality of live cells is positioned within the gel matrix, and wherein the model conduit is configured to facilitate diffusion of the chemical agent though a wall of the model conduit and into the gel matrix, (b) determining an effect of the chemical agent on the plurality of live cells.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 6A, 6B and 6C are a graphical representation of an example technique for 3D-core printing, shell coating, and programmable rupturing of example programmable-release capsules in accordance with examples of this disclosure.

FIG. 7A is a graphical representation of an example technique for 3D printing of example programmable-release capsules in a hydrogel array in accordance with examples of this disclosure.

FIGS. 7B and 7C are digital images of example complex multiple-capsule 3D arrays of multiple types of example programmable-release capsules in hydrogel in accordance with examples of this disclosure.

FIG. 7D is a digital image from a video illustrating an example technique for 3D printing of example programmable-release capsules in a 3D multiplex array in a hydrogel in accordance with examples of this disclosure.

FIG. 9A is scanning electron microscope (SEM) images of example 650 nanometer (nm) and 785 nm LSPR Au nanorods (AuNRs) for encapsulation into functionalized polymer shells of example programmable-release capsules in accordance with examples of this disclosure.

FIG. 9B is digital images of photothermal reaction of 650 nm LSPR AuNRs encapsulated into functionalized polymer shells of example programmable-release capsules following double or single laser rupture of the programmable-release capsules in accordance with examples of this disclosure.

FIG. 9C is a graphical representation of relative absorbance at 405 nanometers (nm) of Texas red-labeled EGF released from capsules containing the 650 nm LSPR AuNRs of FIG. 9B over time following the double or single rupture of the programmable-release capsules under varying conditions.

FIG. 9D is digital images of photothermal reaction of 785 nm LSPR AuNRs encapsulated into functionalized polymer shells of example programmable-release capsules following double or single rupture of the programmable-release capsules in accordance with examples of this disclosure.

FIG. 9E is a graphical representation of relative absorbance at 405 nanometers (nm) of Texas red-labeled EGF released from the 785 nm LSPR AuNRs of FIG. 9D over time following the double or single rupture of the programmable-release capsules under varying conditions.

FIG. 14 is a graphical representation of directional migration of tumor cells under the guidance of EGF gradients generated by 3D-printed programmable-release capsules in accordance with examples of this disclosure.

FIG. 26A is fluorescence images of a conduit of an example vascularized 3D-printed culture chamber illustrating guided extravasation of A549s and subsequent metastases generated over time on days 0 and 2 following the programmable release of EGF from EGF-containing programmable release capsules in accordance with examples of this disclosure.

FIG. 26B is fluorescence images of the conduit of FIG. 26A illustrating guided extravasation of A549s and subsequent metastases generated over time on days 4 and 6 following laser-triggered rupture of EGF-containing programmable-release capsules.

FIG. 41A is fluorescence images of printed A549s after the immunotoxin was injected into a fibroblast-free model though the built-in conduit in an example vascularized 3D-printed culture chamber, showing drug effect over time in accordance with examples of this disclosure.

FIG. 41B is a graphical representation of cellular fluorescence intensity of A549s vs time within fibroblast-laden models and fibroblast-free models, with and without toxin treatment in an example vascularized 3D-printed culture chamber configured for drug testing in accordance with examples of this disclosure.

FIGS. 42C, 42D, 42E, 42F, 42G, 42H, 42I, 42J, 42K, 42L, 42M, and 42N are optical microscope, fluorescence, and photographic images of cells in different example matrices and scaffolds in accordance with examples of this disclosure.

FIGS. 43A, 43B, 43C, 43D, 43E, 43F, 43G, 43H, 43I, 43J, 43K and 43L illustrate a platform containing vascular channels to enable examination of sarcoma cell intravasation and extravasation in accordance with examples of this disclosure.

FIGS. 44A, 44B, 44C, 44D, 44E, 44F, 44G and 44H illustrate aspects of example 4D-printed vascular structures in accordance with examples of this disclosure.

FIG. 45A illustrates a schematic image of a 3D bioprinted in vitro tumor model with multi-scale vascular networks for drug screening FIG. 45B illustrates a composite microscope image (right) showing a representative tumor model FIGS. 45C, 45D and 45E illustrate time-lapse fluorescence images (from Day 2 to Day 6) of a bioprinted model showing the formation of multi-scale vascular networks.

FIG. 45F illustrates a fluorescence image showing the perfusability of the vascular network.

FIG. 45G illustrates a fluorescence image showing the perfusability of the vascular network sprouts between the main conduit and the tumor droplet.

FIG. 45H illustrates a fluorescence image showing the perfusability of the vascular network capillaries formed within the tumor droplet.

DETAILED DESCRIPTION

Figure 1:
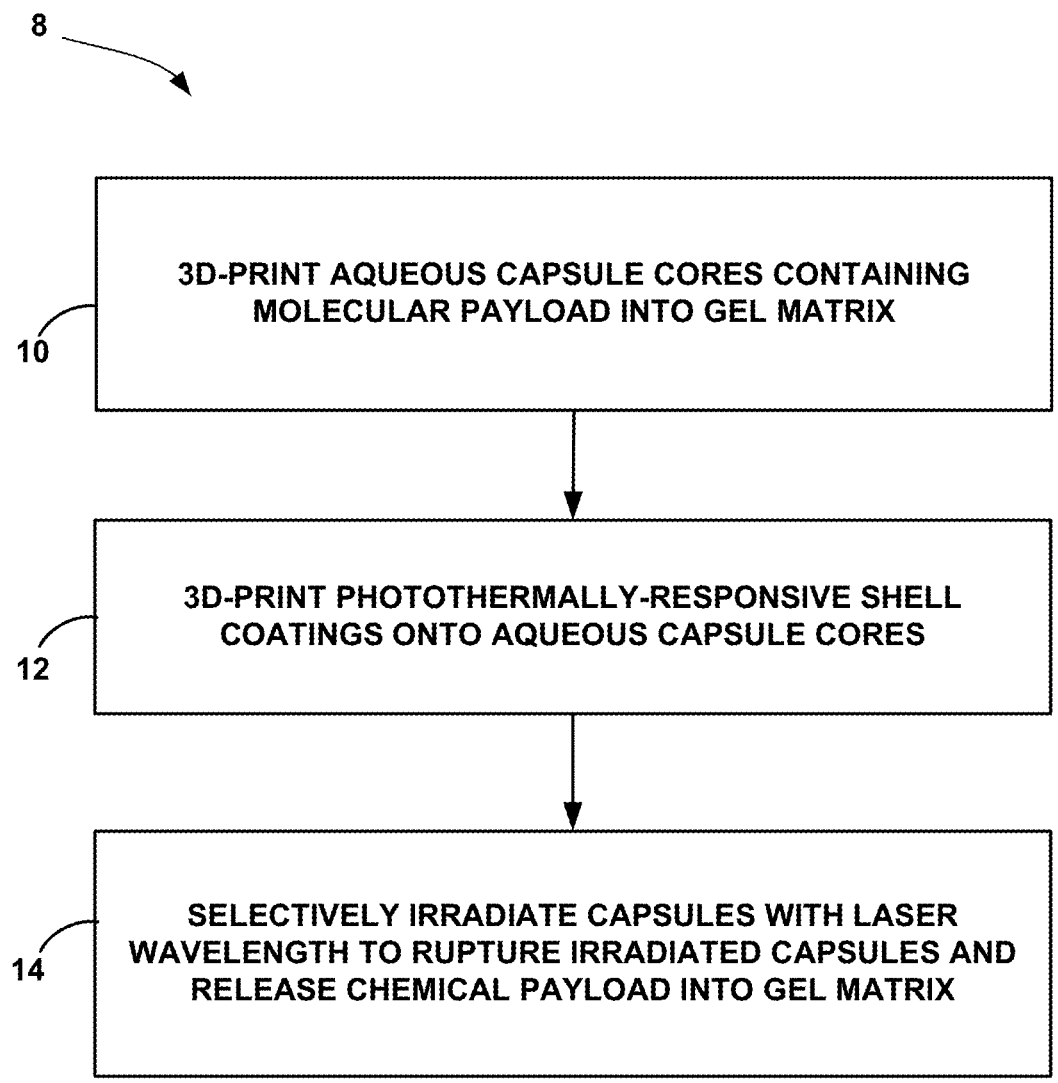
FIG. 1 is a flow diagram illustrating an example technique for 3D-printing and rupturing programmable-release capsules within a 3D-printed model biological environment in accordance with the examples of this disclosure.

In general, this disclosure describes example 3D-printed model biological environments, and example techniques for making and using such example 3D-printed model biological microenvironments. The 3D-printed model biological microenvironments may be configured to recapitulate biological processes having a spatiotemporal aspect, such as metastatic processes by which tumor cells migrate through a stromal environment, into vasculature, and/or out of vasculature. In some examples, 3D-printed model biological environments include a 3D-printed gel matrix with programmable-release capsules 3D-printed therein. The gel matrix may include other matrix components that can be incorporated into a hydrogel, and in which the gel matrix may or may not be laden with cells. A target chemical disposed at one or more locations within the gel matrix can form a chemical depot from which a chemical gradient is created within the gel matrix. The target chemical can be at least one of a signaling molecule. growth factor, a mediator, or DNA containing moiety Such programmable-release capsules may include a chemical agent of interest, (e.g., a biomolecule), that when released from the capsule may form a chemical depot within the gel matrix. Some 3D-printed model biological microenvironments include functional model vasculature. Live cells may be included in the 3D-printed model biological microenvironments, such as 3D-printed or otherwise placed into or on the gel matrix or introduced into model vasculature. Drugs, biomolecules, or other agents may be introduced to live cells within the gel matrix via the model vasculature.

In some examples, the example 3D-printed model biological microenvironments described herein may be constructed to model directional cell migration over time, such as in response to a chemical depot formed by chemicals released from programmable-release capsules 3D-printed within the gel matrix. In some examples, 3D-printed model biological microenvironments may be constructed to model cell extravasation from a model conduit into surrounding gel matrix (e.g., in response to chemical depot(s)) over time, and/or cell intravasation from gel matrix surrounding a model conduit into the model conduit (e.g., in response to chemical depot(s)) over time. In some examples, 3D-printed model biological microenvironments may be constructed to model the effects of compounds (e.g., drugs or biomolecules) or cells (e.g., immune cells) introduced into a model conduit on cells in the gel matrix, thereby recapitulating in vivo drug administration or in vivo distribution of biomolecules or cells via vasculature over time.

Some 3D-printed model biological microenvironments include cell-collection chambers configured to collect cells circulating within the model, such as circulating tumor cells (CTCs) that "self-select" for vascular invasion in the metastatic process. For example, one or more characteristics of such "self-selected" cells may be of diagnostic, prognostic, and/or drug-screening interest. Thus, some example 3-D printed model biological environments described herein may enable non-invasive evaluation of biomolecules, cells, or chemical compounds (e.g., chemotactic or pharmaceutical agents) released from the capsules or from cells in the gel matrix of the model. Cells can be collected by removing the gel portion including the cells, cells can be visualized within the gel without removal for analysis or collecting fluid from the matrix to determine what the cells are doing.

In some examples, the techniques for making and using 3D-printed model biological microenvironments are described using tumor cells as cell types of interest, signaling molecules associated with tumor cells as chemicals of interest contained by programmable-release capsules, and tumor cell migration, extravasation, intravasation, and drug response as biological phenomena of interest. However, the description herein of such techniques is not intended to be limiting to these types of cells, chemicals, or activity. Such techniques may be applied to other cell types, chemicals of interest, and/or biological phenomena of interest. Such techniques may be applied to biological phenomena associated with humans, non-human animals, or other organisms of interest.

The spatiotemporal aspects of some diseases and other health conditions may pose prognostic and therapeutic challenges. For example, the metastatic nature of cancer, which includes the propensity of some cancers to spread over time to locations in the body outside a primary tumor site may pose such challenges. One such challenge is the clinical translation of potential drugs and/or other treatments for health conditions (e.g., cancer), in which there may be a discrepancy between the in vitro and in vivo efficacy of such potential drugs and/or other treatments due to spatiotemporal aspects of a disease or other health condition. For example, expected efficacious drug dosages determined based on results from conventional 2D cell culture monolayers may be lower than an efficacious dosage in vivo, such as due to the physically and chemically simplified nature of such models.

Additionally, or alternatively, models using conventional 2D cell culture monolayers on flat surfaces may not accurately recapitulate the characteristics of native (i.e., in vivo) tumor microenvironments, such as the cell migration that is an important component of metastatic dissemination of tumor cells from a primary tumor to local and distant sites. Although tumor cells can move both randomly and directionally, activities are most efficient when the cells are involved in directed migration. Chemotaxis is the most common mode of directed movement of cells, which is involved in each major step of tumor dissemination. Therefore, chemically-guided cell migration within 3D engineered model tumor tissues may provide an advantageous in vitro platform for the investigation of metastasis or other chemically-guided biological phenomena, which may help enable development of efficient methods of diagnosis, prognosis and treatment.

Some types of cultured cells, such as tumor cell spheroids in 3D hydrogel scaffolds, more closely mimic their natural behaviors in vivo at both phenotypic and genotypic levels, and in their response to anticancer drugs than other types of cultured cells. However, the tumor environment is a complex system with multilevel interactions between numerous components. Such components may contribute to tumor development and progression, both in vivo and in in vitro physical translocations of tumor cells into 3D culture platforms. For example, in addition to tumor parenchymal cells, fibroblasts, and blood conduits, which were incorporated within some example models, other constituents, such as signaling molecules, innate and adaptive immune cells, lymphatic conduits, pericytes, other stromal cells, etc., also contribute to these microenvironments. Thus, more precise models that incorporate these elements of tumor microenvironments may be advantageous for the study of the multilevel interactions that occur at sites adjacent to and distant from a tumor.

To better approximate the specificity and complexity of living tissues, including cell migration, model biological microenvironments that include 3D culture platforms have been developed to mimic the natural microenvironment of tumor tissue. For example, such model biological microenvironments may include recapitulations of in vivo physical structural components (e.g., vasculature, as a tumor needs a dedicated nutrient supply) and dynamic components of extracellular chemical depots. Some such model biological microenvironments may include 3D cell-laden matrices, which may recapitulate physiological cell-cell and cell-extracellular matrix (ECM) interactions.

Compared to conventional 2D monolayer culture, the 3D-printed model biological microenvironments (e.g., metastatic tumor models) may incorporate the advantages of other 3D cell culture systems in addition to other advantageous features. First, the introduction of fibroblasts can facilitate matrix remodeling. Second, the built-in conduit offers a tool to study transendothelial behaviors of tumor cells and allows for the introduction of drug candidates through an endothelial barrier (e.g., through a built-in conduit in the 3D printed model biological microenvironment), mimicking in vivo drug delivery. Third, the model design enables the collection of CTCs that self-select to intravasate. In some examples, active post-fabrication modulation of cell behaviors may be guided via programmable release of printed capsules at a local level. Even though these printed tumor models are simplified relative to the in vivo tumor microenvironment, they may provide clinical translatability beyond traditional laboratory animals in the following aspects: (i) the cellular components of such in vitro models may be entirely human cells; (ii) simplified chemical environments, such as the capsule system, may allow for the isolation of chemical factors of interest, which may help enable definition of molecular mechanisms; (iii) the vasculatures within these models may be uniaxial with a length less than 1 cm, wherein drugs can rapidly target tumor cells; and (iv) ethical issues are minimized by using in vitro models for toxicity assays.

In some examples, step-wise integration of more constituents (e.g., physical or chemical) of interest into the 3D-printed model biological microenvironments described herein may enable improvements in optimization of the heterogeneity, such as within a tumor-simulating model. The flexibility to add functional materials in the extrusion-based 3D-printing processes that may be used to produce the 3D-printed model biological microenvironments described herein may expand the applicability of such models to different types of biological phenomena, as may the ability to precisely place different combinations of cells (e.g., tumor-relevant cells) and hydrogel matrices. In some examples, this flexibility in materials and cell types that may be incorporated into such 3D models may enable customization of the models with patient-specific designs and functionalities by directly using cells collected from individuals.

Thus, in some examples, the 3D-printed model biological microenvironments and methods for the creation of migration-inducing, vascularized models (e.g., tumor models) may help bridge the gap between 2D monolayer cell culture and animal models. These 3D cell-laden architectures were fabricated to capture the primary characteristics of the metastatic translocation of tumor cells in vitro. The preclinical application was demonstrated by the effective screening of targeting immunotoxins with anti-cancer efficacy. The 3D-printed model biological microenvironments may physically and/or chemically reconstruct the microenvironments of tumors with high spatiotemporal resolution, which offer tools to: (i) advance 3D tissue engineering for dynamic mimicking of the in vivo natural microsystem with capabilities of post-fabricated modulation, (ii) further understand the mechanisms of metastatic dissemination, (iii) screen novel anti-cancer drugs, and (iv) test patient-specific strategies of diagnosis and therapeutics.

In some examples described herein, 3D-printed model biological microenvironments (e.g., tumor models) that physically and/or chemically approximate a tumor microenvironment may enable modeling of one or more components of metastatic dissemination, including invasion, extravasation, intravasation and angiogenesis. 3D-printing techniques provide an approach to the design and fabrication of complex biological microenvironments (e.g., tissue constructs) in vitro. For example, 3D printing of such model biological microenvironments enables the integration of numerous combinations of living cells and supporting matrices with precise spatial control, resulting in engineering of numerous tissues with promising biomedical applications.

For example, 3D-printing techniques may enable precise placement of model components such as tumor cells, vascular cells, and/or stromal cells within a 3D-printed model biological microenvironment according to their physiological functions. 3D-printed model biological microenvironments may include 3D-printed stimuli-responsive core/shell capsules that enable creation and manipulation of extracellular chemical depots (e.g., biomolecule gradients) within gel matrices of 3D-printed model biological microenvironments via programmable release of contents of the capsules. In some examples, the capsules may contain growth factors (e.g., EGF) or other chemical payloads that may enable post-printing modulation of cell behavior.

In some examples in which the microenvironment is a tumor microenvironment, the modularized construction of vascularized models may help enable the creation of tumor-vascular constructs in the context of other cell types, such as stromal cells. Culture-medium chambers included in some such design of the printed culture chambers allows for enrichment and collection of circulating tumor cells that have 'self-selected' to enter a vascular conduit included in the 3D-printed model biological microenvironment In some examples, such models may model tumor metastasis and may be used as a pre-clinical tool for anti-cancer drug screening: the efficacy of targeted cancer drugs can be evaluated with the tumor models.

FIG. 1 is a flow diagram illustrating an example technique for 3D printing and rupturing programmable-release capsules within a 3D-printed model biological environment in accordance with the examples of this disclosure. According to the example of FIG. 1, cores of the programmable-release capsules are 3D-printed into a gel matrix of an example 3D-printed model biological microenvironment (10) of process 8. In some examples, the cores may include a hydrogel material. In other examples, the cores may include an aqueous material. The 3D-printed biological microenvironment may include a scaffold or platform, such as a silicone scaffold, onto which the programmable-release capsules may be 3D-printed. In some examples, the material of the cores may include a carrier material and a chemical payload contained therein. As discussed herein, the chemical payload of the cores may be substantially any chemical of interest, such as a drug, biomolecule, or other chemical that may form a chemical depot within the gel matrix. In some examples, a 3D-printed model biological microenvironment may include programmable-release capsules having different chemicals of interest. In any such examples, the programmable-release capsules may be 3D-printed in substantially any pattern and/or in substantially any desired area within the gel matrix, such as in layers throughout a depth of a gel matrix, and/or in discrete regions of the gel matrix.

Following 3D-printing of the cores of the programmable-release capsules into the gel matrix, shell coatings are 3D-printed over the cores (12). As discussed below with respect to FIGS. 9A-9E, a shell ink from which the shell coatings are 3D-printed may include a polymer or other carrier. The shell ink also may contain LSPR nanorods, or other photothermically reactive particles, such as LSPR AuNRs that provide a photothermal reaction in response to irradiation with a laser.

Next, 3D-printed programmable-release capsules are ruptured using a laser of substantially the same wavelength as a resonance wavelength of the LSPR AuNRs (14). For example, the 3D-printed programmable-release capsules may be ruptured following placement of living cells (e.g., tumor cells) into the gel matrix, such as by 3D-printing the cells or by other suitable methods. In some examples, the programmable-release capsules may be ruptured via laser at substantially concurrently or may be ruptured at different times. In this manner, the technique of FIG. 1 may enable creation of chemical depots of a chemical of interest within a 3D-printed model microenvironment that may recapitulate spatiotemporal aspects of chemical depots formed in vivo. It is of note, the programmable-release capsules could be replaced by nanoparticles which can still be ruptured with a laser.

Figure 2:
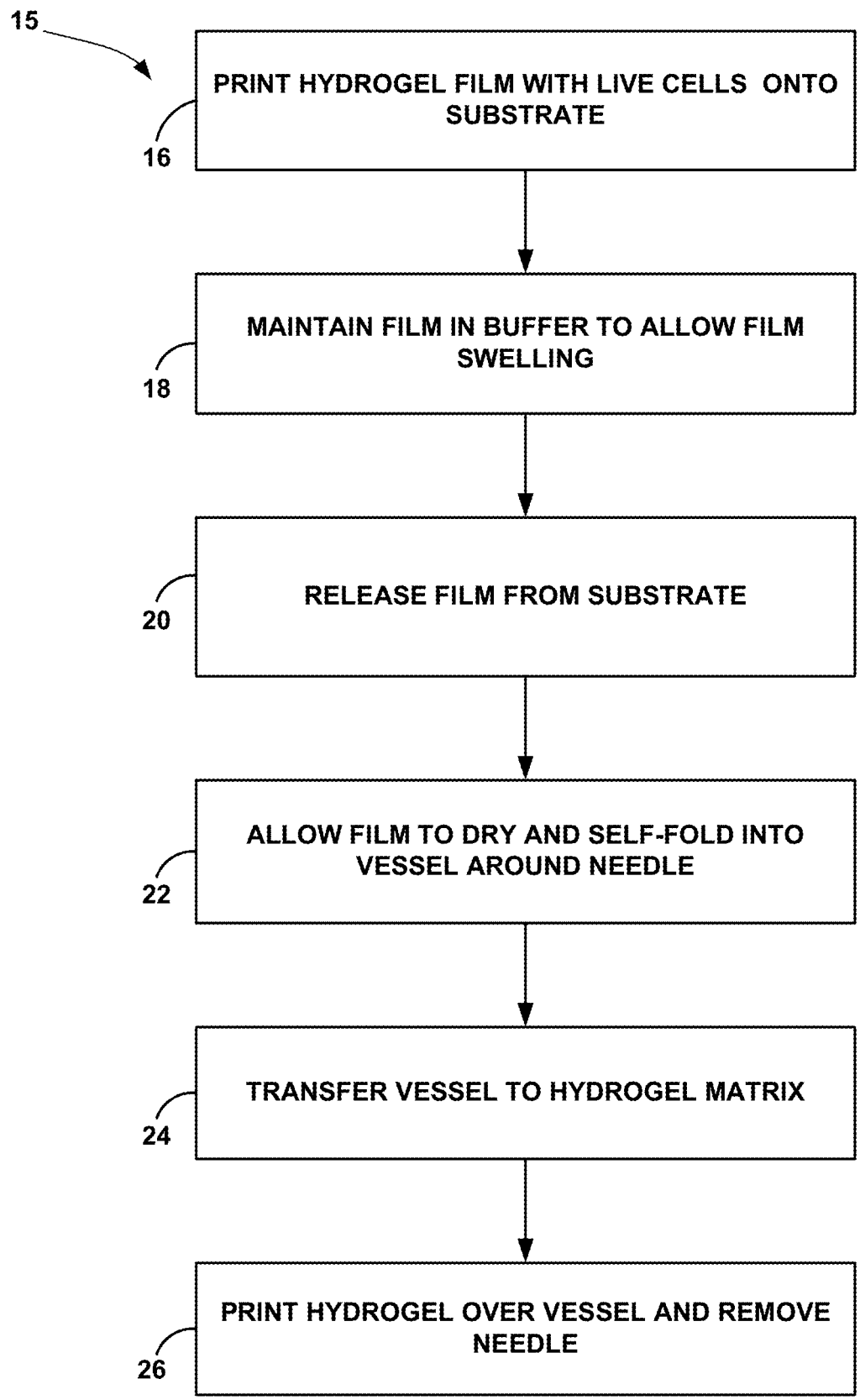
FIG. 2 is a flow diagram illustrating an example technique for 4D-bioprinting a vascular structure within a 3D-printed model biological environment in accordance with the examples of this disclosure.

FIG. 2 is a flow diagram illustrating an example technique for 4D-bioprinting a vascular structure within a 3D-printed model biological environment in accordance with the examples of this disclosure. Additional aspects of example techniques for 4D-bioprinting a vascular structure are discussed below with respect to FIGS. 42A-44H. According to the example of FIG. 2, a hydrogel film containing live cells is 3D-printed onto a substrate (16) of process 15. In some examples, the cells may be endothelial cells, such as HUVECs (human umbilical vein cells). Next, the hydrogel film is maintained in a suitable buffer solution to allow the hydrogel film to swell (18). After the hydrogel film has swelled, the hydrogel film is released from the substrate (20).

The hydrogel film then is allowed to dry and self-fold into a conduit structure (22). In some examples, the hydrogel film is allowed to self-fold into a conduit structure around a needle, which may enable placement of the conduit into a gel matrix of a 3D-printed model biological microenvironment. The direction of the self-folding of the hydrogel film may be controlled by one or more factors, such as by the incorporation of ridge arrays into the substrate onto which the hydrogel film is printed. After the hydrogel film has self-folded into a conduit structure, the conduit is transferred to a gel matrix of a 3D-printed model biological microenvironment (24). For example, the conduit may be transferred to the gel matrix during 3D-printing of the gel matrix. After the conduit is transferred to the gel matrix of the 3D-printed model biological microenvironment, a layer of the gel matrix is 3D-printed over the conduit, such that the conduit is enclosed within the gel matrix of the 3D-printed model biological microenvironment, and the needle is removed from the conduit (26). In this manner, the technique of FIG. 2 may enable creation of a 3D-printed model biological microenvironment vascularized with model vasculature that includes living endothelial cells, one or more features of which may be substantially similar to those of in vivo vasculature.

Figure 3:
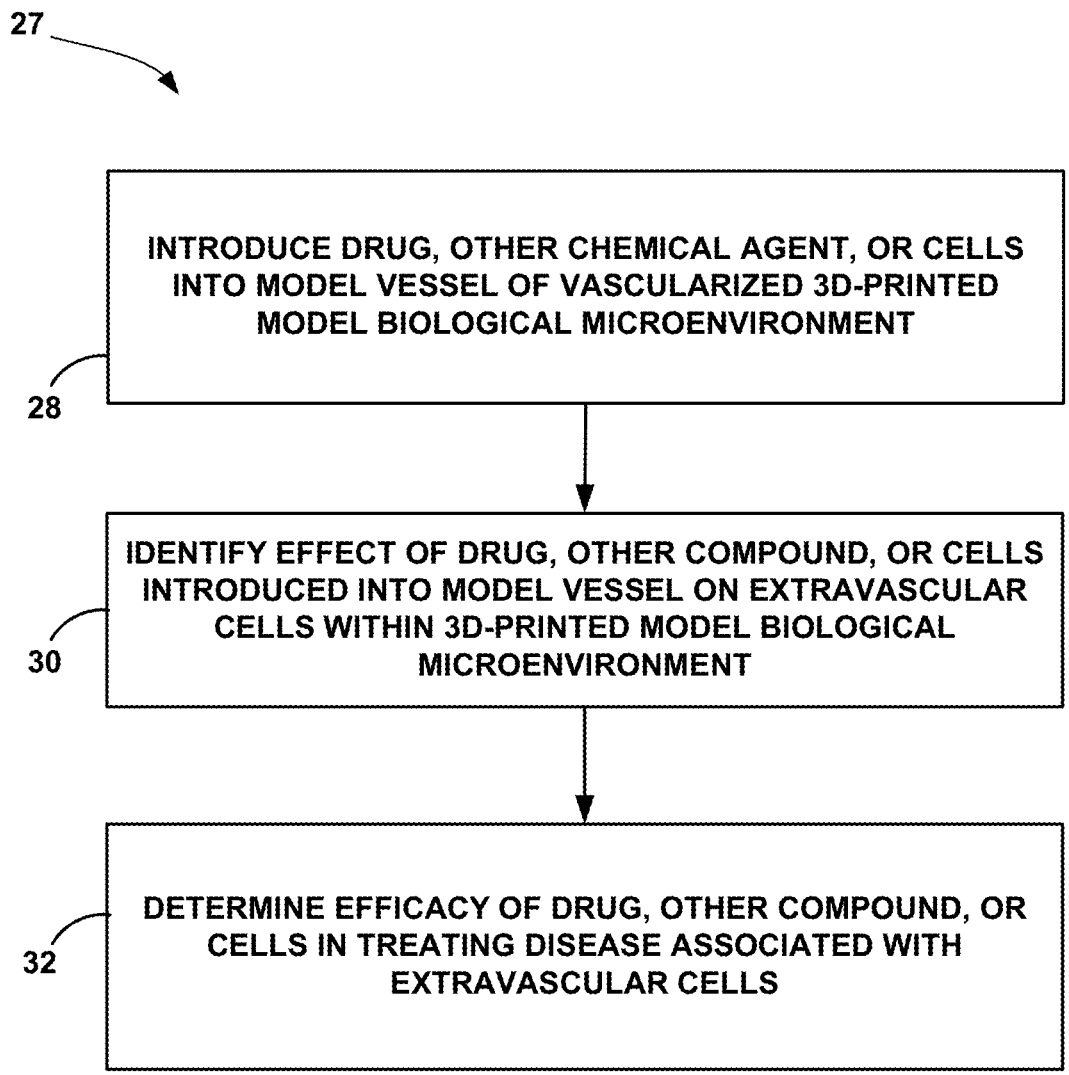
FIG. 3 is a flow diagram illustrating an example technique for testing effects of a drug or other agent on a cell type of interest in accordance with the examples of this disclosure.

FIG. 3 is a flow diagram illustrating an example technique for testing effects of a drug or other agent (e.g., other chemical or type of cell) on a cell type of interest in accordance with the examples of this disclosure. According to the example of FIG. 3, a drug, other chemical agent, or type of cell (e.g., type of immune cell) is introduced into a model conduit of an example vascularized 3D-printed model biological microenvironment (28) of process 27. In some examples, the vascularized 3D-printed model biological microenvironment may include cells of the cell type of interest (e.g., type of tumor cell) 3D-printed or otherwise placed into a gel matrix of the 3D-printed model biological microenvironment outside the model conduit. The drug, other chemical agent, or type of cell then may diffuse or extravasate from the conduit into the gel matrix of the 3D-printed model biological microenvironment, where it may interact with cells of the cell type of interest in the gel matrix. Cells of the cell type of interest then are collected and evaluated, and the effect of the drug, other chemical agent, or type of cell on the cell type of interest (30). For example, the drug, other chemical agent, or type of cell may reduce the viability of the cell type of interest. The efficacy of the drug, other chemical agent, or type of cell in treating a disease associated with the cell type of interest then is determined (32). For example, the drug, other chemical agent, or type of cell reduces the viability of the cell type of interest, which may be determined to be efficacious in examples in which the drug, other chemical agent, or type of cell reduces the viability of the cell type of interest. In some examples, more than one drug, other chemical agent, or type of cell may be introduced into the model conduit. For example, immune cells that may kill tumor cells and a drug or other chemical that may enhance the tumor-cell killing activity of the immune cells both may be introduced into the model conduit. In this manner, separate and/or additive effects of multiple substances and/or cells introduced into the model conduit on cells in the gel matrix may be identified.

Figure 4:
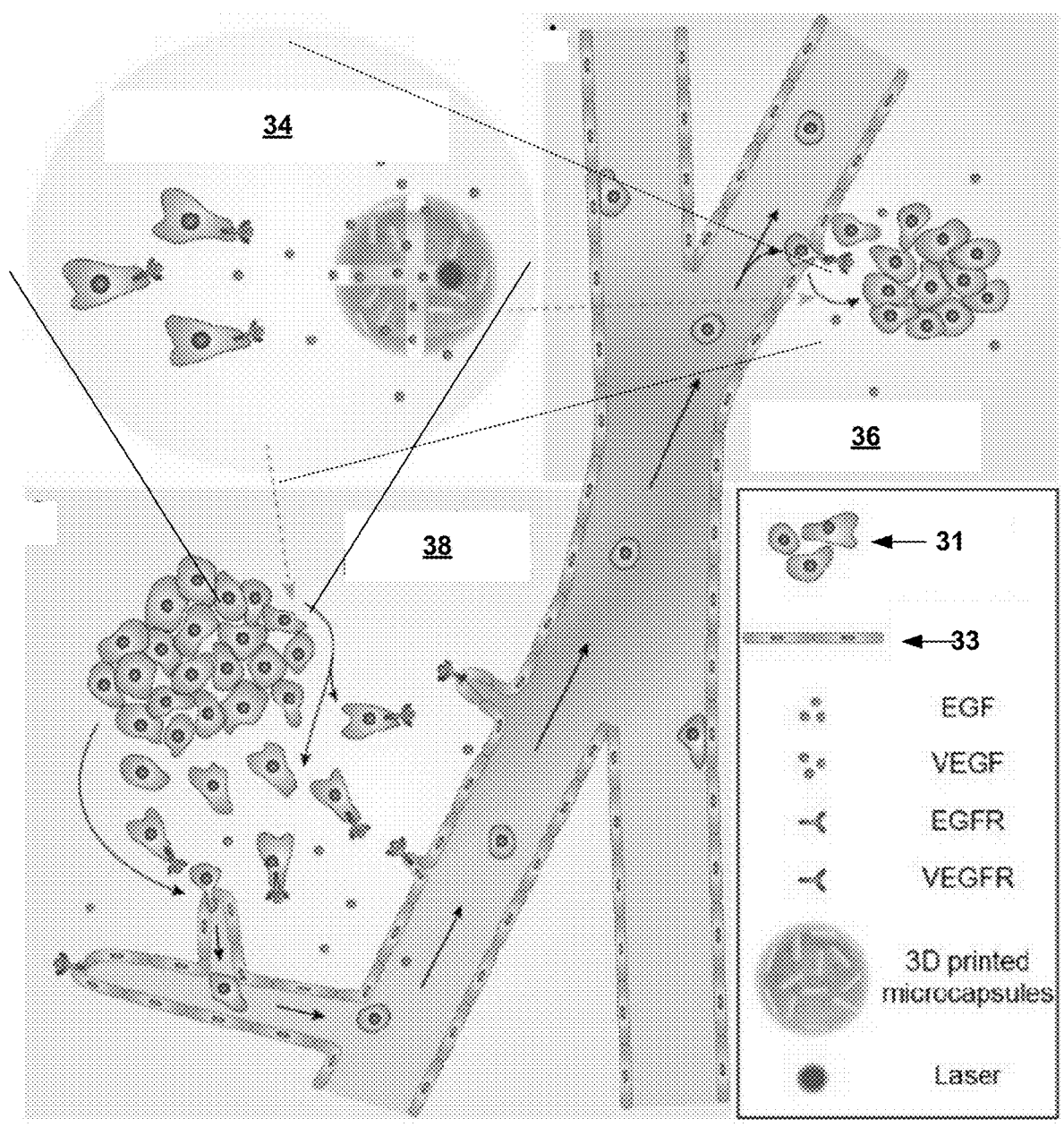
FIG. 4 is a flow diagram illustrating an example technique using 3D-printed model tumor microenvironments to recapitulate metastatic dissemination in accordance with examples of this disclosure.

FIG. 4 is a flow diagram illustrating an example technique for using 3D-printed model biological microenvironments to recapitulate metastatic dissemination in accordance with examples of this disclosure. In some examples, the 3D-printed biological microenvironments described herein may include chemical depots (e.g., biomolecular gradients) that are dynamically generated within hydrogel matrices via controllable release of growth factors from 3D-printed programmable-release. Such growth factors may mimic chemical environments in tumor cells 31 and direct cell migration (34). Perfusable conduits may be integrated into the 3D-printed biological microenvironment, such as via 4D printing of the conduits, to provide vascular paths, which may enable probing of the process by which tumor cells 31 extravasate through an endothelial barrier 33 to form extravascular metastases (36). Multiple chemotactic pathways may be programmed to guide both the tumor cell invasion of the perfusable conduits and angiogenesis (38), thereby creating intravasation models that may recapitulate the initiation of cancer spreading (i.e., metastasis).

Figure 5:
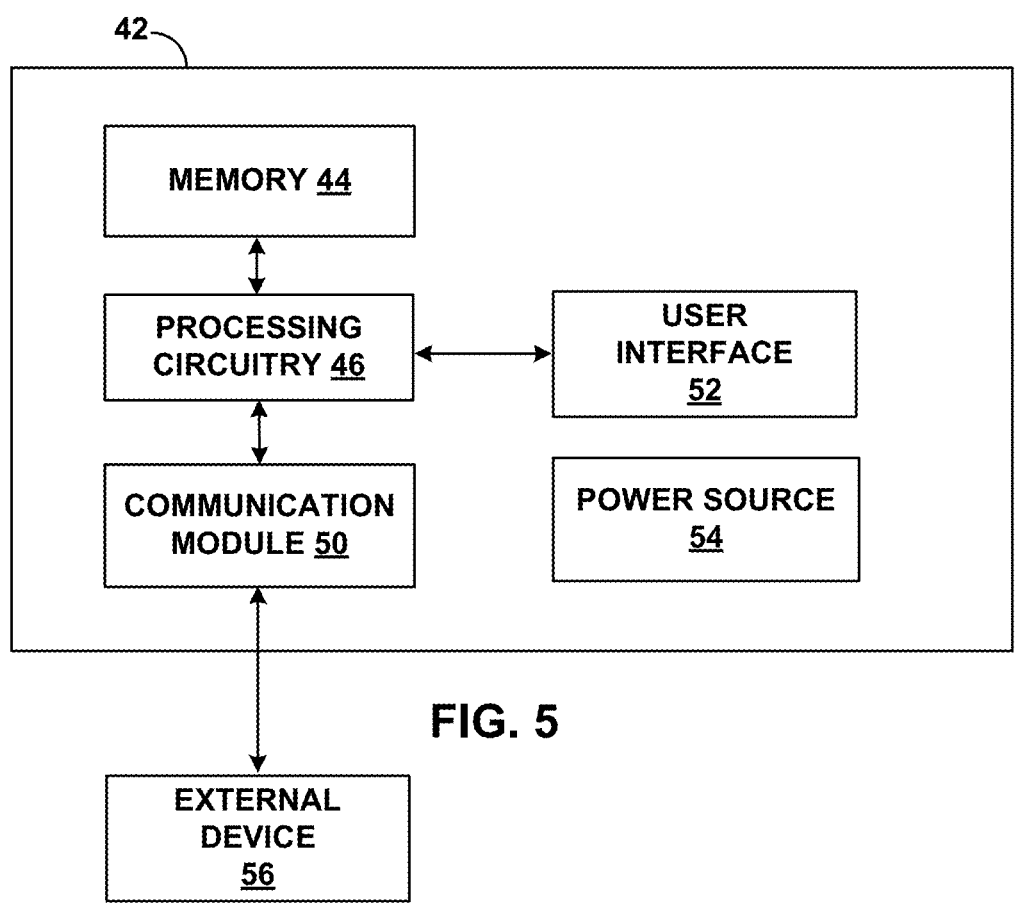
FIG. 5 is a functional block diagram illustrating an example configuration of a computing device that may be used to control the 3D-printing and/or laser delivery steps of the techniques described herein.

FIG. 5 is a functional block diagram illustrating an example configuration of a computing device 40 that may be used to control one or more aspects of the 3D-printing and/or laser delivery steps of the techniques described herein. In the example illustrated in FIG. 5, computing device 40 includes memory 44, processing circuitry 46, communication module 50, user interface 52, and power source 54. Processing circuitry 46 may include one or more processors. In one example, processing circuitry 46 is configured to run the software instructions in order to control operation of external device 56. In some examples, external device 56 may be a 3D-printing apparatus, and the software instructions run by processing circuitry 46 may be instructions for 3D-printing programmable-release capsules, gel matrices, cells, or other materials of the example 3D-printed model biological microenvironments described herein. In some examples, external device 56 may be an apparatus configured to generate and deliver laser wavelengths, and the software instructions run by processing circuitry 46 may be instructions for the apparatus configured to generate and deliver laser wavelengths to deliver a laser wavelength to rupture 3D-printed programmable-release capsules of the example 3D-printed model biological microenvironments described herein.

Processing circuitry 46 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 44 may include any volatile or non-volatile media, such as a random access memory (RAM), read only memory (ROM), non-volatile RAM (NVRAM), electrically erasable programmable ROM (EEPROM), flash memory, and the like. Memory 44 may store information including instructions for execution by processing circuitry 46 such as, but not limited to, instructions for performing one or more steps of the techniques described herein. Communication module 50 may provide one or more channels for receiving and/or transmitting information, such as to or from external device 56. Communication module 50 may be configured to perform wired and/or wireless communication with other devices, such as radio frequency communications. In other examples, communication module 50 may not be implemented, and instead, memory 44 may be removable (e.g., a removable flash memory).

Power source 54 delivers operating power to various components of computing device 218. Power source 54 may generate operational power from an alternating current source (e.g., residential or commercial electrical power outlet) or direct current source such as a rechargeable or non-rechargeable battery and a power generation circuit to produce the operating power. In other examples, non-rechargeable storage devices may be used for a limited period of time.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including a 3D-printing apparatus, laser source, a programming device configured to control a 3D-printing apparatus and/or a laser source, a combination of a 3D-printing apparatus, a laser source, and a programming device, an integrated circuit (IC) or a set of ICs, and/or discrete electrical circuitry, residing in a 3D-printing apparatus, a laser source, and/or a programming device.

Further aspects of the disclosure will now be discussed, including further details of the 3D-printed model biological microenvironments described herein, as well as techniques for the manufacture and use thereof. Some such details and techniques are described in the context of working examples and experimental results illustrating the results of some such techniques for the manufacture and use of the example 3D printed model biological microenvironments. It is contemplated that the example laboratory techniques described for accomplishing routine laboratory tasks, such as the collection and pre-3D printing culture of cells, as well as others, are not intended to be limiting and may be performed by any suitable laboratory techniques. In addition to the techniques described above, supplementary techniques, as described below, may be employed. Cells from organisms other than humans may be used in some applications of the example techniques herein. Additionally, or alternatively, biological phenomena associated with cells and/or biomolecules in the context of any particular disease or physiological condition of interest may be modeled in some applications of the 3D-printed model biological microenvironments described herein.

FIGS. 6-9E are graphical representations and images of aspects of example 3D-printed programmable-release capsules, which also may be referred to herein simply as "capsules." The examples of FIGS. 6A-9E should not be considered limiting, as example 3D-printed programmable-release capsules may differ in composition or method of 3D-printing relative to the examples described below with respect to FIGS. 6-9E.

FIGS. 6A-C are a graphical representation of an example technique for 3D-core printing, shell coating, and programmable rupturing of example programmable-release capsules in accordance with examples of this disclosure. In some examples, the capsules may include a core containing a payload of functional molecular factors and a biocompatible polymer shell containing LSPR AuNRs. As illustrated in FIG. 6A, during printing of the capsules, cores 60 may be deposited onto a substrate 62, such as a hydrogel, using any suitable 3D-printing equipment. The cores 60 may maintain the activities of biomolecular payloads contained therein. In some examples, cores 60 containing different biomolecular payloads may be deposited onto the substrate 62. The biomolecular payloads may be any molecules associated with a biological phenomenon of interest. For example, the biomolecular payloads may be growth factors associated with tumor cell migration, extravasation, intravasation, or others. Shells 64 functionalized with biocompatible polymer shell 64 containing the plasmonic AuNRs 68 then may be coated onto the cores 60 of the capsules using any suitable 3D-printing equipment 66. The photothermal response of the AuNRs within the shells 64 of the capsules permit selective rupturing of the capsules 68 when irradiated with a laser wavelength of laser wavelengths 69 determined by the aspect ratio of the AuNRs.

For example, as illustrated in FIG. 6C, fewer than all the capsules 68 present on a substrate 62 may be irradiated at a time with laser wavelengths 69, leaving other capsules 68 intact at least until a later time. In some examples, capsules 68 containing a particular of molecular payload may be irradiated substantially simultaneously while capsules 68 containing a different molecular payload may be irradiated at a later time. Additionally, or alternatively, some capsules 68 containing a particular payload may be irradiated at a time while other capsules 68 containing that molecular payload may be irradiated at a later time. As discussed below, following irradiation, the molecular payload may diffuse out from the core of the capsule and through the substrate 62. This approach may enable both spatial and temporal generation of chemical cues in 3D matrices within the 3D-printed model biological microenvironments, which may help enable post-print dynamic regulation of cellular behaviors at a local level.

FIGS. 7A-7D illustrate 3D-printing of example capsules in complex 3D arrays such that the capsules are directly interwoven within a hydrogel matrix, thus combining additive manufacturing techniques and functional plasmonic nanomaterials. In some examples, the example 3D-printed capsule arrays 70 may enable efficient encapsulation of biomolecular payloads and/or selective stimuli response.

FIG. 7A is a graphical representation of an example technique for 3D printing with a 3D printer of example programmable-release capsules in a hydrogel array in accordance with examples of this disclosure. FIG. 7A illustrates that capsules 68 may be 3D-printed in a complex hydrogel array 72 in multi-layer arrangements (e.g., layers 71A-71N, collectively layers 71), with multiple capsules 68 in each layer 71A-71N. This 3D-printing technique may be used to print capsules throughout a thickness of a hydrogel substrate 72 in example 3D-printed model biological microenvironments described herein, such as model tumor microenvironments. In some such examples, the hydrogel substrate 72 may be 3D printed in conjunction with the capsules 68, such as by 3D-printing alternating layers 71A-71N of hydrogel 72 and capsules 68.

FIGS. 7B and 7C are digital images of example complex multiple-capsule 3D arrays 70 of multiple types of example programmable-release capsules 68 in hydrogel 72 in accordance with examples of this disclosure. As shown in FIGS. 7B and 7C, the capsules 68 may be 3D-printed such that the capsules 68 are dispersed in well-defined spatial patterns. In some such examples, the capsules 68 may be 3D printed independently and precisely volume and composition control. In some examples, multiple types of capsules 68 (e.g., capsules having cores that contain different payloads) may be 3D printed onto multiple layers 72 in hydrogel.

FIG. 7D is a digital image from a video illustrating an example technique for 3D printing of example programmable-release capsules 68 in a 3D multiplex array 70 in a hydrogel 72 in accordance with examples of this disclosure FIGS. 8A-8D illustrate aspects of example 3D-printed cores of in accordance with example 3D-printed capsules of this disclosure. In some examples, 3D printing of the cores 60 (e.g., hydrogel cores and/or aqueous cores) may enable precise spatial control over 3D-printing of the capsules 68. The "ink" used in printing the cores 60 of example 3D-printed capsules may provide one or more desired aspects of functionality, printability, and/or activity. For example, the core ink of some example cores may be functionalized with one or more types of molecules capable of forming a biomolecular gradient within the 3D-printed model biological microenvironments described herein, such as enzymes, cytokines, nucleic acids, or other molecules. The composition of the core ink may be selected to provide printability in 3D-printing equipment. For example, the core ink may include polyvinyl alcohol (PVA), gelatin, or other compounds having a particular viscosity and/or surfactant quality that may provide printability. In some examples, the composition of the core ink may be configured to have a humectant activity, which may be provided by ethylene glycol, glycerol, or other suitable substances.

Figures 8A, 8B, 8C, 8D:
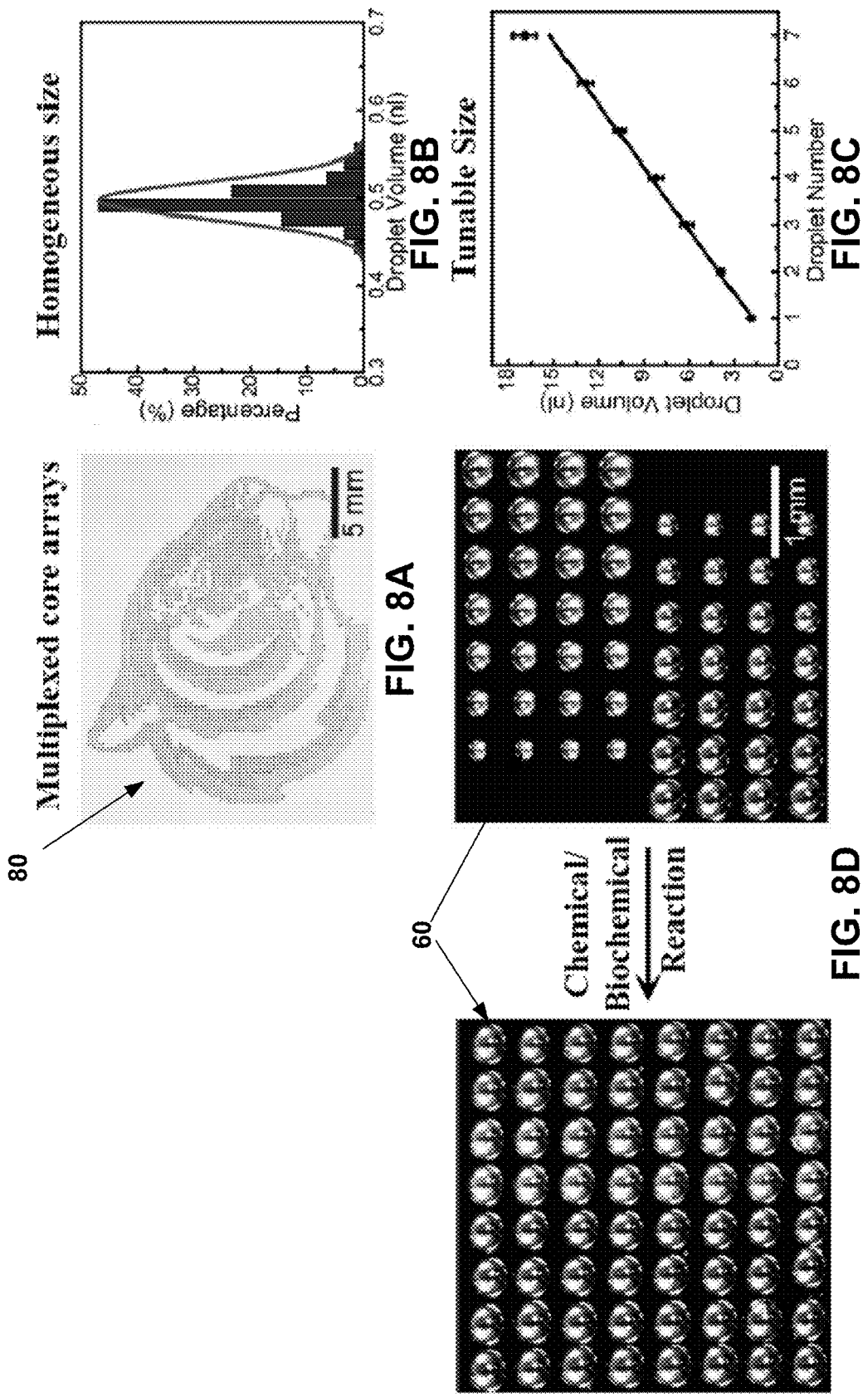
FIG. 8A is a digital image of an example multiplexed core array of 3D-printed cores of example programmable-release capsules in accordance with examples of this disclosure.
FIG. 8B is a graphical representation of percentages of 3D-printed cores having substantially homogeneous droplet volumes in nanoliters (nL) in a sample of 3D-printed cores of example programmable-release capsules in accordance with examples of this disclosure.
FIG. 8C is a graphical representation of percentages of 3D-printed cores having tunable droplet volumes in a sample of 3D-printed cores of example programmable-release capsules in accordance with examples of this disclosure.
FIG. 8D is a digital image of 3D-printed cores of example programmable-release capsules having tunable or substantially homogeneous volumes in accordance with examples of this disclosure.

FIG. 8A is a digital image of an example multiplexed core array of 3D-printed cores of example programmable-release capsules in accordance with examples of this disclosure. As illustrated in FIG. 8A, one or more aspects of the core ink of the cores described herein may provide spatial control over the core ink, which may enable the cores to be 3D printed in multiplexed complex arrays 80. The core ink provides functionality through enzymes, cytokines, DNA and other biomolecular gradients. The core ink provides printability through the use of polyvinyl alcohol (PVA) or gelatin providing viscosity and surfactant. The core ink also provides activity with ethylene glycol/glycerol (humectant).

FIG. 8B is a graphical representation of percentages of 3D-printed cores having substantially homogeneous droplet volumes in nL (nano liters) in a sample of 3D-printed cores of example programmable-release capsules in accordance with examples of this disclosure. In some examples, one or more aspects of the core ink and/or 3D printing equipment may enable 3D printing of cores having substantially homogenous volume. For example, as illustrated in FIG. 8B, cores having volumes substantially homogeneous between 0.45 nL and about 0.55 nL may be 3D printed.

FIG. 8C is a graphical representation of percentages of 3D-printed cores having tunable droplet volumes in a sample of 3D-printed cores of example programmable-release capsules in accordance with examples of this disclosure. In some examples, 3D-printed cores of some example capsules may be printed to have varying volumes, as illustrated in FIG. 8C. In any such examples, the volume of the 3D-printed cores may be tightly controlled, which may provide tunability to one or more aspects of the example 3D-printed model biological environments described herein.

FIG. 8D is a digital image of 3D-printed cores 60 of example programmable-release capsules having tunable or substantially homogeneous volumes in accordance with examples of this disclosure.

FIGS. 9A-9E illustrate aspects of example 3D-printed functionalized shells in accordance with example 3D-printed capsules of this disclosure. In some examples, the functionalized shells may provide responsive temporal control over the rupturing of the capsules. For example, the shells may be 3D printed from a shell ink that is configured to be printable, retain the core until capsule rupture, and release the core upon selective rupture of the capsule. In some examples, the shell ink may include a polymer such as poly(lactic-co-glycolic acid) (PLGA), which is an FDA-approved polymer with a suitable transformation temperature ($T_g$). The composition of the shell ink may be selected to provide printability in 3D-printing equipment, such as compounds having a particular viscosity and/or surfactant quality that may provide printability. The shell ink also may contain LSPR AuNRs that provide a photothermal reaction in response to irradiation with laser of substantially the same wavelength as a resonance wavelength of the LSPR AuNRs.

FIG. 9A is scanning electron microscope (SEM) images of example 650 nm and 785 nm LSPR AuNRs for encapsulation into functionalized polymer shells of example programmable-release capsules in accordance with examples of this disclosure. As illustrated in FIG. 9A, LSPR AuNRs may have differing lengths and may be configured to photothermically react to different laser wavelengths, such as 650 nm or 785 nm. In some examples, the different configurations of the LSPR AuNRs may enable selective rupturing depending upon the laser wavelength used.

FIG. 9B is digital images of photothermal reaction of 650 nm LSPR AuNRs encapsulated into functionalized polymer shells of example programmable-release capsules following double or single laser rupture of the programmable-release capsules in accordance with examples of this disclosure. As shown in FIG. 9B, release of capsule payload (here, horseradish peroxidase (HRP) from an example capsule following laser-wavelength rupture of the capsule with a single laser is more gradual than release of capsule payload following laser-wavelength rupture of a capsule with a double laser. This variable release of payload observed with single- or double-laser capsule rupture may provide another aspect of tunability to the 3D-printed model biological environments described herein by enabling temporal control of molecular gradient generation.

FIG. 9C is a graphical representation of relative absorbance at 405 nanometers (nm) of HRP released from the capsules containing the 650 nm LSPR AuNRs of FIG. 9B over time following the double or single rupture of the capsules under varying conditions, which was indicative of amount of HRP released from the capsules over time. As illustrated in FIG. 9C, substantially no HRP was released from the capsules over 60 minutes in the absence of laser irradiation. Similarly, substantially no HRP was released from the capsules over 60 minutes following irradiation of the 650 nm LSPR AuNR-containing capsules with a 783 nm laser. However, HRP was released from the capsules over 60 minutes following irradiation of the 650 nm LSPR AuNR-containing capsules with a 658 nm laser, with peak relative absorbance occurring earlier when capsules were ruptured with a single laser than when capsules were ruptured with a double laser. This illustrates that tuning the wavelength of the laser to the resonance of the LSPR AuNRs results in capsule rupture following irradiation, and that a laser wavelength not tuned to the resonance of the LSPR AuNRs does not result in significant capsule rupture.

FIG. 9D is digital images of photothermal reaction of 785 nm LSPR AuNRs encapsulated into functionalized polymer shells of example programmable-release capsules following double or single rupture of the programmable-release capsules in accordance with examples of this disclosure. As with the capsules of FIG. 9B and as shown in FIG. 9D, release of capsule payload (here, HRP) from an example capsule following laser-wavelength rupture of the capsule with a single laser is more gradual than release of capsule payload following laser-wavelength rupture of a capsule with a double laser.

FIG. 9E is a graphical representation of relative absorbance at 405 nanometers (nm) of HRP released from the 785 nm LSPR AuNRs of FIG. 9D over time following the double or single rupture of the programmable-release capsules under varying conditions, which was indicative of amount of HRP released from the capsules over time. As illustrated in FIG. 9E, substantially no HRP was released from the capsules over 60 minutes in the absence of laser irradiation. Similarly, substantially no HRP was released from the capsules over 60 minutes following irradiation of the 785 nm LSPR AuNR-containing capsules with a 658 nm laser. However, HRP was released from the capsules over 60 minutes following irradiation of the 785 nm LSPR AuNR-containing capsules with a 658 nm laser, with peak relative absorbance occurring earlier when capsules were ruptured with a single laser than when capsules were ruptured with a double laser.

Four example 3D-printed model biological microenvironments will now be described below with respect to the drawings. FIGS. 10-21 illustrate an example 3D-printed directional cell migration chamber. FIGS. 22-27 illustrate an example vascularized 3D-printed model biological microenvironment configured to recapitulate tumor cell extravasation during metastasis. FIGS. 28-37B illustrate an example vascularized 3D-printed model biological microenvironment configured to recapitulate intravasation and tumor cell vascular extravasation during metastasis. FIGS. 38A-41B illustrate an example vascularized 3D-printed model biological microenvironment configured to recapitulate effects of a drug, other compound, or type of cell introduced via the model conduit on cells or compounds positioned within the 3D-printed biological environment outside of the conduit. Although these example 3D-printed model biological microenvironments are described in the context of tumor cells and aspects of cancer metastasis, such examples may be adapted to other biological phenomena.

FIGS. 10-21 illustrate an example 3D-printed directional cell migration chamber.

Figure 10:
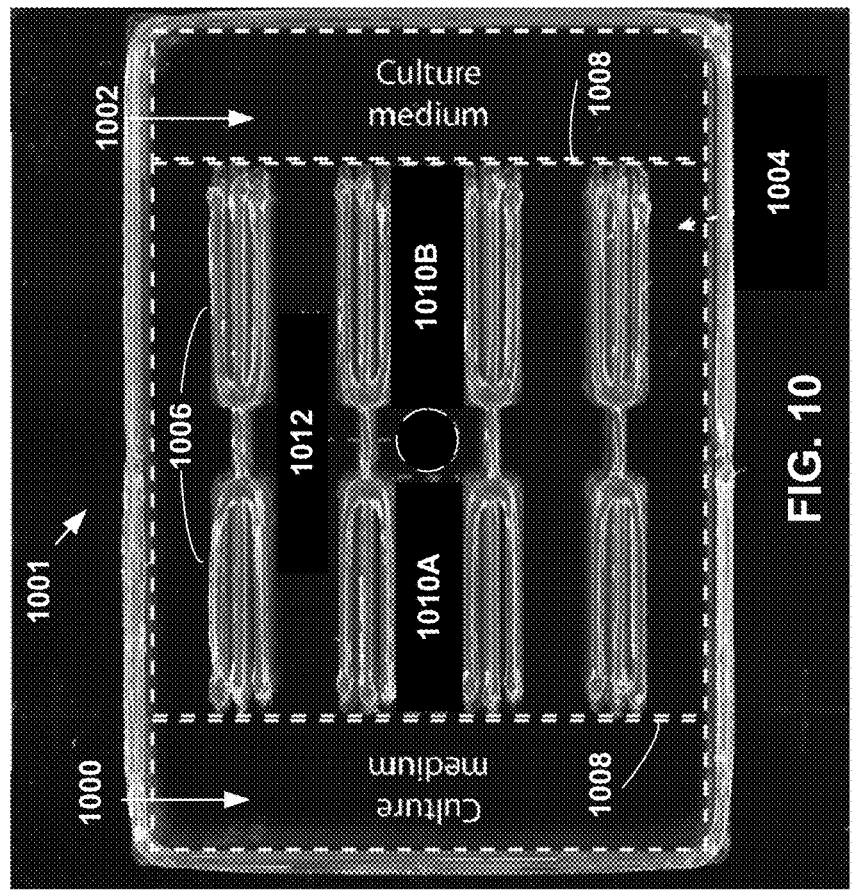
FIG. 10 is a digital image of an example 3D-printed directional cell migration chamber in accordance with examples of this disclosure.

FIG. 10 is a digital image of an example 3D-printed directional cell migration chamber in accordance with examples of this disclosure. The 3D-printed directional cell migration chamber of FIG. 10 is an example 3D-printed model biological microenvironment in accordance with examples of this disclosure. In some examples, a 3D-printed model biological microenvironment 1001 may include a platform (e.g., a silicone scaffold) configured in a substantially rectangular shape, although other shapes may be used. The 3D-printed model biological microenvironment may include a chamber 1000, 1002 containing cell culture medium at each of two opposite ends of the chamber (i.e., Chamber I 1000 and Chamber II 1002 in FIG. 10). A gel matrix 1004 (e.g., of fibrin gel, GelMa, or other suitable gel) may be 3D-printed onto the silicone scaffold. In some examples, such examples in which the 3D-printed model biological microenvironment 1001 is a directional cell migration chamber, the silicone scaffold and/or the gel matrix may include one or more "forks" 1006 formed therein, although in other examples such forks 1006 may not be included. The forks 1006 may help retain the configuration of the cell migration chamber 1001, and may extend at least partway between Chamber I 1000 and Chamber II 1002. The forks 1006 may define discrete flow-constrained regions therebetween within the cell migration chamber 1001, which may constrain a biomolecular gradient and associated cell migration to individual ones of such regions. In some examples, such flow-constrained regions may enable multiplexing of assays (e.g., cell-migration assays) within one directional cell migration chamber or other 3D-printed model biological microenvironment.

Programmable-release capsules may be 3D-printed into the gel matrix 1004 of the directional cell migration chamber 1001, such as within a discrete region defined by two forks 1006 or by a fork 1006 and a sidewall 1008 of the chamber. For example, capsules 1010 containing a biomolecule or other chemical of interest capable of forming a gradient within the gel matrix 1004 (e.g., EGF) may be 3D-printed in a region between two forks 1006 toward Chamber II 1002, as in the example of FIG. 10. Control capsules 1010A (i.e., capsules containing a non-bioactive compound) may be 3-D printed in a region between the two forks 1006 toward Chamber I 1000. In some examples, a cell droplet 1012 (e.g., a tumor cell droplet) may be positioned, such as by 3D printing, pipetting, or other methods of placement, between the capsules 1010A and 1010B containing the chemical of interest 1010B and the control capsules 1010A. Rupture of the capsules 1010 containing the chemical of interest 1010B may establish a chemical depot of the chemical of interest toward Chamber II 1002, and rupture of the control capsules 1010A may establish a gradient of the non-bioactive compound contained therein toward Chamber I 1000, as discussed below with respect to FIG. 11.

Figure 11:
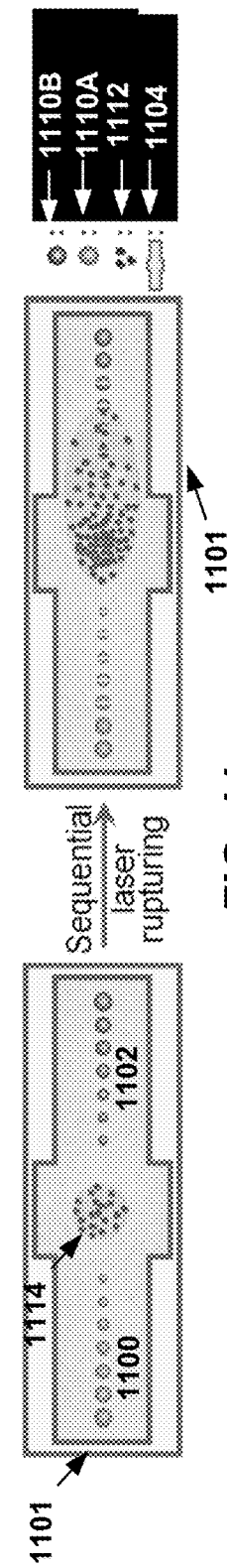
FIG. 11 is a graphical representation of cancer cell migration in an example directional cell migration chamber following sequential laser rupturing of programmable-release capsules in accordance with examples of this disclosure.

FIG. 11 is a graphical representation of cancer cell migration in an example directional cell migration chamber following sequential laser rupturing of programmable-release capsules in accordance with examples of this disclosure. In some examples, one or more aspects of the directional cell migration chamber 1101 of FIG. 11 may be substantially similar to the cell migration chamber of FIG. 10, such as the positioning of capsules 1110A and 1110B containing the chemical of interest, control capsules, tumor cell droplet 1112, and culture-medium chambers 1100 and 1102. In the example of FIG. 11, the chemical of interest contained within some of the capsules 1110B is EGF.

As illustrated in FIG. 11, sequential laser rupturing of the EGF-containing capsules 1110B may establish an EGF gradient extending through the right side of the cell migration chamber 1100 toward the culture-medium chamber 1102 on the right-hand end. Rupture of the control capsules 1110A may establish a gradient of the non-bioactive compound extending through the left side of the cell migration chamber 1100 toward the culture-medium chamber 1102 on the right-hand end. Tumor cells 1112 from the tumor cell droplet 1114 may migrate into the EGF gradient and toward the culture-medium chamber 1102 on the right-hand end, but substantially not into the gradient of the non-bioactive compound.

This outcome illustrates that the directional cell migration chambers 1100 and 1102 described herein may enable identification of compounds that may act as chemoattractants to cells (e.g., EGF), to certain types of cells such as cancer cells 1112. In some examples, the identification of such compounds may help enable determinations of prognosis (e.g., the extent to which tumor cells from a patient migrate in response to a compound, which may help predict disease progression), and in some examples may help inform decisions regarding treatments.

Figure 12A:
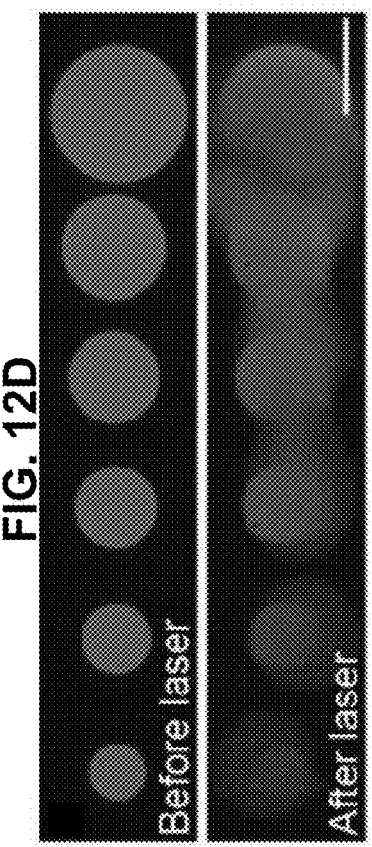
FIG. 12A is a graphical representation of laser-triggered release of growth factors from an example programmable-release capsule in accordance with examples of this disclosure.

FIGS. 12A-12E illustrate growth factor gradients generated by 3D-printed programmable release capsules within a fibrin gel matrix. FIG. 12A is a graphical representation of laser-triggered release of growth factors from an example programmable-release capsule in accordance with examples of this disclosure. FIG. 12A illustrates printed programmable release capsules 1200 triggered by a near-infrared (NIR) laser 1202 that were used to both temporally and spatially create gradients of chemotactic agents. EGF, a chemoattractant of carcinoma cells, was encapsulated to test the feasibility of spatiotemporal control of payload release from the gelatin methacrylate (GelMA) hydrogel-based core/shell capsules. Natural fibrin hydrogel was chosen as the 3D matrix due to its biocompatibility and biodegradability, allowing cells to remodel their own extracellular microenvironments.

Figure 12B:
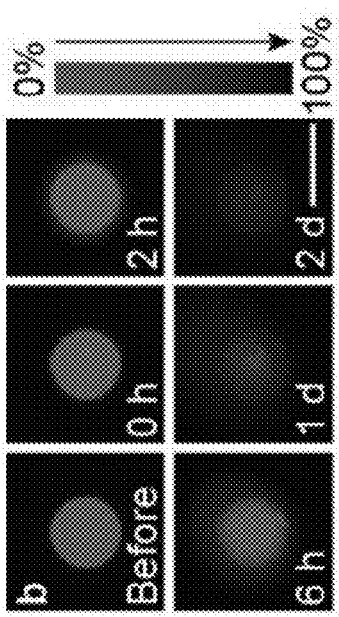
FIG. 12B is a time-lapse fluorescence images showing gradual release of Texas red-labelled EGF from a single example programmable-release capsule in accordance with examples of this disclosure.
Figure 12C:
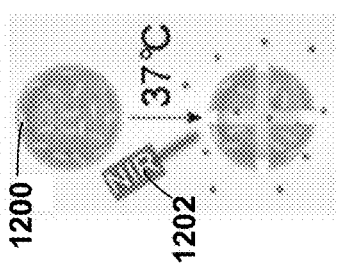
FIG. 12C is graphical representation of release of EGF from a bare core, a ruptured programmable-release capsule, and a non-ruptured programmable-release capsule in accordance with examples of this disclosure.

FIG. 12B is a time-lapse fluorescence images showing gradual release of Texas red-labelled EGF from a single example programmable-release capsule in accordance with examples of this disclosure. FIG. 12C is graphical representation of release of EGF from a bare core, a ruptured programmable-release capsule, and a non-ruptured programmable-release capsule in accordance with examples of this disclosure. The laser-triggered progression of gradual EGF (Texas red-labeled) release from a single capsule over a 2-day period within the fibrin gel is shown in FIG. 12B and quantitated by the time-dependent decrease of fluorescence intensity within the capsule as illustrated by the middle curve of FIG. 12C. The capsules preserved growth factor payload within the polymer shell before laser rupture (lowest curve). Compared to payload release from bare cores (highest curve), a low level of passive leakage was detected from capsules, which may be due to slow hydrolysis of the poly(lactic-co-glycolic) acid (PLGA) shell within the hydrogel matrix.

Figure 12D:
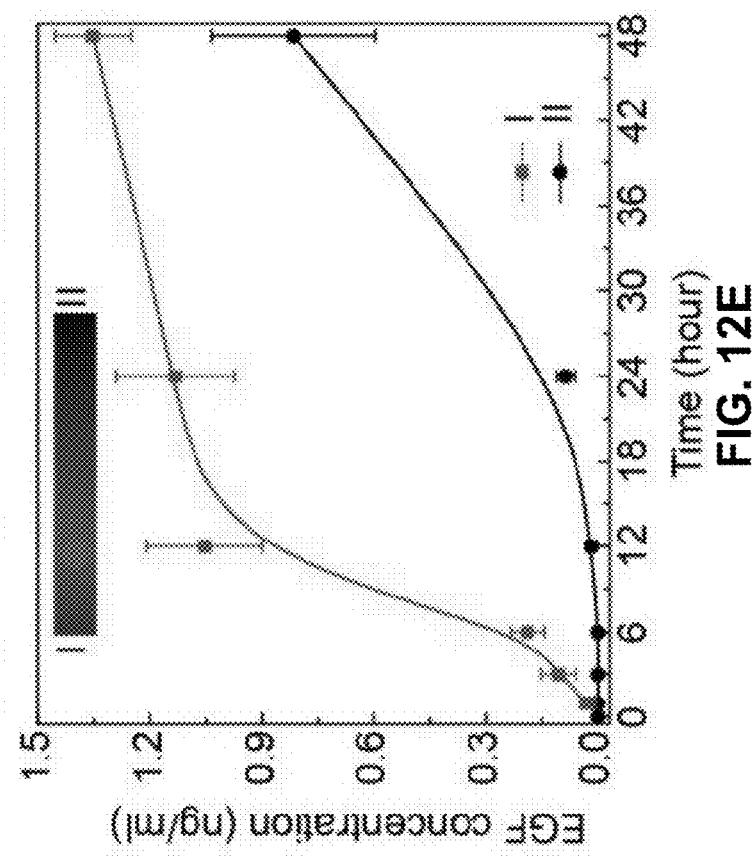
FIG. 12D is fluorescence images of an example array of Texas Red-labeled EGF capsules before and after laser irradiation in accordance with examples of this disclosure.

FIG. 12D is fluorescence images of an example array of Texas Red-labeled EGF capsules before and after laser irradiation. To demonstrate spatial control with the capsules, arrays of cores containing varying volumes were 3D printed. FIG. 12D shows a representative linear array of EGF capsules with 750 µm center-to-center spacing covered by a fibrin gel. The volumes of the printed capsules were controlled with nanoliter resolution via tuning the dispensing time. Capsules were sequentially ruptured using a near infrared (NIR) laser. Fluorescence images of FIG. 12D and brightfield images of FIG. 13A (discussed below) show that individual capsules may be precisely triggered, demonstrating high resolution spatial control over payload release.

Figure 12E:
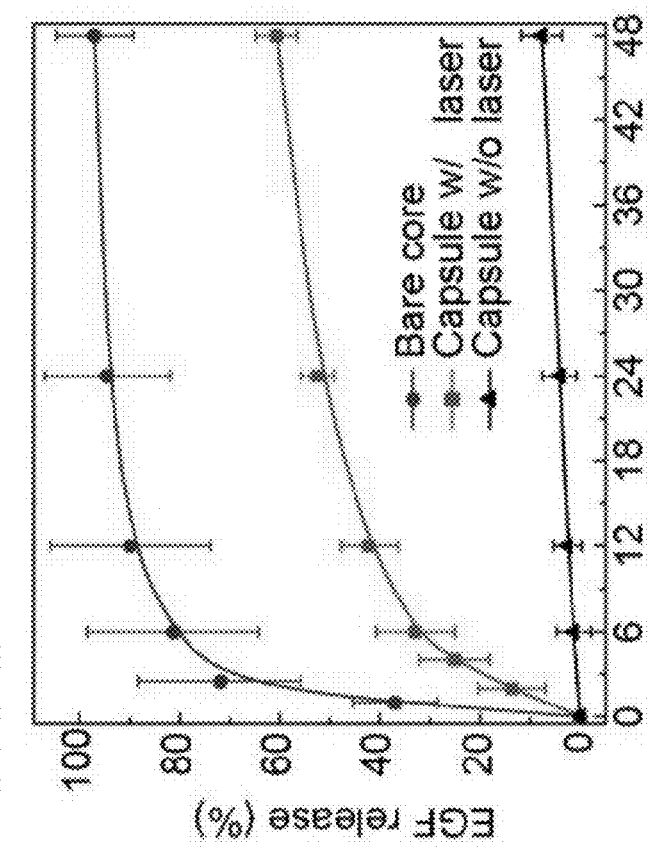
FIG. 12E is a graphical representation of EGF concentration measured in Chamber I (3 millimeter (mm) to the EGF capsule, upper line) and Chamber II (9 mm to the EGF capsule, lower line) of the example cell migration chamber of FIG. 10 vs time, illustrating that released growth factors may form and retain a chemical depot within a 3D fibrin gel.

FIG. 12E is a graphical representation of EGF concentration measured in Chamber I (3 mm to the EGF capsule, upper line) and Chamber II (9 mm to the EGF capsule, /lower line) of the example cell migration chamber of FIG. 10 vs time. Due to the impracticality of non-invasively performing an accurate assessment of molecular concentration within the fibrin gel, built-in Chamber I and Chamber II were included in the directional cell migration chamber of FIG. 10, which enabled independent measurement of the levels of EGF that collected in the culture medium contained in the chambers. As illustrated in FIG. 12E, the level of EGF detected in Chamber I (closer to the capsule) remained higher than in Chamber II (further away), after laser-rupturing the printed capsule.

Figure 13A:
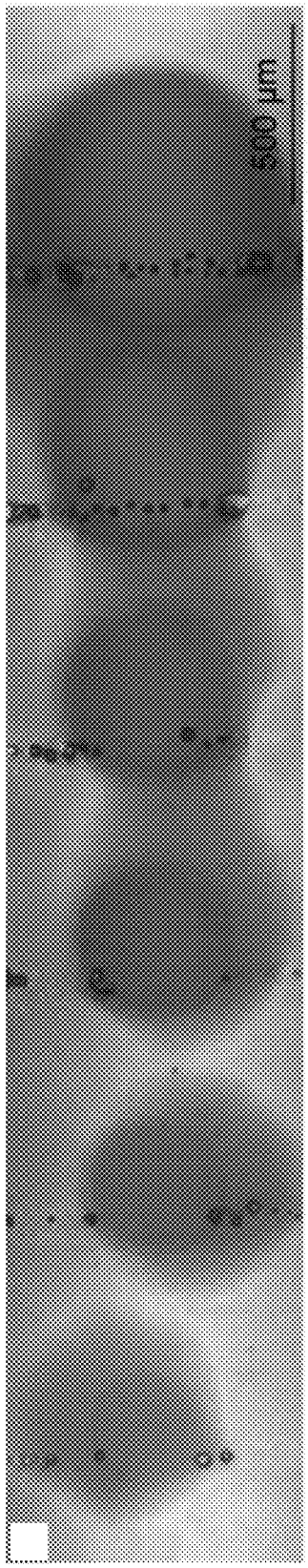
FIG. 13A is a brightfield image of a linear array of example Texas red-labeled epidermal growth factor (EGF) programmable-release capsules of FIG. 12E 6 hours after laser irradiation in the example cell migration chamber of FIG. 10.

FIG. 13A is a brightfield image a linear array of example Texas red-labeled EGF programmable-release capsules of FIG. 12E 6 hours after laser irradiation in the example cell migration chamber of FIG. 10. In the example of FIG. 13A, the capsules have a center-to-center spacing of 750 µm and are shown 6 hours after laser irradiation (linear traces show the course of the MR laser, which indicate precisely placed laser-triggered rupture of individual capsules).

Figure 13B:
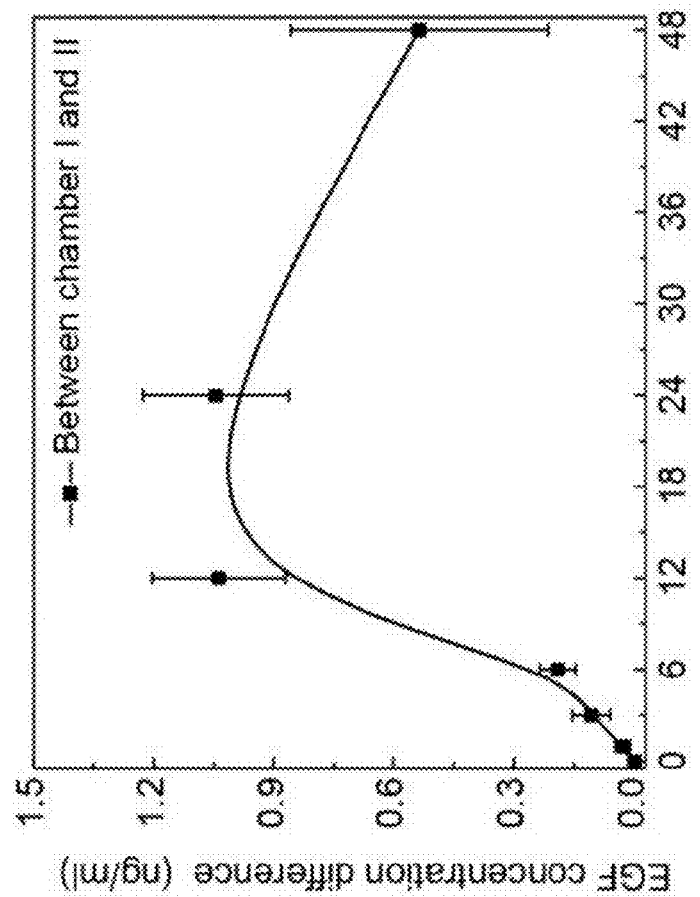
FIG. 13B is a graphical representation of an EGF gradient generated from the rupture of a single example programmable-release capsule in the example cell migration chamber of FIG. 10.

FIG. 13B is a graphical representation of an EGF gradient generated from the rupture of a single programmable-release capsule in the example cell migration chamber of FIG. 10. The plot of FIG. 13B illustrates EGF concentration difference between chamber I and chamber II vs time, after laser-triggered rupture of the EGF capsule, showing an EGF gradient was generated and maintained for a 2-day period (mean±s.d., n=4 per group). The plot of FIG. 13B illustrates a substantial difference that was observed 6 h after release of EGF and was maintained until at least 48 h, which indicates the generation of an EGF gradient within the fibrin gel. In some examples, progressive molecule release at a moderate rate and/or relatively slow diffusion within the gel may contribute to the retention of this gradient. Thus, by combining advantages of both temporal and spatial manipulation of molecular gradients, these 3D-printed programmable release capsules may provide an approach to chemically reconstruct dynamic extracellular microenvironments in 3D hydrogel matrices.

FIG. 14 is a graphical representation of directional migration of tumor cells under the guidance of EGF gradients generated by 3D-printed programmable-release capsules in accordance with examples of this disclosure, illustrating guided tumor cell migration via chemotaxis. The graphical representation of FIG. 14 illustrates the directional migration of tumor cells 1400 under the guidance of EGF gradients generated by 3D-printed capsules 1402 and 1404, which indicates that the EGF gradients generated by EGF released from the capsules 1404 following capsule rupture via irradiation may be used to guide tumor cell migration 1406, an important step in metastasis.

In the example experiment illustrated in FIG. 14, a droplet of fibrin loaded with GFP-A549 lung cancer cells 1400 was printed between linear arrays of chemoattractant capsules 1404 (right) and blank control capsules 1402 (left). The printed droplet defined the primary site of the tumor cells 1400. To generate a long-lasting EGF gradient, capsules 1402 and 1404 were ruptured sequentially at 2-day intervals, starting with the capsule 1408A closest to the cell 1400. Concomitantly, a corresponding control capsule 1408B was also ruptured. The resulting EGF gradient and GFP-A549 response to the gradient is discussed below with respect to FIGS. 15A-17.

Figure 15A:
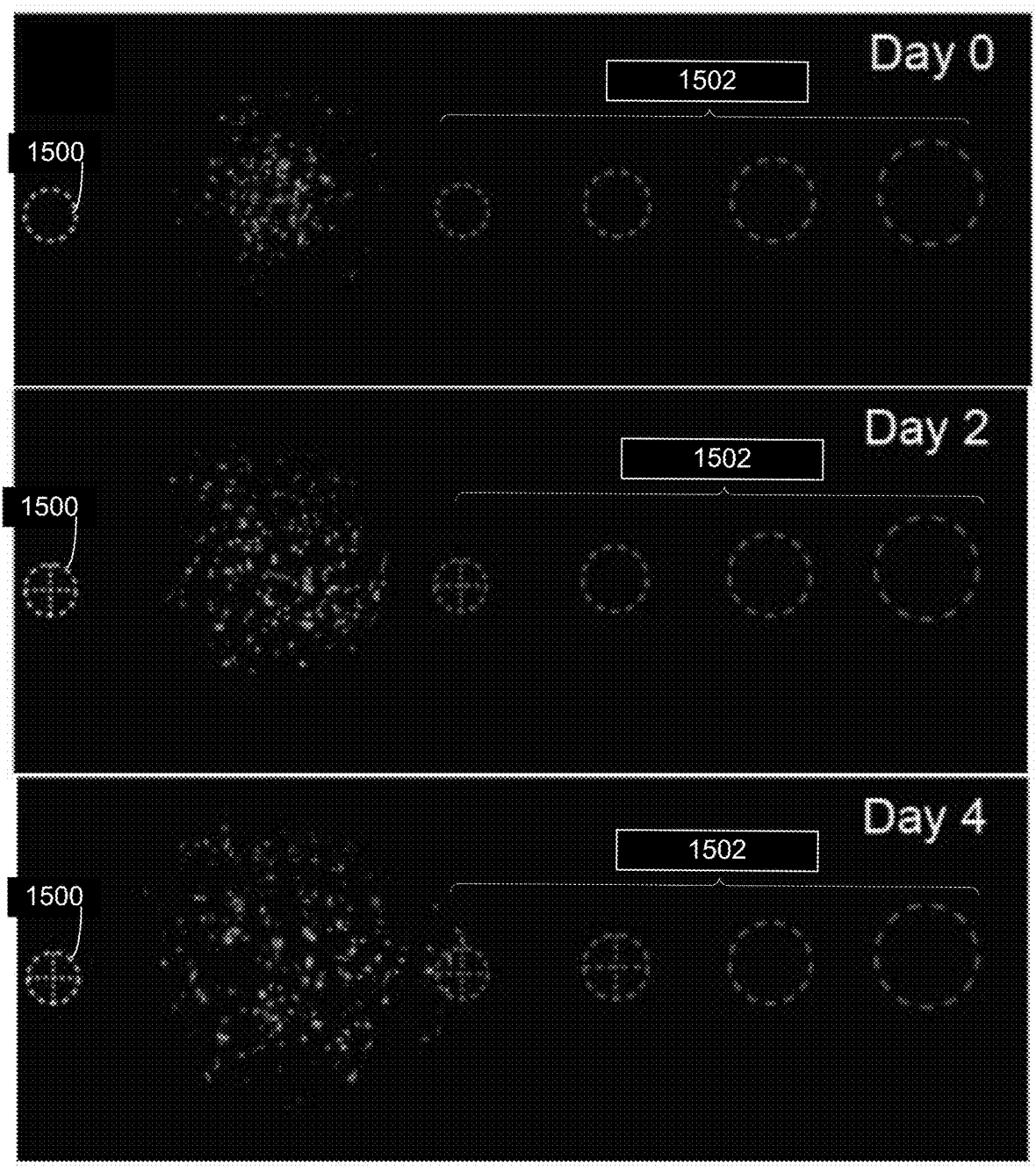
FIG. 15A is panoramic fluorescence images illustrating distribution of green fluorescent protein (GFP)-expressing A549 cells over time during days 0-4 post-laser rupture of example EGF-containing programmable-release capsules within an example cell migration chamber in accordance with an example of this disclosure.
Figure 15B:
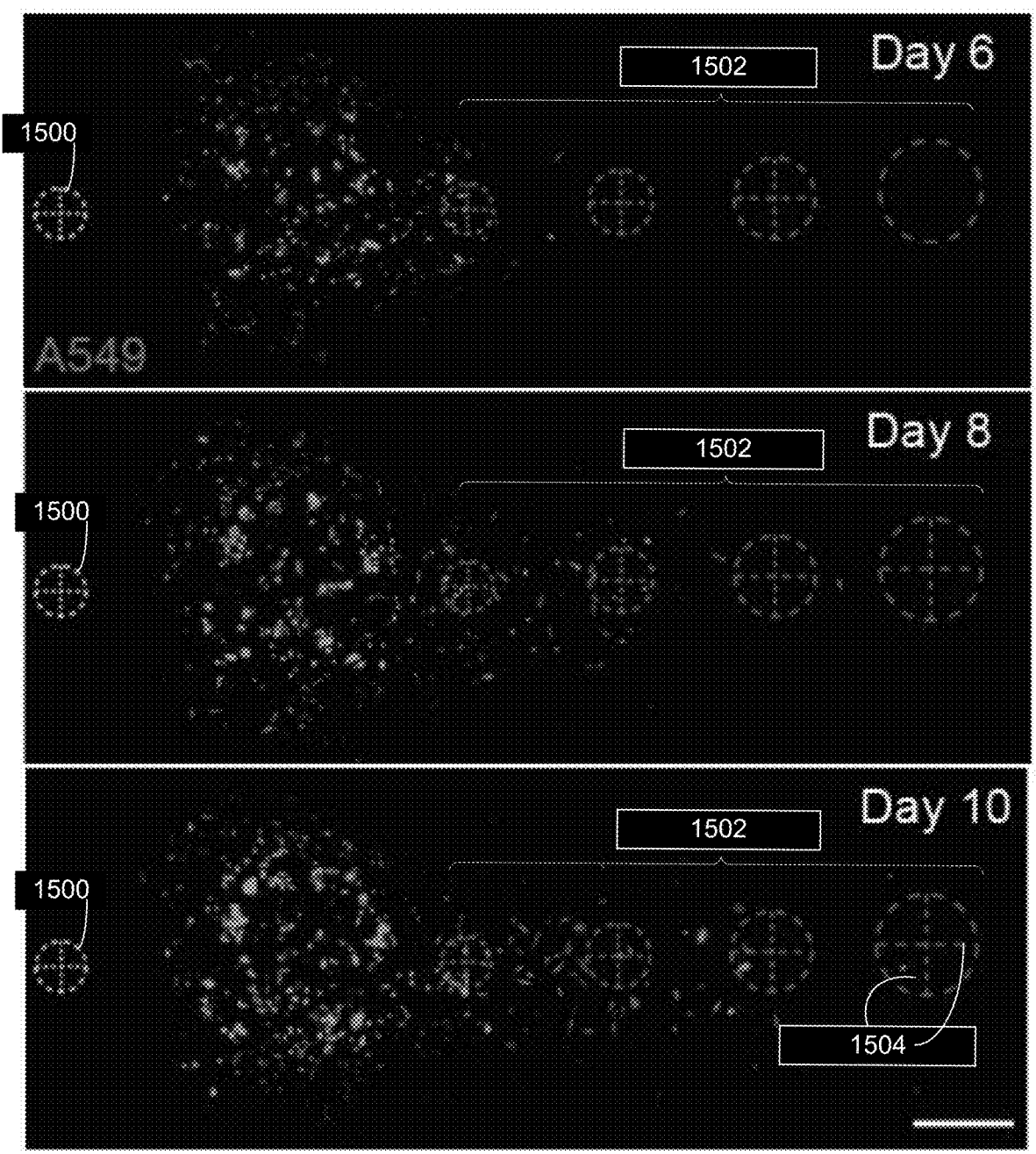
FIG. 15B is panoramic fluorescence images illustrating distribution of GFP-expressing A549 cells over time during days 6-10 post-laser rupture of the EGF-containing programmable-release capsules of FIG. 15A.
Figure 15C:
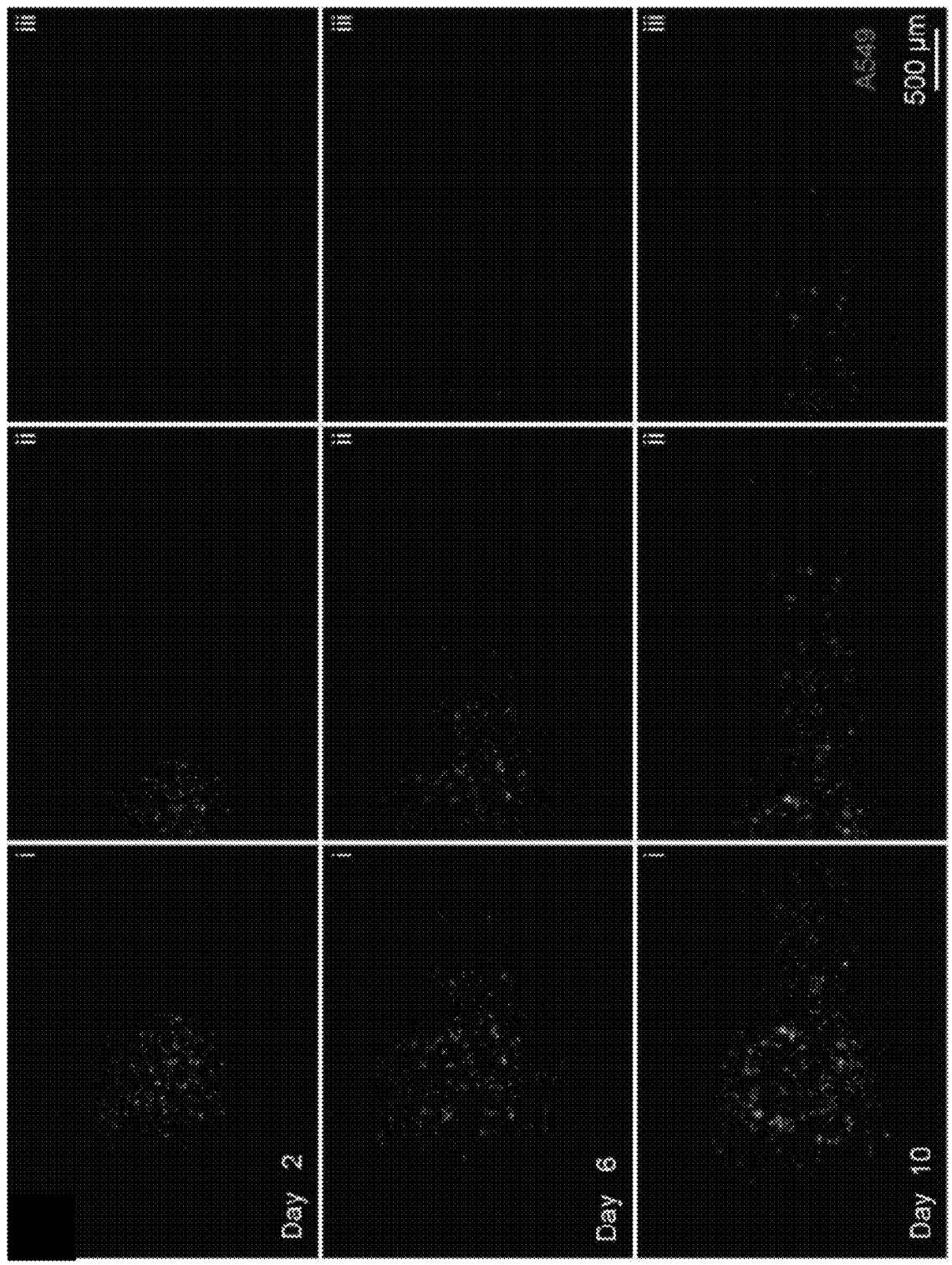
FIG. 15C is a series of mono-view fluorescent field images of the GFP-expressing A459 cells of FIGS. 15A and 15B on days 2, 6, and 10.

FIG. 15A is panoramic fluorescence images illustrating distribution of GFP-expressing A549 cells over time during days 0-4 post-laser rupture of example EGF-containing programmable-release capsules within an example cell migration chamber in accordance with an example of this disclosure, demonstrating guided migration of the A549 cells. FIG. 15B is panoramic fluorescence images illustrating distribution of the GFP-expressing A549 cells of FIG. 15A over time during days 6-10 post-laser rupture of the EGF-containing programmable-release capsules of FIG. 15A. The circle 1500 at the left-hand side of each of the images corresponding to days 0, 2, 4, 6, 8, and 10 illustrates position of ruptured control capsules that did not contain EGF. The four circles 1502 to the right of the left-hand circle in each of the images illustrate the position of ruptured capsules that contained EGF. The cross lines 1504 in each of the circles illustrates the laser rupture pathways. FIG. 15C is a series of mono-view fluorescent field images of the GFP-expressing A459 cells of FIGS. 15A and 15B on days 2, 6, and 10.

By comparing the cell distributions at each time point in FIGS. 15A and 15B, three main observations describe the cellular activities: (i) increased proliferation; (ii) expansion in space; and (iii) directional movement. Most of the escaped cells were only found in the EGF capsule region and increased in number as more EGF capsules were ruptured, presenting guided cell migration. A parallel control experiment without laser rupture revealed that most of the A549s remained within the original site without any directional migratory behavior, as discussed below with respect to FIG. 19.

Figure 16:
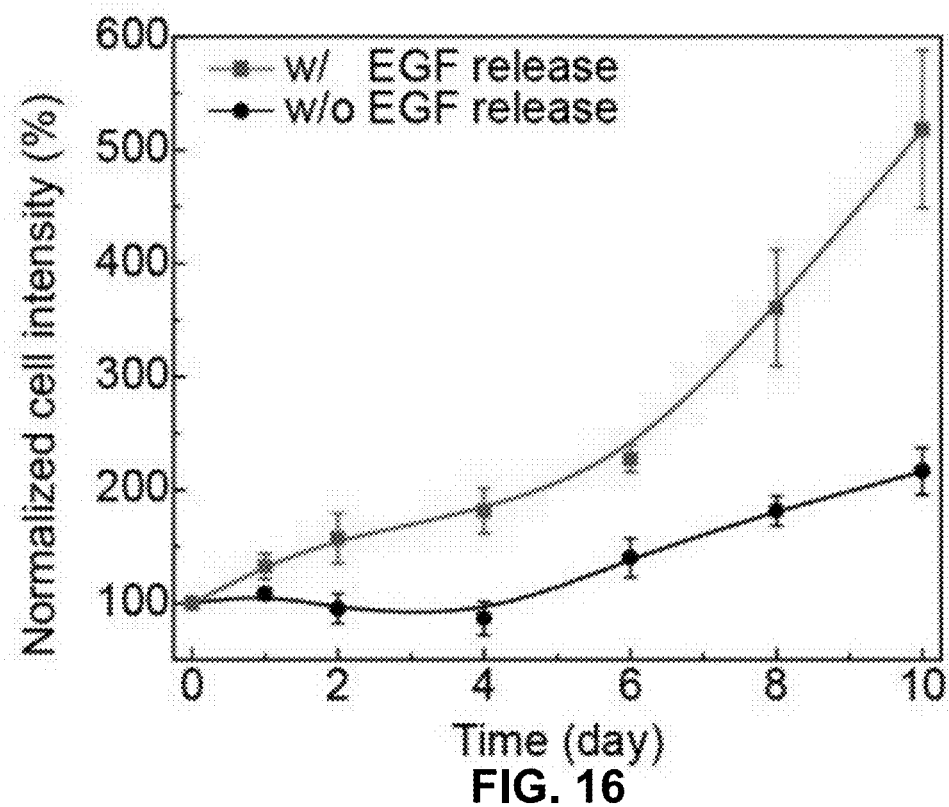
FIG. 16 is a graphical representation of cellular fluorescence intensity of example EGF-expressing A549 cells vs time, with and without EGF release from example programmable-release capsules within a cell migration chamber in accordance with examples of this disclosure.

FIG. 16 is a graphical representation of cellular fluorescence intensity of example EGF-expressing A549 cells vs time, with and without EGF release from example programmable-release capsules within a cell migration chamber in accordance with examples of this disclosure. The plots of cellular fluorescence intensity of A549s (normalized by intensity at day 0 before capsules were ruptured) vs time, is illustrated with EGF release (upper line) and without EGF release (lower line), demonstrating the influence of EGF on cellular proliferation (mean±s.d., n=4 per group). The cellular growth rates were first quantitatively compared between samples with and without laser-triggered release of EGF by directly analyzing the fluorescence intensity of GFP-expressing cells. As illustrated in FIG. 16, the growth of tumor cells was accelerated in response to released EGF consistent with previous reports. The migratory behavior was further quantified by tracking the positions of individual A549 cells or clusters, as discussed below with respect to FIG. 18.

Figure 17:
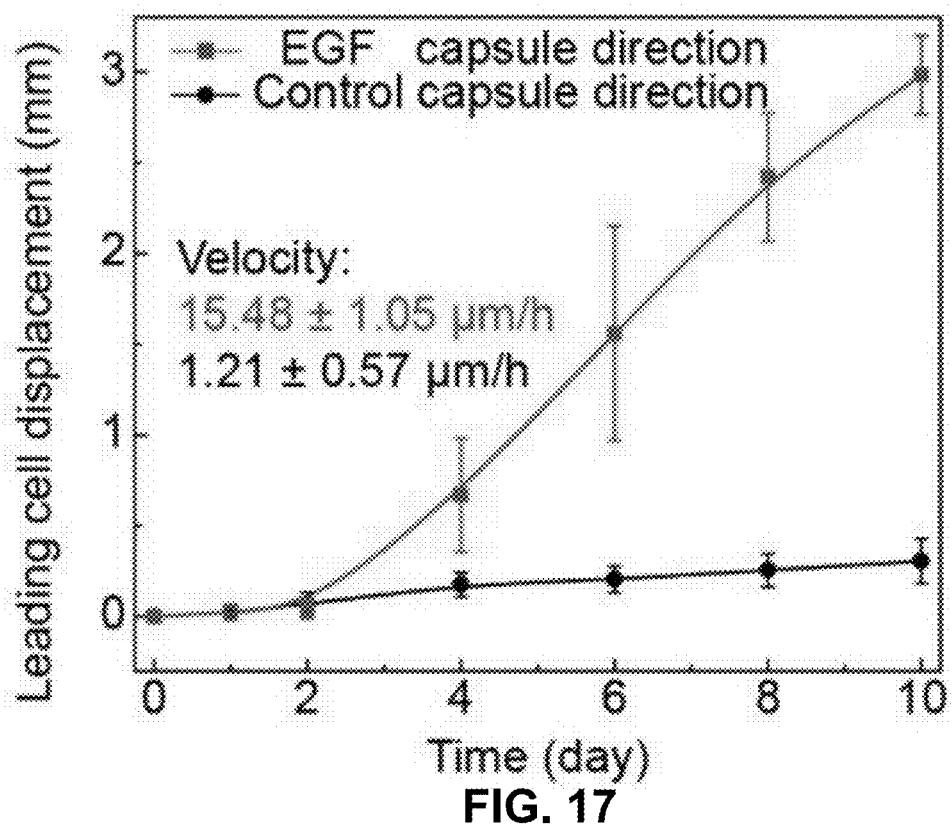
FIG. 17 is a graphical representation of directional migration of the A549 cells of FIG. 16 toward EGF following laser rupture of the EGF-containing programmable-release capsules in the cell migration chamber used in the example of FIG. 16.

FIG. 17 is a graphical representation of directional migration of the A549 cells of FIG. 16 toward EGF following laser rupture of the EGF-containing programmable-release capsules in the cell migration chamber used in the example of FIG. 16. To show that the migration was guided and directional, the horizontal travel distance of leading cells over time was calculated. The plots of the displacement of leading A549 cells (only the distance in the x-direction was measured) due to EGF capsule direction (upper line) and control capsule direction (lower line), illustrates the directional migration (mean±s.d., n=4 per group) of the A549 cells. Under the guidance of EGF cues, the maximum cell velocity was 15.48±1.05 µm/h, whereas random movement of cells with a maximum velocity of only 1.21±0.57 µm/h was seen with control capsules. These results indicate that EGF released from the 3D printed capsules not only actively promoted the proliferation of A549 cells, but also guided their migration.

Figure 18:
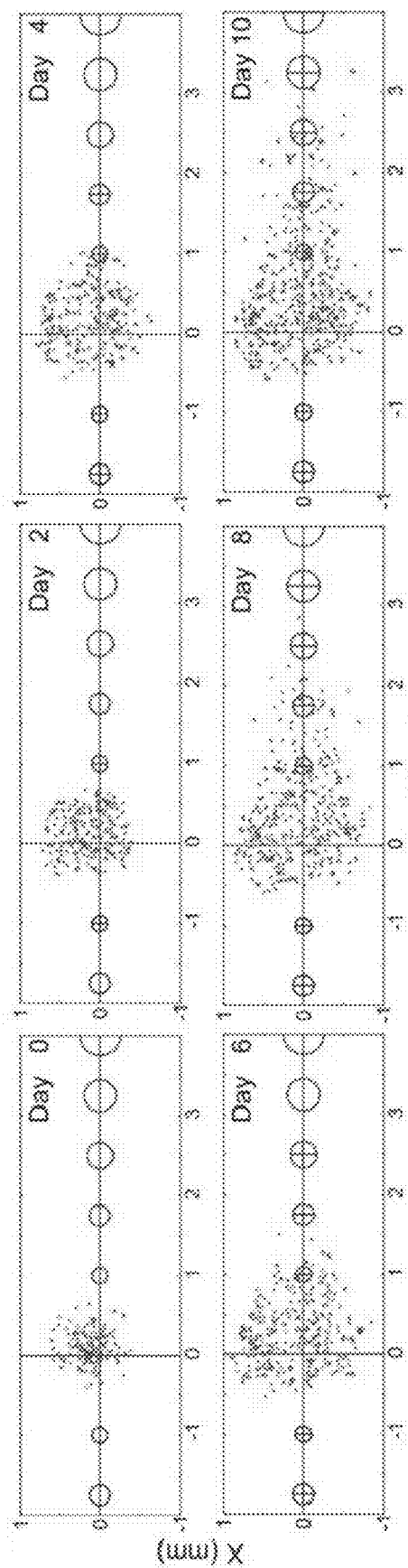
FIG. 18 is a graphical representation quantitatively illustrating the positions of A549s and the programmable-release of EGF from the capsules of FIG. 16 in a coordinate system on days 0, 2, 4, 6, 8, and 10 following laser rupture of the programmable-release capsules.

FIG. 18 is a graphical representation quantitatively illustrating the positions of A549s and the programmable-release of EGF from the capsules of FIG. 16 in a coordinate system on days 0, 2, 4, 6, 8, and 10 following laser rupture of the programmable-release capsules. FIG. 18 illustrates tumor cell migration tracking: plots quantitatively showing the positions of A549s and printed capsules in a coordinate system on days 0, 2, 4, 6, 8, and 10 (dots: A549s; circles on the right-hand side of the center point: EGF capsules; circles on the left-hand side of the center point: control capsules without growth factor payload; cross lines: laser pathways).

Figure 19:
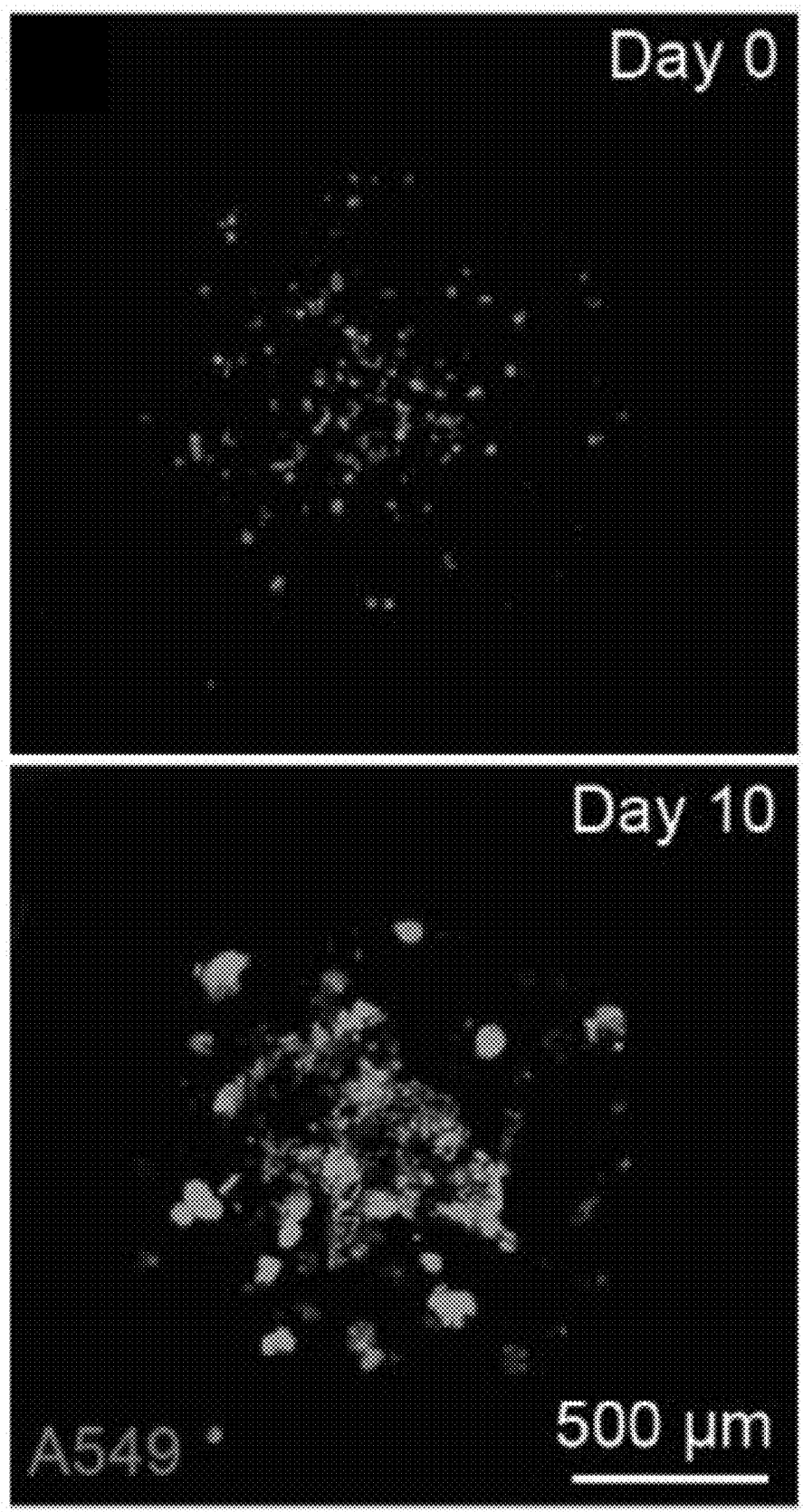
FIG. 19 is fluorescence images showing a distribution and proliferation of GFP-expressing A549s in the absence of release of EGF from example programmable-release capsules on days 0 and 10 in accordance with the examples of this disclosure.
Figure 20:
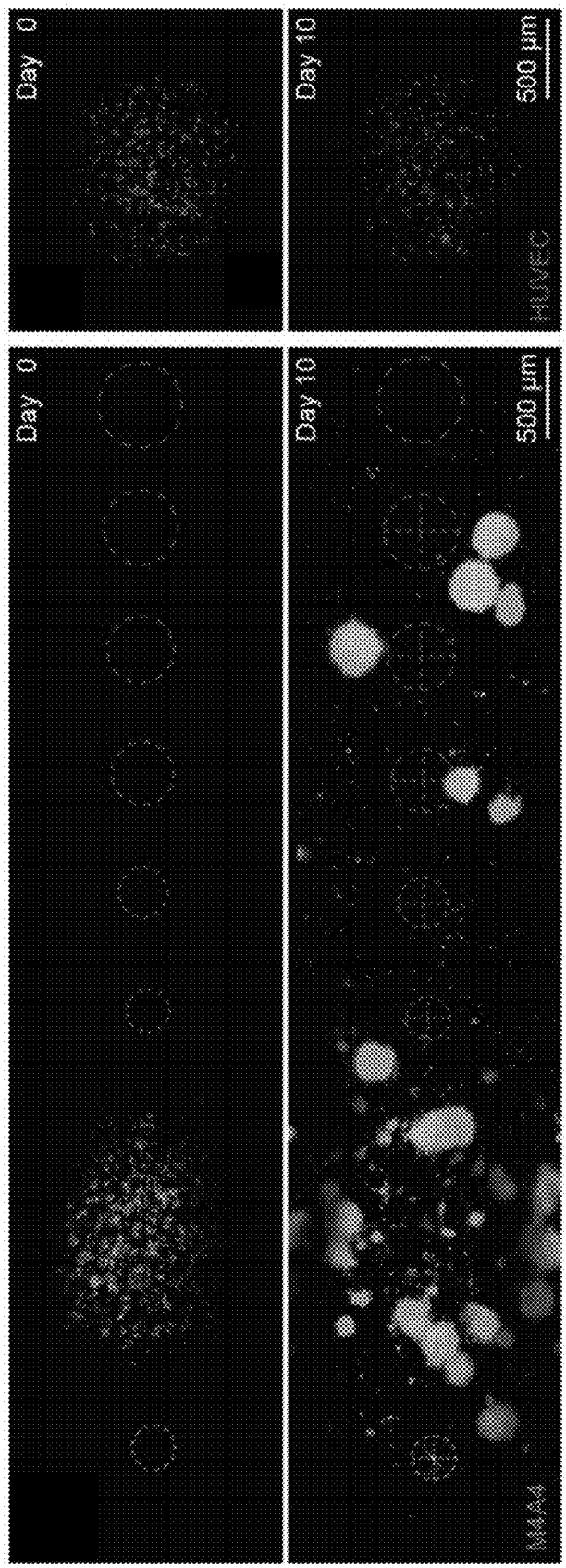
FIG. 20A is panoramic fluorescence images illustrating the distribution of the GFP-expressing M4A4 cells following the programmable release of EGF from EGF-containing programmable release capsules on days 0 and 10 in accordance with examples of this disclosure.
FIG. 20B is fluorescence images illustrating a distribution of red fluorescent protein (RFP)-expressing HUVEC cells with the programmable release of EGF from example programmable-release capsules on days 0 and 10 in accordance with examples of this disclosure.

FIG. 19 is fluorescence images showing a distribution and proliferation of GFP-expressing A549s in the absence of release of EGF from example programmable-release capsules on days 0 and 10 in accordance with the examples of this disclosure. FIG. 19 illustrates a control experiment parallel to the experiment illustrated in FIGS. 15A-15C, in which no EGF-containing capsules were ruptured. In the absence of laser rupture of the EGF-containing capsules, most of the A549s remained within the original site without any directional migratory behavior.

FIG. 20A is panoramic fluorescence images illustrating the distribution of the GFP-expressing M4A4 cells following the programmable release of EGF from EGF-containing programmable release capsules on days 0 and 10 in accordance with examples of this disclosure. FIG. 20B is fluorescence images illustrating a distribution of red fluorescent protein (RFP)-expressing HUVEC cells with the programmable release of EGF from example programmable-release capsules on days 0 and 10 in accordance with examples of this disclosure.

To demonstrate the versatility and selectivity of the 3D-printed directional cell migration chambers described herein, activities of GFP-expressing M4A4 cells (a melanoma cell line) illustrated in FIG. 20A were monitored in parallel with the GFP-expressing A549 cells described above, as well as red fluorescent protein (RFP)-expressing HUVEC cells illustrated in FIG. 20B, in response to EGF capsules sequentially ruptured over 10 days.

Figure 21:
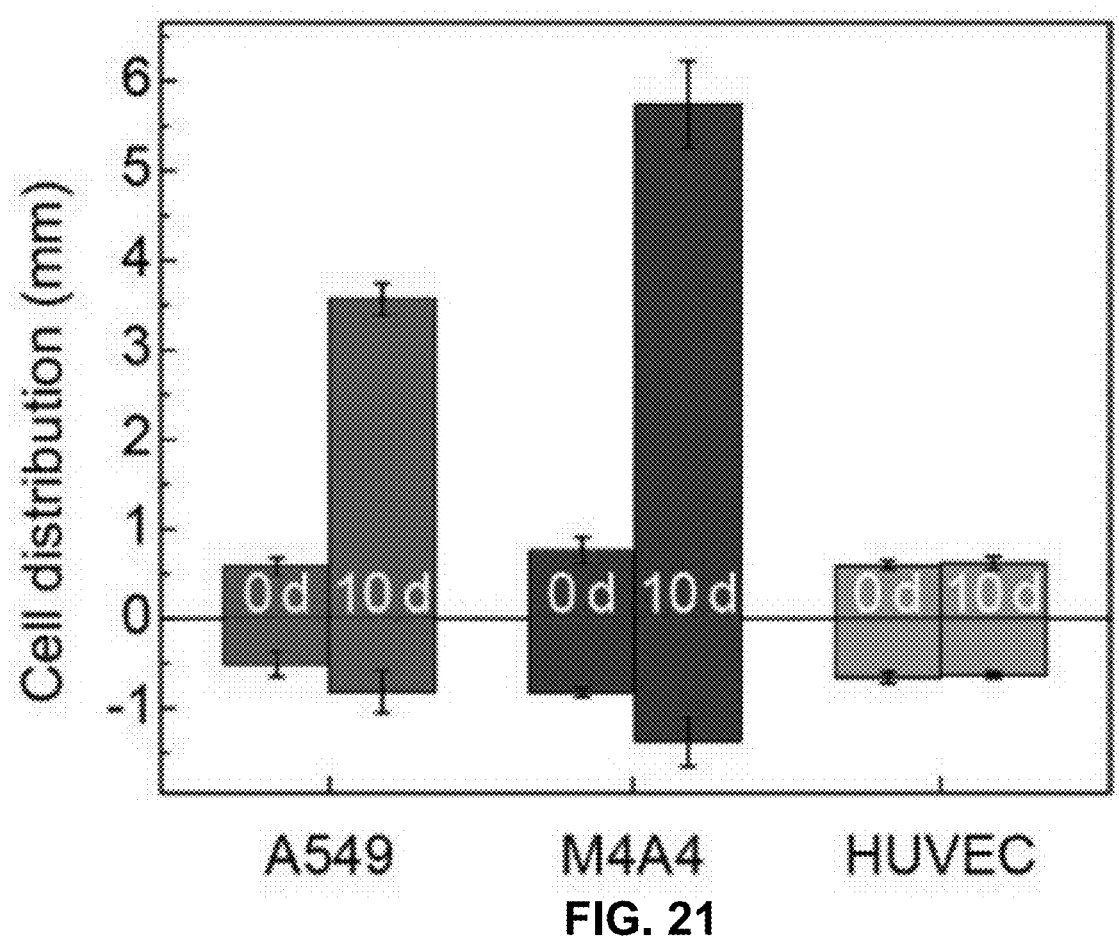
FIG. 21 is a graphical representation of relative selective directed migration of A549 tumor cells, M4A4 tumor cells, and non-tumor HUVEC cells of FIGS. 20A and 20B in response to laser rupture of the EGF-containing programmable release capsules within an example cell migration chamber in accordance with examples of this disclosure.

FIG. 21 is a graphical representation of relative selective directed migration of A549 tumor cells, M4A4 tumor cells, and non-tumor HUVEC cells of FIGS. 20A and 20B in response to laser rupture of the EGF-containing programmable release capsules within an example cell migration chamber in accordance with examples of this disclosure. FIG. 21 illustrates distributions of GFP-A549s, GFP-M4A4s, and RFP-HUVECs on day 10, showing the selective directed migration of tumor cells but not HUVECs (mean±s.d., n=4 per group). Scale bar: 500 µm. Although the M4A4 cells traveled further due to their more aggressive nature, these cells also exhibited directional movement, supporting the versatility of the models and techniques described herein. Specificity was confirmed by the negative migratory response of HUVECs to EGF gradients. These results indicate that the migration of tumor cells may be guided by using 3D printed programmable release capsules as dynamic chemoattractant sources.

FIGS. 22-27 illustrate an example vascularized 3D-printed model biological microenvironment configured to recapitulate vascularized in vivo environments and biological phenomena associated with vasculature, such as tumor cell extravasation during metastasis. For example, together with dynamic chemical environments such as the chemical depots described above, the vascular path, a common route of metastasis, is another significant component of a biomimetic tumor model.

Figure 22:
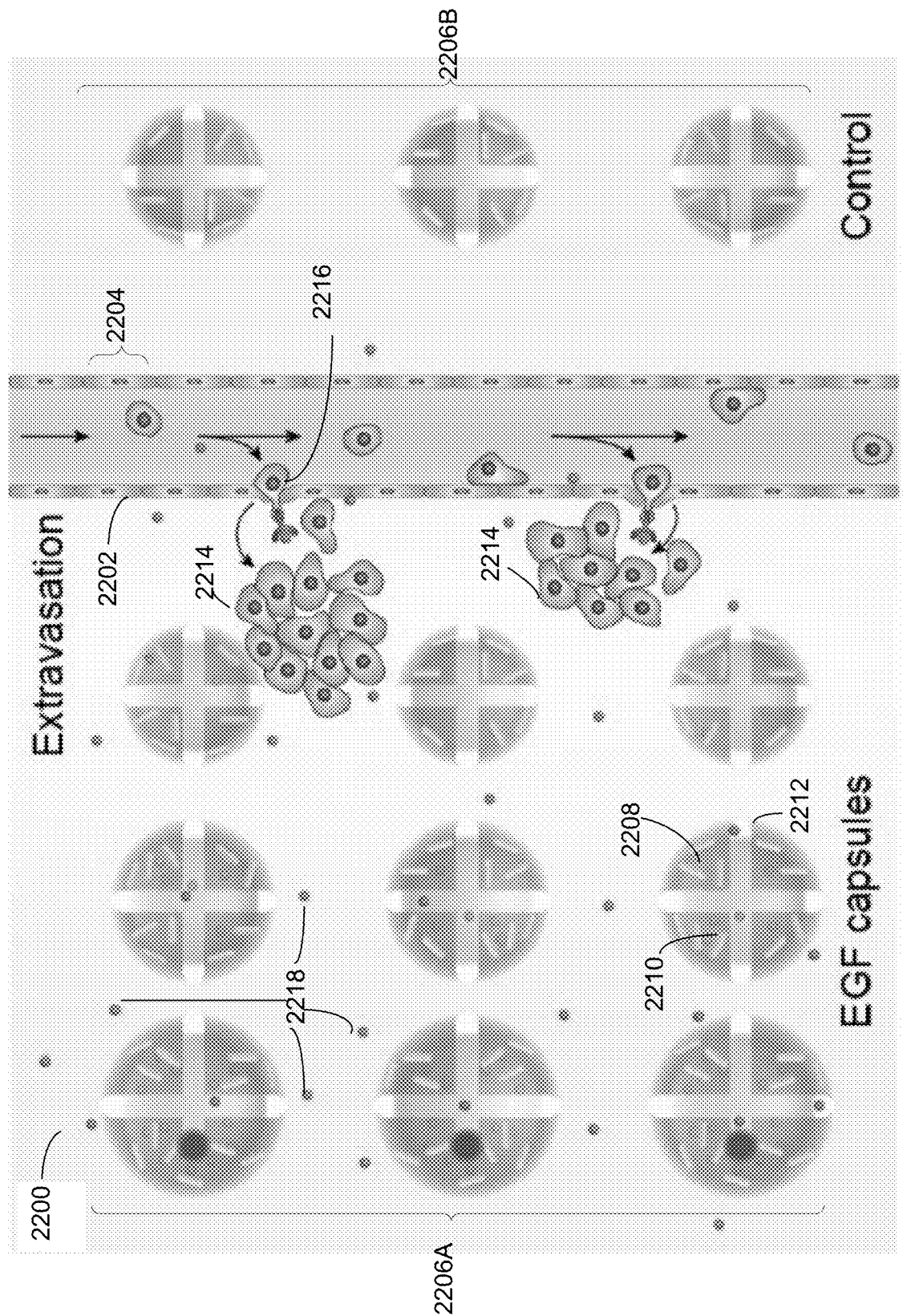
FIG. 22 is a graphical representation illustrating tumor cell extravasation through an endothelial barrier and formation of metastases mediated by EGF gradients in an example vascularized 3D-printed culture chamber configured for cell extravasation testing in accordance with examples of this disclosure.

FIG. 22 is a graphical representation illustrating tumor cell extravasation through an endothelial barrier and formation of metastases mediated by EGF gradients in an example vascularized 3D-printed culture chamber configured for cell extravasation testing in accordance with examples of this disclosure. In some examples, a vascularized 3D-printed culture chamber 2200 may include a model conduit 2202 lined with living cells 2204, as further described below. Such example vascularized 3-D printed culture chambers 2200 may include 3D-printed programmed-release capsules 2206A and 2206B, which may be similar in one or more respects to the capsules described above. For example, capsules in vascularized 3-D printed culture chambers 2200 may include a core 2208 containing a biomolecular payload 2210 (e.g., EGF or other biomolecule) or other chemical, surrounded by a shell 2212 containing LSPR AuNRs or other suitable photothermally reactant components. Such capsules 2206 may be ruptured via laser wavelength, as discussed above. Rupture of the capsules 2206 may create a gradient of the biomolecular or other chemical payload within the vascularized 3D-printed culture chamber 2200, which may affect the behavior of cells within the model conduit (e.g., cause the cells to extravasate) 2202.

As illustrated in FIG. 22, tumor cells 2214 may extravasate through an endothelial barrier 2216 and form metastases in tissue outside of the conduit 2202, such as via mediation by an EGF gradient. As discussed below with respect to FIGS. 23-27, EGF 2218 released from printed capsules 2206 diffused through the endothelial barrier 2216 of an example vascularized 3D-printed culture chamber 2200 in an experiment to induce conduit penetration of A549s and the generation of a metastatic lesion.

Figure 23:
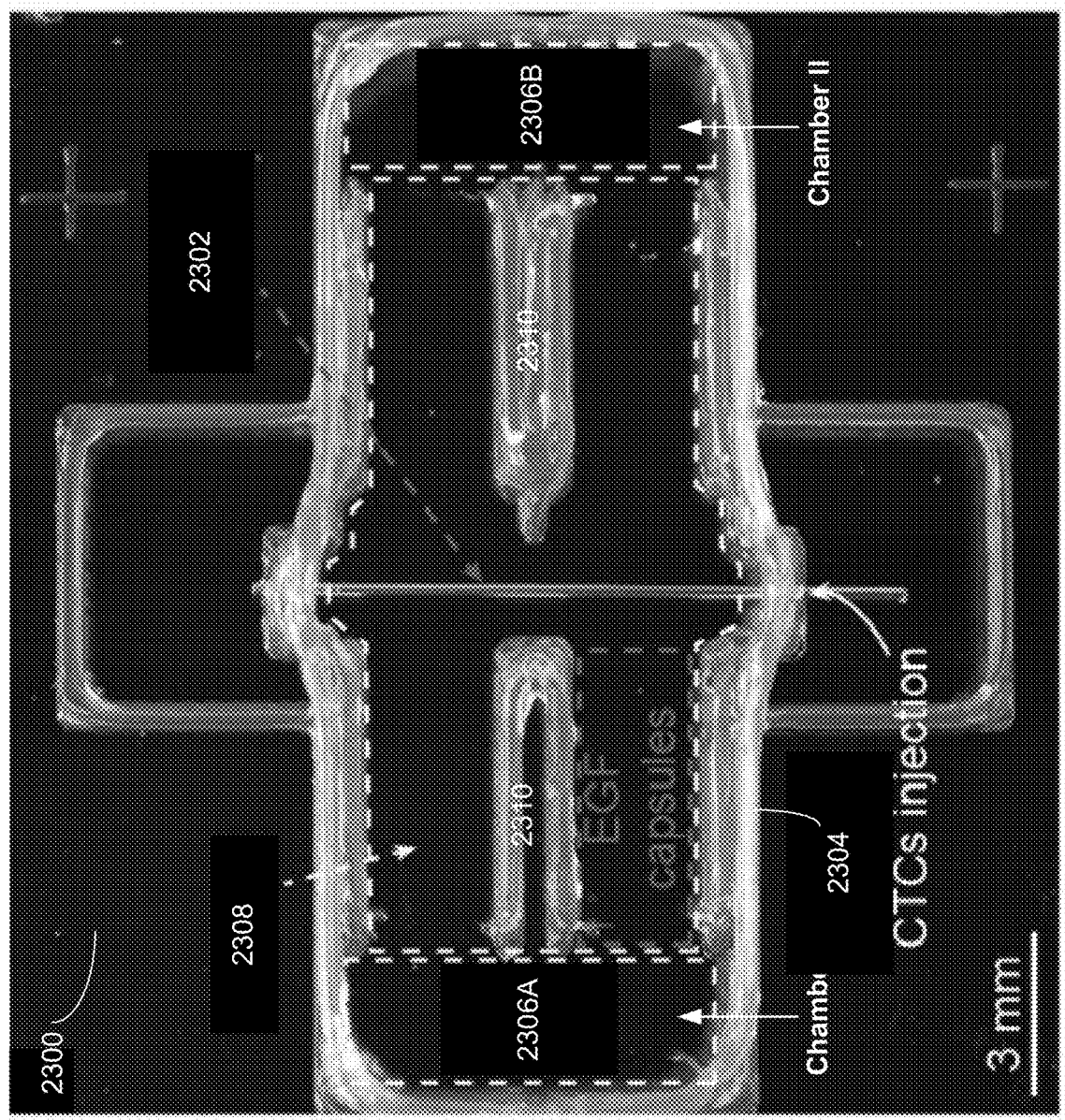
FIG. 23 is a digital image of an example vascularized 3D-printed culture chamber configured for cell extravasation testing in accordance with examples of this disclosure.

FIG. 23 is a digital image of an example vascularized 3D-printed culture chamber configured for cell extravasation testing in accordance with examples of this disclosure. The 3D-printed culture chamber of FIG. 23 is an example vascularized 3D-printed model biological microenvironment 2300 in accordance with examples of this disclosure. Some aspects of the example vascularized 3D-printed culture chamber 2300 of FIG. 23 may be substantially similar to the cell migration chamber of FIG. 10, although the vascularized 3D-printed culture chamber 2300 of FIG. 23 further includes a cultured conduit 2302 extending through the culture chamber 2300, as illustrated in FIG. 23.

In some examples, the 3D-printed culture chamber 2300 of FIG. 23 may include a platform 2304 (e.g., a silicone scaffold) configured in a substantially rectangular or other shape. The 3D-printed culture chamber 2300 may include a chamber containing cell culture medium 2306A and 2306B at each of two opposite ends of the chamber 2300 (i.e., Chamber I and Chamber II in FIG. 23). A gel matrix 2308 (e.g., of fibrin gel, GelMa, or other suitable gel) may be 3D-printed onto the silicone scaffold 2304. In some example vascularized 3D-printed silicone scaffold 2304 and/or the gel matrix 2308 may include one or more "forks" 2310 formed therein, although in other examples such forks 2310 may not be included. The forks 2310 may help retain the configuration of the cell migration chamber 2300 and may extend at least partway between Chamber I 2306A and Chamber II 2306B. The forks 2310 may define discrete flow-constrained regions therebetween within the cell migration chamber 2300, which may constrain a biomolecular gradient to individual ones of such regions. In some examples, such flow-constrained regions may enable establishment of multiple chemical depots within one vascularized 3D-printed model biological microenvironment 2300, which may enable multiplexing of assays and/or development of complex assays involving multiple chemical depots.

The 3D-printed culture chamber 2300 of FIG. 23 further includes a model conduit 2302, which in the illustrated example extends orthogonally to the forks 2310 between the culture medium chambers 2306. The model conduit 2302 may be formed in the fibrin gel 2308 of the 3D-printed culture chamber 2300, and is lined with living HUVEC cells, as further discussed below with respect to FIGS. 24A-24C. Cells (e.g., CTCs), biomolecules, and/or other compounds may be introduced into the model conduit 2302 at either end thereof. As discussed below, cells, biomolecules, and/or other compounds introduced into the model conduit 2302 may circulate through the conduit and may extravasate into the gel matrix 2308 surrounding the conduit 2302. In this manner, model conduits in such example 3D-printed culture chambers 2300 may approximate vascularized in vivo environments.

Figure 24A:
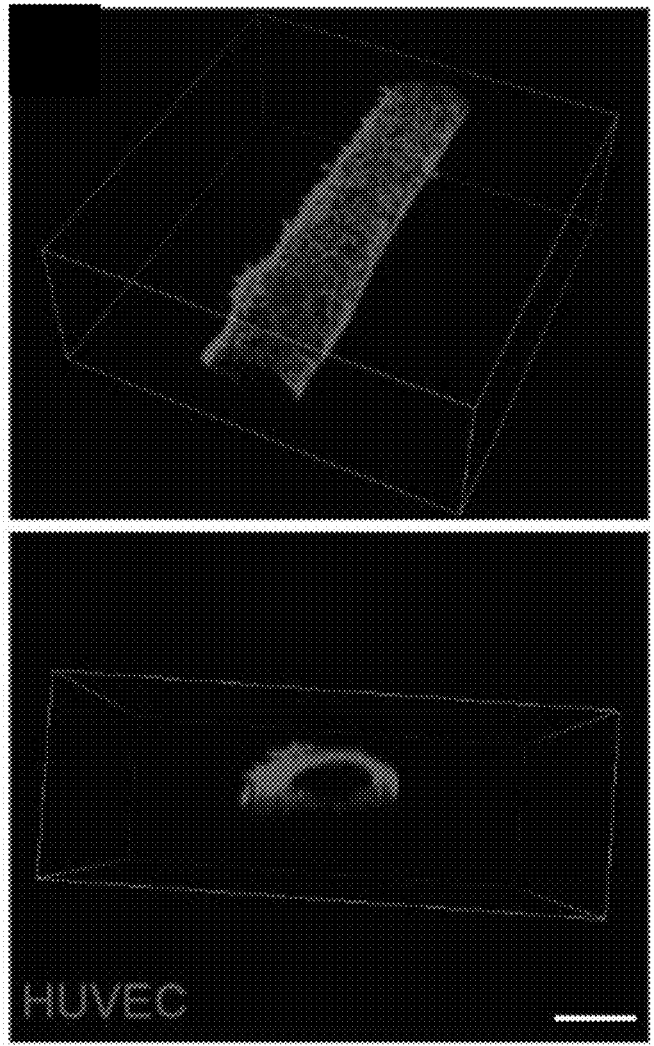
FIG. 24A is confocal images of a top view and a side view of a representative microchannel lined by HUVECs within a fibrin gel in accordance with examples of this disclosure.
Figure 24B:
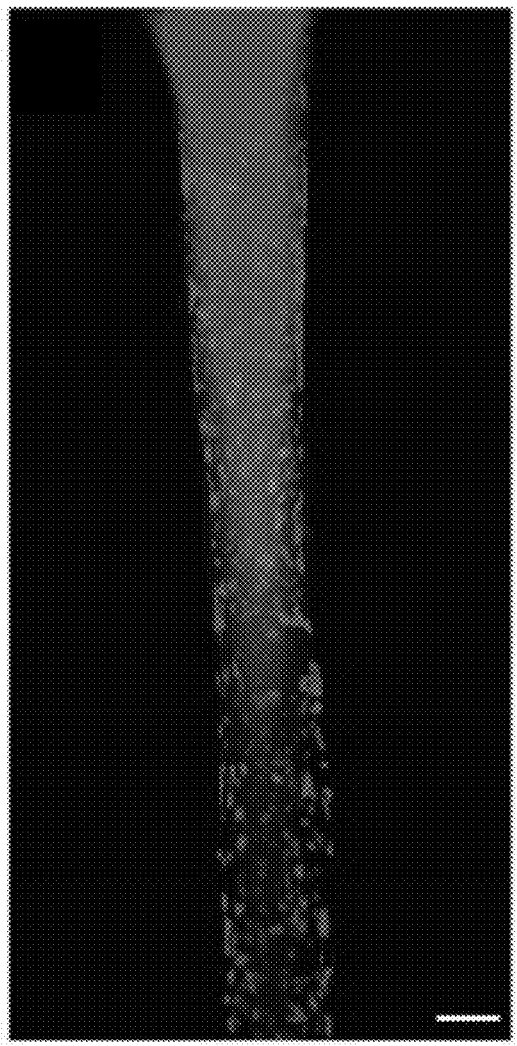
FIG. 24B is a fluorescence image of a representative microchannel lined by HUVECs and perfused by fluorescent fluid in accordance with examples of this disclosure.

FIG. 24A is confocal images of a top view and a side view of a representative microchannel lined by HUVECs within a fibrin gel, such as in the context of the example 3D-printed culture chamber of FIG. 23. FIG. 24B is a fluorescence image of a representative microchannel lined by HUVECs and perfused by fluorescent fluid. In the example of FIG. 24A, a microchannel was created using the pin-molding technique within the fibrin gel of the culture chamber. The microchannel then was endothelialized with HUVECs, and the patency of the conduit lumen was demonstrated by perfusion of a fluorescent dye-labelled fluid (tuned to a viscosity similar to blood) and the absence of instantaneous leakage into the surrounding matrix, as illustrated in the fluorescence image of FIG. 24B.

In order to reconstruct extracellular microenvironments that promote tumor cell extravasation and the formation of metastases, the vascularized hydrogel matrix was functionalized by integrating fibroblasts as supporting stromal cells, and implementing chemical depots of signaling molecules via programmable release capsules as illustrated in FIG. 22. Fewer than 50 A549 cells were injected into the 1 cm-long conduit to simulate CTCs.

Figure 25:
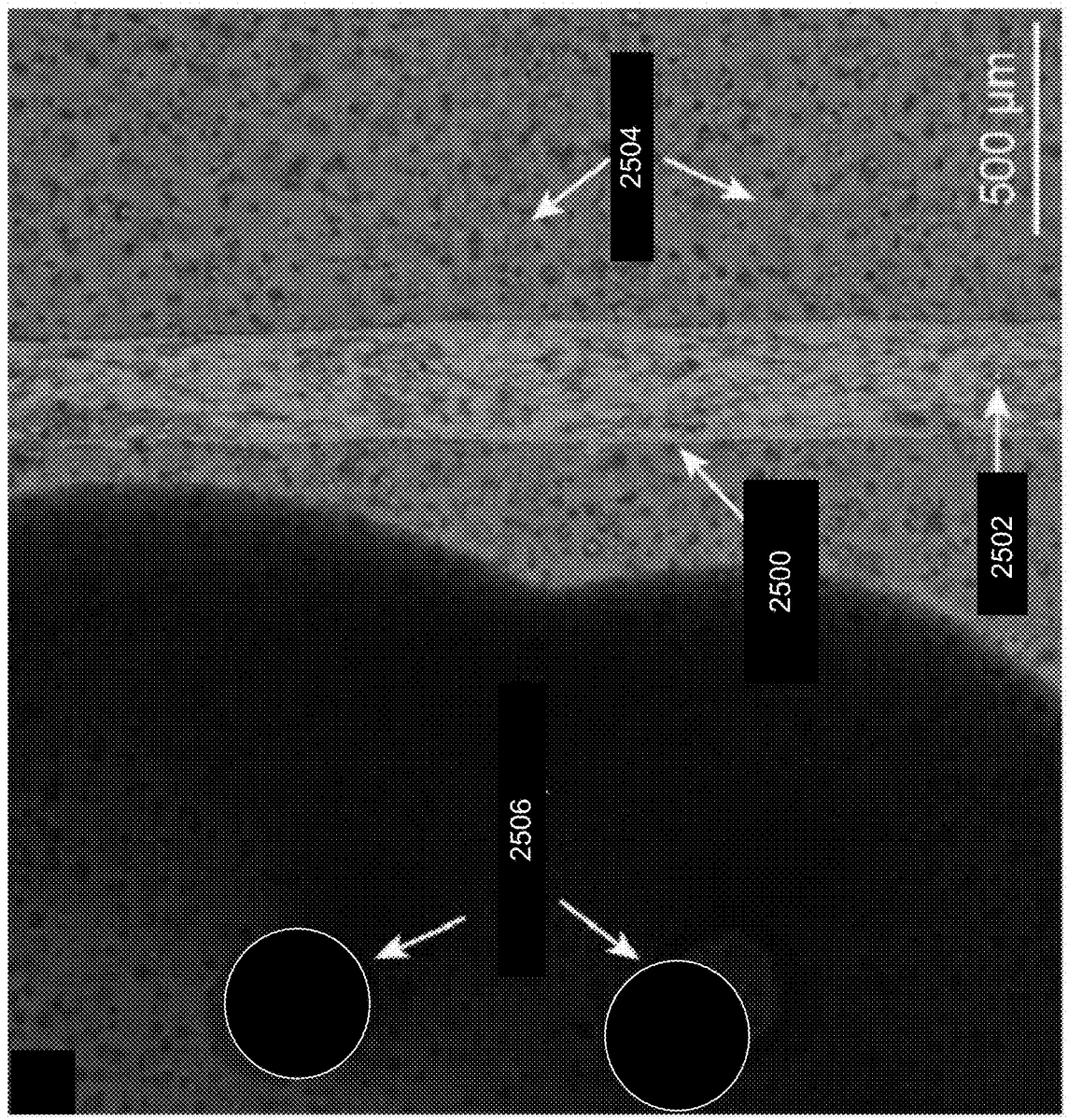
FIG. 25 is a composite image illustrating a prepared vascularized extravasation model prior to laser-triggered rupture of EGF-containing programmable release capsules in accordance with examples of this disclosure.

FIG. 25 is a composite image illustrating a prepared vascularized extravasation model prior to laser-triggered rupture of EGF-containing programmable release capsules, illustrating one representative extravasation model in the context of an example 3D-printed culture chamber. FIG. 25 illustrates a HUVEC-lined model conduit 2500 containing circulating A549 cells 2502, fibroblasts 2504 integrated in hydrogel matrix, and EFG capsules 2506 positioned on one side of the model conduit 2506.

FIG. 26A is fluorescence images of a conduit of an example vascularized 3D-printed culture chamber illustrating guided extravasation of A549s and subsequent metastases generated over time on days 0 and 2 following the programmable release of EGF from EGF-containing programmable release capsules in accordance with examples of this disclosure. FIG. 26B is fluorescence images of the conduit of FIG. 26A illustrating guided extravasation of A549s and subsequent metastases generated over time on days 4 and 6 following laser-triggered rupture of EGF-containing programmable-release capsules (inset: fluorescence image showing transendothelial formation of metastasis). FIGS. 26A and 26B illustrate transendothelial behavior of A549s directed by EGF gradients. As indicated by arrows, the tumor cells first moved toward the conduit boundary on the side of EGF capsule arrays. A transendothelial A549 cluster formed by day 4, indicating that cells underwent both extravasation and proliferation. This proliferative niche, associated with the conduit, can be observed in the inset of FIG. 26B, demonstrating that metastases were created with further tumor growth.

Figure 27:
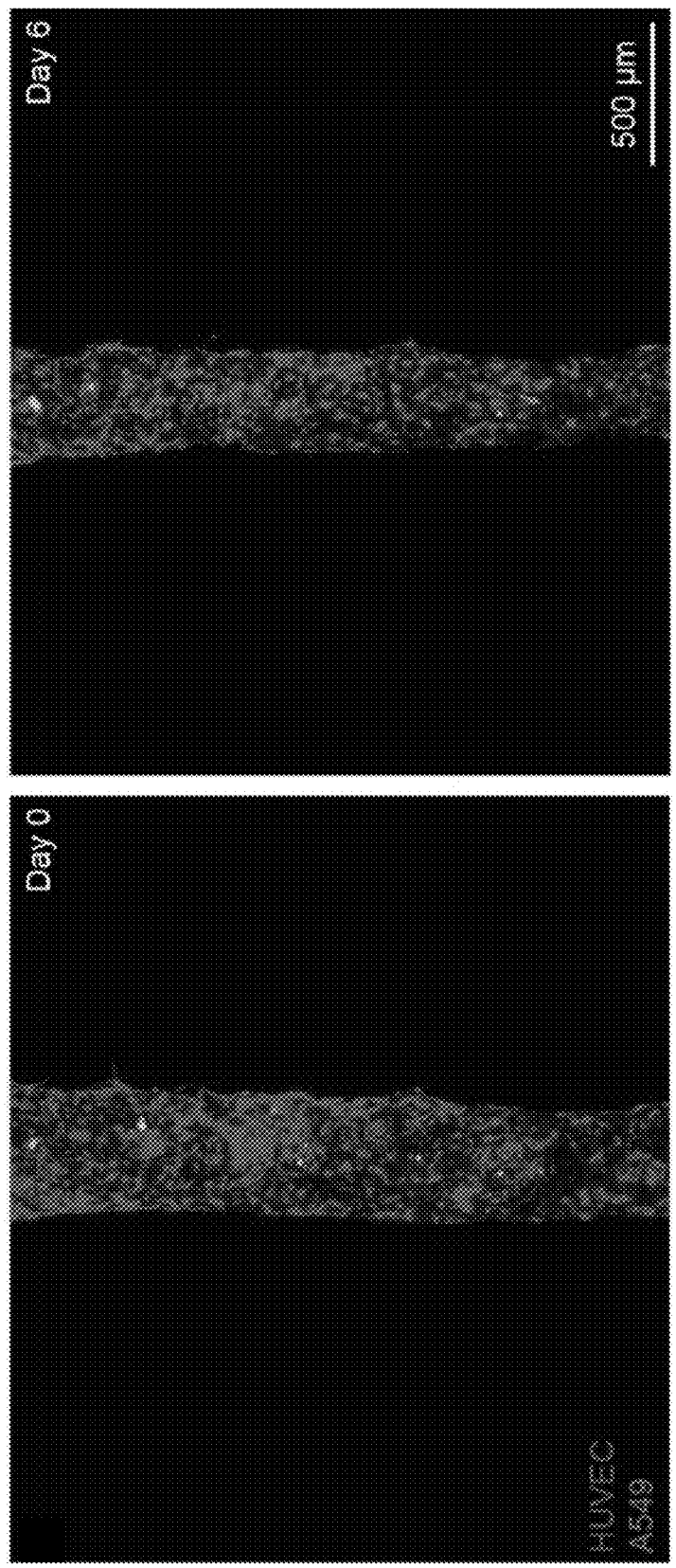
FIG. 27 is fluorescence images showing the vascularized extravasation model of FIG. 26 after A549s were injected within the conduit without rupture of EGF capsules.

FIG. 27 is fluorescence images showing the vascularized extravasation model of FIG. 26 after A549s were injected within the conduit without rupture of EGF capsules. To verify that the extravasation process described with respect to FIGS. 26A and 26B was guided by the EGF gradients, a control experiment was performed without the laser-rupture of EGF capsules. In this control, A549s within the conduit only showed random movement and no extravasation was observed on either side of the conduit. FIG. 27 thus illustrates that EGF released from printed capsules may diffuse through the endothelial barrier to induce conduit penetration of A549s and the generation of a metastatic lesion.

Figure 28:
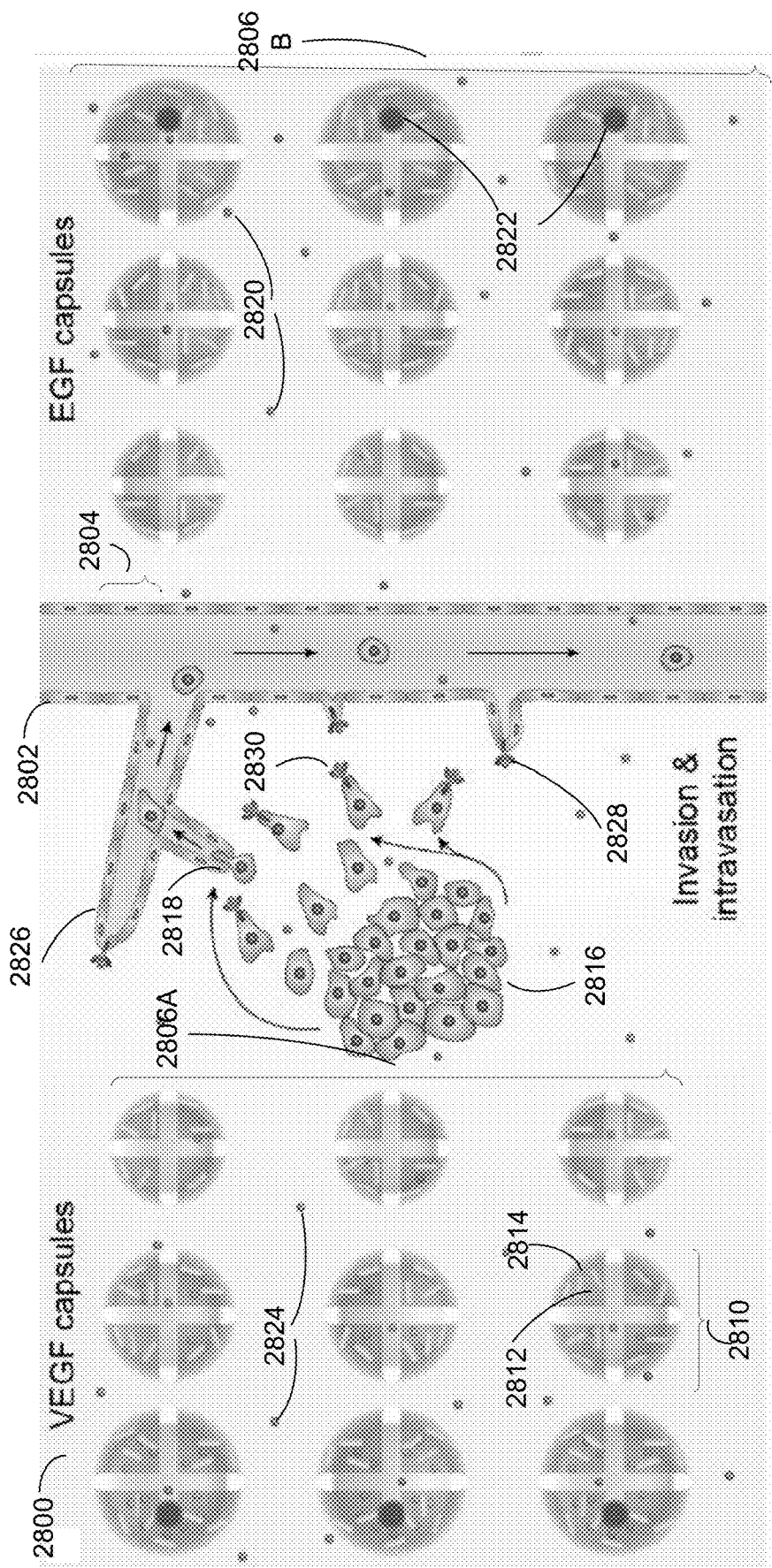
FIG. 28 is a graphical representation of tumor cell invasion of surrounding hydrogel and intravasation into the vasculature guided by EGF and vascular endothelial growth factor (VEGF) gradients in accordance with examples of this disclosure.

FIGS. 28-37B illustrate additional example vascularized in vivo environments and biological phenomena associated with vasculature, such as intravasation and invasion of tumor cells into vasculature during metastasis. To mimic the beginning of a metastatic cascade in the context of cell types relevant to the tumor microenvironment, a vascularized 3D-printed culture chamber was configured to provide spatiotemporal control over both tumor cell invasion and angiogenesis as illustrated in FIG. 28. The angiogenic mediator VEGF was introduced to promote and direct the formation of a vascular network from a pre-existing uniaxial conduit.

FIG. 28 is a graphical representation of tumor cell invasion of surrounding hydrogel and intravasation into the vasculature guided by VEGF and EGF gradients in accordance with examples of this disclosure. In some examples, a vascularized 3D-printed culture chamber 2800 may include a model conduit 2802 lined with living cells 2804, as further described below. Such example vascularized 3-D printed culture chambers 2800 may include 3D-printed programmed-release capsules 2806A and 2806B, which may be similar in one or more respects to the capsules described above. For example, capsules 2806 in vascularized 3-D printed culture chambers 2800 may include a core 2810 containing a biomolecular payload 2812 (e.g., EGF 2820 or other biomolecule) or other chemical, surrounded by a shell 2814 containing LSPR AuNRs or other suitable photothermally reactant components. Such capsules 2806 may be ruptured via laser wavelength 2822, as discussed above. Rupture of the capsules 2806 may create a gradient of the biomolecular or other chemical payload within the 3D-printed culture chamber 2800. In some examples, capsules 2806B containing a first type of payload may be 3D-printed on one side of the conduit 2802, (e.g., EGF 2820), and capsules 2806A containing a second type of payload (e.g., VEGF 2824) may be 3D-printed on another side of the conduit 2802. In some examples, a type of payload in some of the capsules 2806 may affect the behavior of cells of the model conduit 2806 (e.g., cause angiogenesis of daughter conduits toward a gradient), and a type of payload in other capsules may affect the behavior of cells within the gel matrix of the 3-D printed culture chamber 2800 (e.g., cause tumor cell 2816 migration toward the conduit).

As illustrated in FIG. 28, angiogenesis of daughter conduits 2826 off a main model conduit 2802 may be mediated by a VEGF gradient 2828 formed by VEGF 2824 released from ruptured capsules within the gel matrix of the 3D-printed culture chamber. Tumor cells 2816 in the gel matrix may intravasate through an endothelial barrier 2818 and circulate within the model conduit 2802. In some examples, an EGF gradient 2830 formed by EGF 2820 released from capsules 2806 in the gel matrix may help enable tumor cell intravasation into the conduit.

In some examples, a vascularized 3D-printed culture chamber 2800 configured for intravasation modeling may include a model conduit lined 2802 with living cells 2804, as further described below. Such example vascularized 3-D printed culture chambers 2800 may include 3D-printed programmed-release capsules 2806, which may be similar in one or more respects to the capsules described above. For example, capsules in vascularized 3-D printed culture chambers 2800 may include a core 2810 containing a biomolecular payload 2812 (e.g., VEGF, EGF, or other biomolecule) or other chemical, surrounded by a shell 2814 containing LSPR AuNRs or other suitable photothermally reactant components. Such capsules 2806 may be ruptured via laser wavelength, as discussed above. Rupture of the capsules 2806 may create a gradient of the biomolecular or other chemical payload within the 3D-printed culture chamber 2800, which may affect the behavior of cells within the model conduit 2802 (e.g., cause the cells to extravasate).

As illustrated in FIG. 28, angiogenesis of daughter conduits off the main conduit 2802 may be mediated by a VEGF gradient. Tumor cells 2816 may intravasate through an endothelial barrier 2818 and circulate within the model conduit 2802, such as via mediation by an EGF gradient. As discussed below with respect to FIGS. 29-37B, VEGF (and EGF, in some examples) released from printed capsules 2806 may promote and direct the formation of a vascular network from the model conduit 2802 in an example 3D-printed culture chamber 2800 in an experiment to induce conduit network formation and intravasation of A549 cells into the model conduit 2802.

Figure 29:
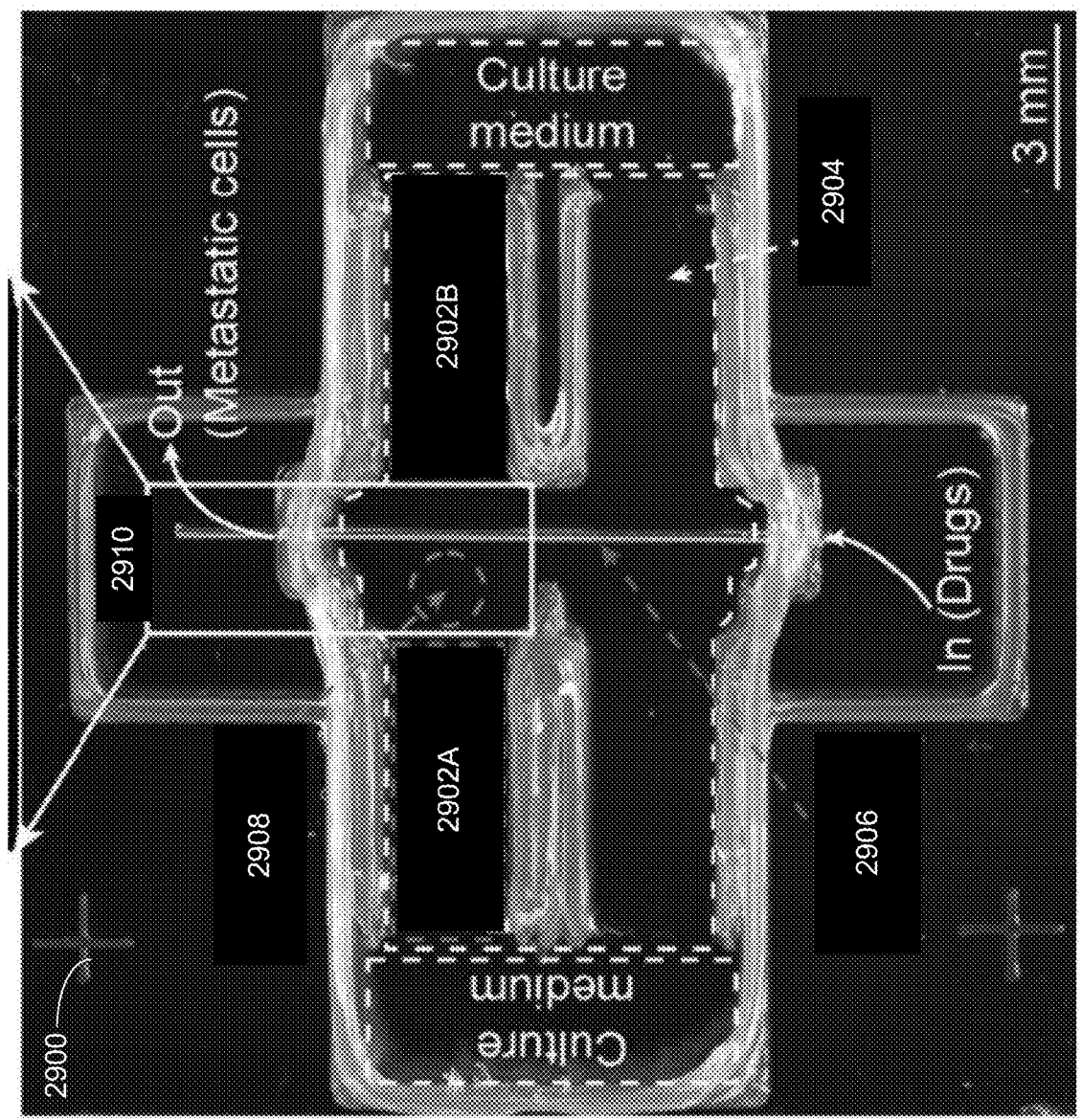
FIG. 29 is a digital image of an example vascularized 3D-printed culture chamber configured for cell intravasation and/or drug-response testing in accordance with examples of this disclosure.

FIG. 29 is a digital image of an example vascularized 3D-printed culture chamber configured for cell intravasation and/or drug-response testing in accordance with examples of this disclosure. In some examples, some features of the 3D-printed culture chamber 2900 of FIG. 29 may be substantially similar to one or more features of the 3D-printed culture chamber of FIG. 23 and/or the 3D-printed directional cell migration chamber of FIG. 10. In addition, the vascularized 3D-printed culture chamber 2900 of FIG. 29 may include 3D-printed capsules 2902A containing VEGF within the fibrin gel matrix 2904 on one side of the model HUVEC-lined conduit 2906 and a tumor-cell droplet 2908 positioned between the model conduit 2906 and the VEGF-containing capsules 2902A. In some examples, the 3D-printed culture chamber 2900 of FIG. 29 also may include 3D-printed capsules containing EGF 2902B within the fibrin gel matrix 2904 on a side of the model HUVEC-lined conduit 2906 opposite the VEGF-containing capsules 2902A. Tumor cells 2908 that intravasate into the HUVEC-lined conduit 2906 may travel through the conduit 2906 and be collected in a collection chamber 2910 at one end of the conduit 2906.

Figure 30:
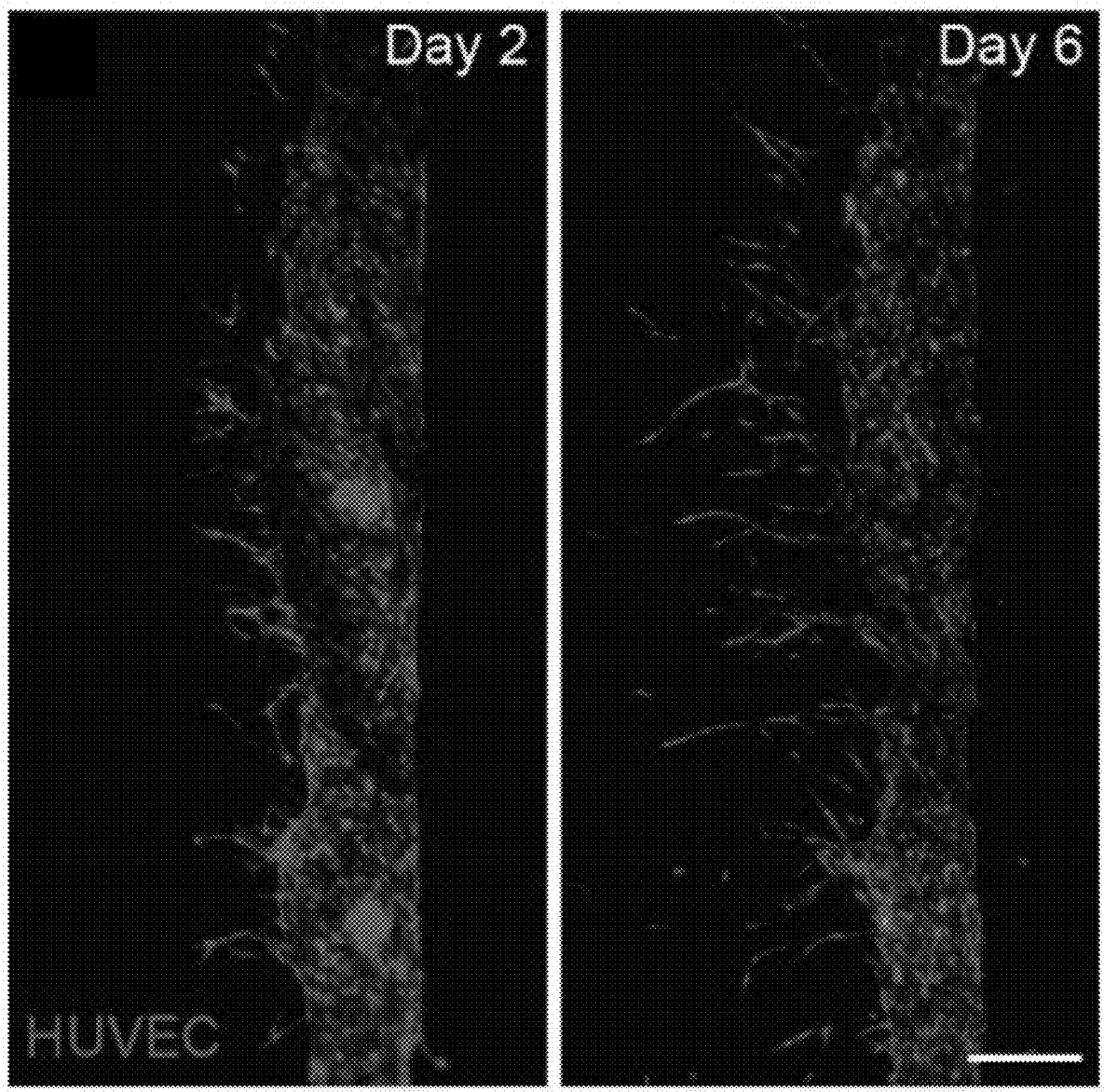
FIG. 30 is fluorescence images of an example vascularized 3D-printed culture chamber configured for cell intravasation illustrating random sprouting and extension from a main conduit over time in the absence of rupture of VEGF-containing capsules in accordance with examples of this disclosure.

FIG. 30 is fluorescence images of an example vascularized 3D-printed culture chamber configured for cell intravasation illustrating random sprouting and extension from a main conduit over time in the absence of rupture of VEGF-containing capsules. FIG. 30 illustrates that angiogenesis of daughter conduits are mediated by VEGF. In the example of FIG. 30, VEGF was mixed directly in fibrin gel of an example 3D-printed culture chamber (e.g., the culture chamber of FIG. 29) without formation of molecular gradients, and daughter conduit sprouts were found to randomly distribute on either side of the mother conduit.

Figure 31:
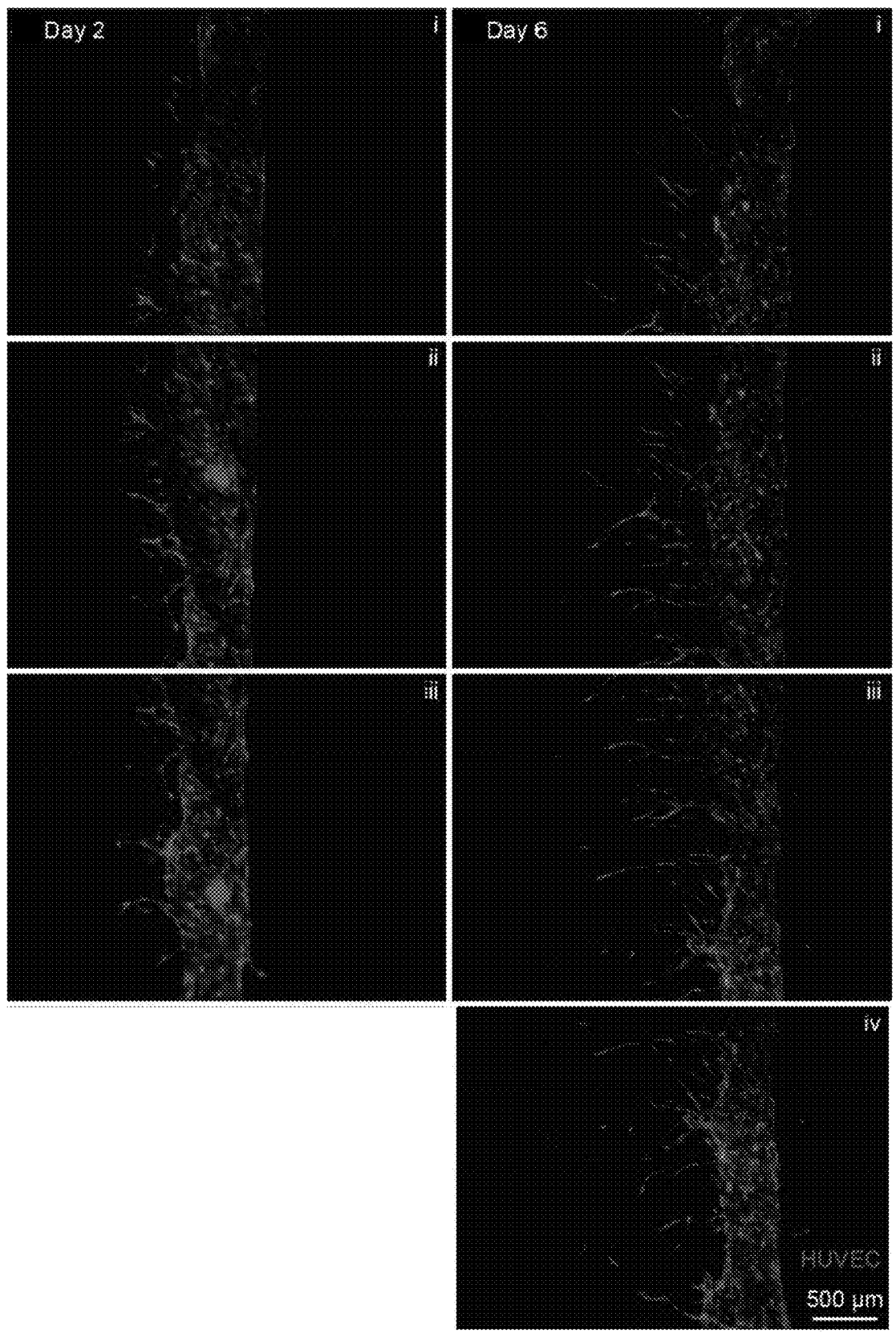
FIG. 31 is a series of mono-view fluorescent field images of the RFP-expressing HUVEC-lined conduit of FIG. 30.

FIG. 31 is a series of mono-view fluorescent field images of the RFP-expressing HUVEC-lined conduit of FIG. 30. The images in FIGS. 30 and 31 show the sprouting process from the existing conduit. By laser-triggered release of VEGF, numerous endothelial cells sprouted from the conduit, as illustrated in FIG. 31. The sprouts extended with longer culture time and as more VEGF capsules were ruptured. These daughter conduits were only observed on the side of the mother conduit where VEGF capsules were printed, consistent with the angiogenic process being guided by VEGF gradients generated from the capsules.

Figure 32:
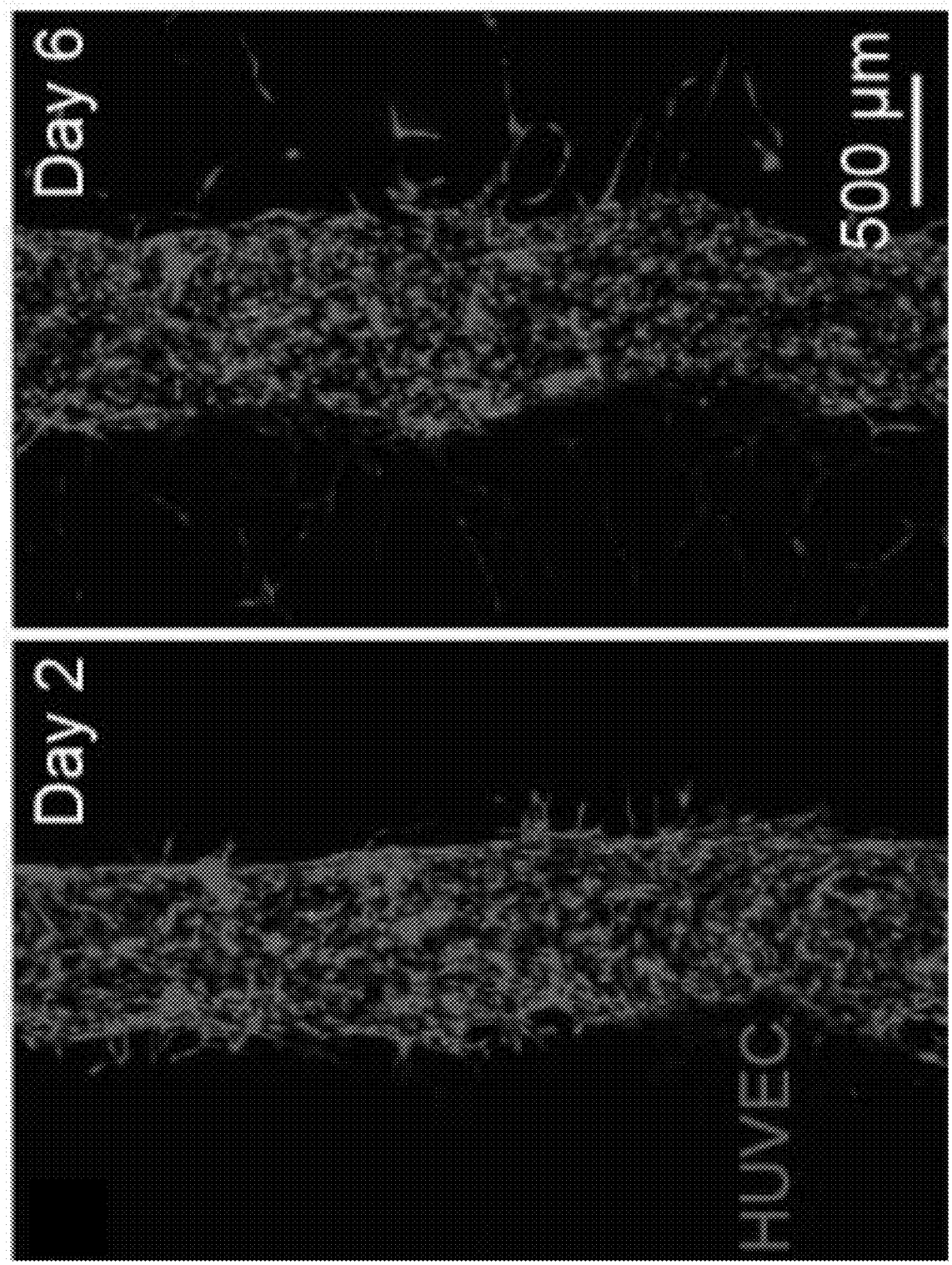
FIG. 32 is fluorescence images showing angiogenic sprouts generated from a main RFP-expressing HUVEC-lined conduit of an example vascularized 3D-printed culture chamber and their extension toward a single direction over time in accordance with examples of this disclosure, in which VEGF was introduced to promote and direct the formation of a vascular network from the conduit in accordance with examples of this disclosure.

FIG. 32 is fluorescence images showing angiogenic sprouts generated from a main RFP-expressing HUVEC-lined conduit of an example vascularized 3D-printed culture chamber and their extension toward a single direction over time in accordance with examples of this disclosure, in which VEGF was introduced to promote and direct the formation of a vascular network from the conduit.

Figure 33A:
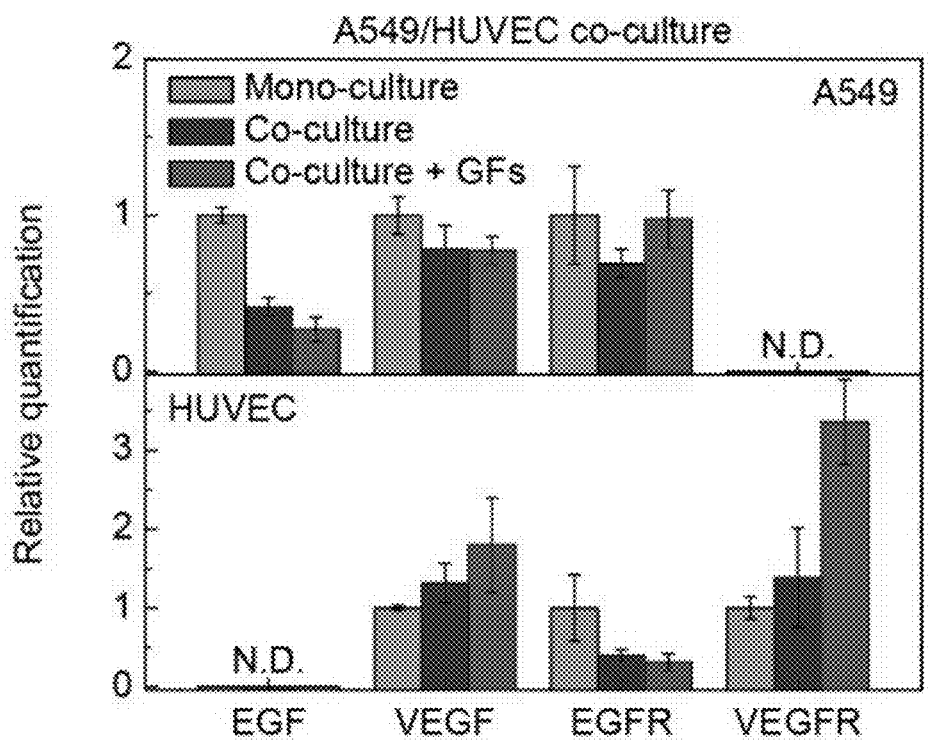
FIG. 33A is a graphical representation of expressions of EGF, VEGF, EGFR and VEGFR of A549s (upper panel) and HUVECs (lower panel) when mono cell-cultured and co-cell-cultured without and with EGF and VEGF in an example vascularized 3D-printed culture chamber configured for cell intravasation in accordance with the examples of this disclosure.

FIG. 33A is a graphical representation of expressions of EGF, VEGF, EGFR and VEGFR of A549s (upper panel) and HUVECs (lower panel) when mono cell-cultured and co-cell-cultured without and with EGF and VEGF in an example vascularized 3D-printed culture chamber configured for cell intravasation in accordance with the examples of this disclosure. In each three-sample group, mono cell-cultured is represented by the left-hand bar, cells co-cultured without EGF and VEGF are represented by the middle bar, and cells co-cultured with EGF and VEGF are represented by the right-hand bar. Since it is possible that the tumor cells and endothelial cells may cross-signal to each other through cell-secreted mediators, the source of the growth factors within the culture chamber was verified. It was confirmed by quantitative polymerase chain reaction (qPCR) that HUVECs within fibrin gels did not express EGF when cultured alone or in co-culture with A549s, as illustrated in the chart of FIG. 33B.

Tumor cells are known to secrete pro-angiogenic factors, such as VEGF, to activate endothelial cells of pre-existing blood conduits. When cultured alone, A549s expressed VEGF, but the expression was not enhanced with the introduction of HUVECs. The protein concentrations of the growth factors secreted from the cells were also measured, and the results were consistent with gene expression analysis. EGF protein concentration was below the limit of detection in all samples, whereas 12.8±0.3 pg/ml and 5.1±2.4 pg/ml VEGF were detected in 3D mono-cultured A549s and 3D co-cultured A549s/HUVECs, respectively.

The measured levels of VEGF were significantly lower than previously reported concentrations that were shown to induce endothelial sprouts in vitro, and also at least two orders of magnitude lower than the level of growth factor released from a single printed capsule. These results all suggest that the capsules are necessary to maintain the chemical depot for the in vitro models. Furthermore, the introduction of both growth factors (VEGF and EGF) to co-cultured samples caused the increase of VEGF receptor (VEGFR) expression in HUVECs, and EGF receptor (EGFR) expression in A549s (comparing co-culture and co-culture+GFs in FIG. 33A), indicating the active responses of the cells to the applied factors.

Figure 33B:
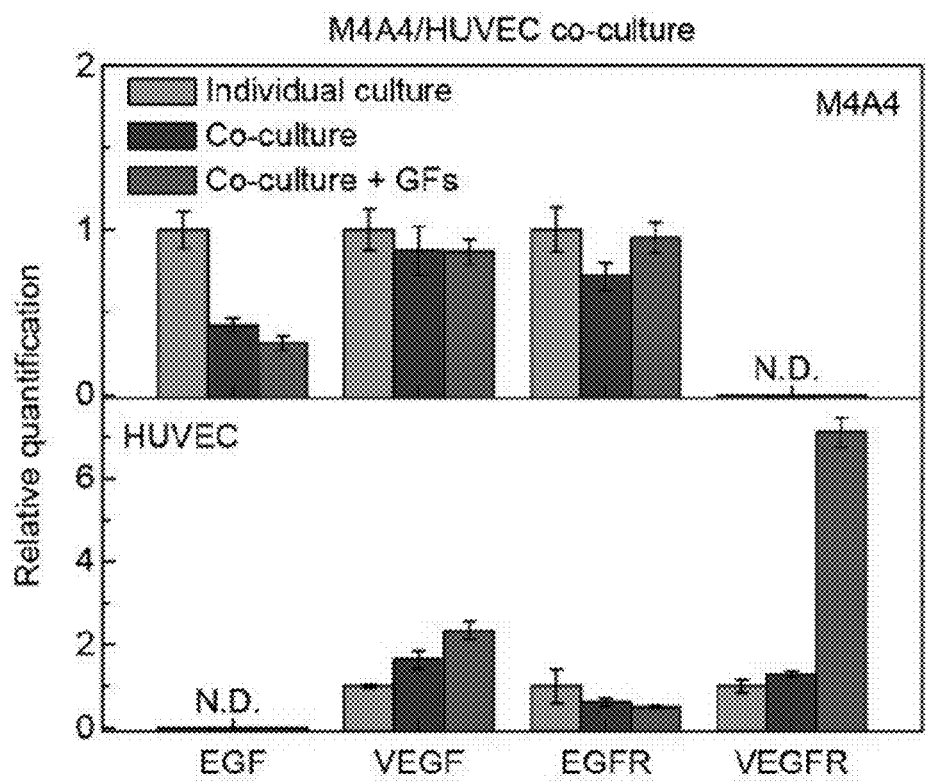
FIG. 33B is a graphical representation of expressions of EGF, VEGF, EGFR and VEGFR of M4A4s (upper panel) and HUVECs (lower panel) when mono (individual) cell-cultured and co-cell-cultured without and with EGF and VEGF in an example vascularized 3D-printed culture chamber configured for cell intravasation in accordance with the examples of this disclosure.

FIG. 33B is a graphical representation of expressions of EGF, VEGF, EGFR and VEGFR of M4A4s (upper panel) and HUVECs (lower panel) when mono (individual) cell-cultured and co-cell-cultured without and with EGF and VEGF in an example vascularized 3D-printed culture chamber configured for cell intravasation in accordance with the examples of this disclosure. In each three-sample group, mono cell-cultured is represented by the left-hand bar, cells co-cultured without EGF and VEGF are represented by the middle bar, and cells co-cultured with EGF and VEGF are represented by the right-hand bar. Results similar to those described with respect to FIG. 33A occurred when M4A4s were used in place of A549s, which illustrates that the results of FIG. 33A are not specific to the particular cancer cell line.

Figure 34:
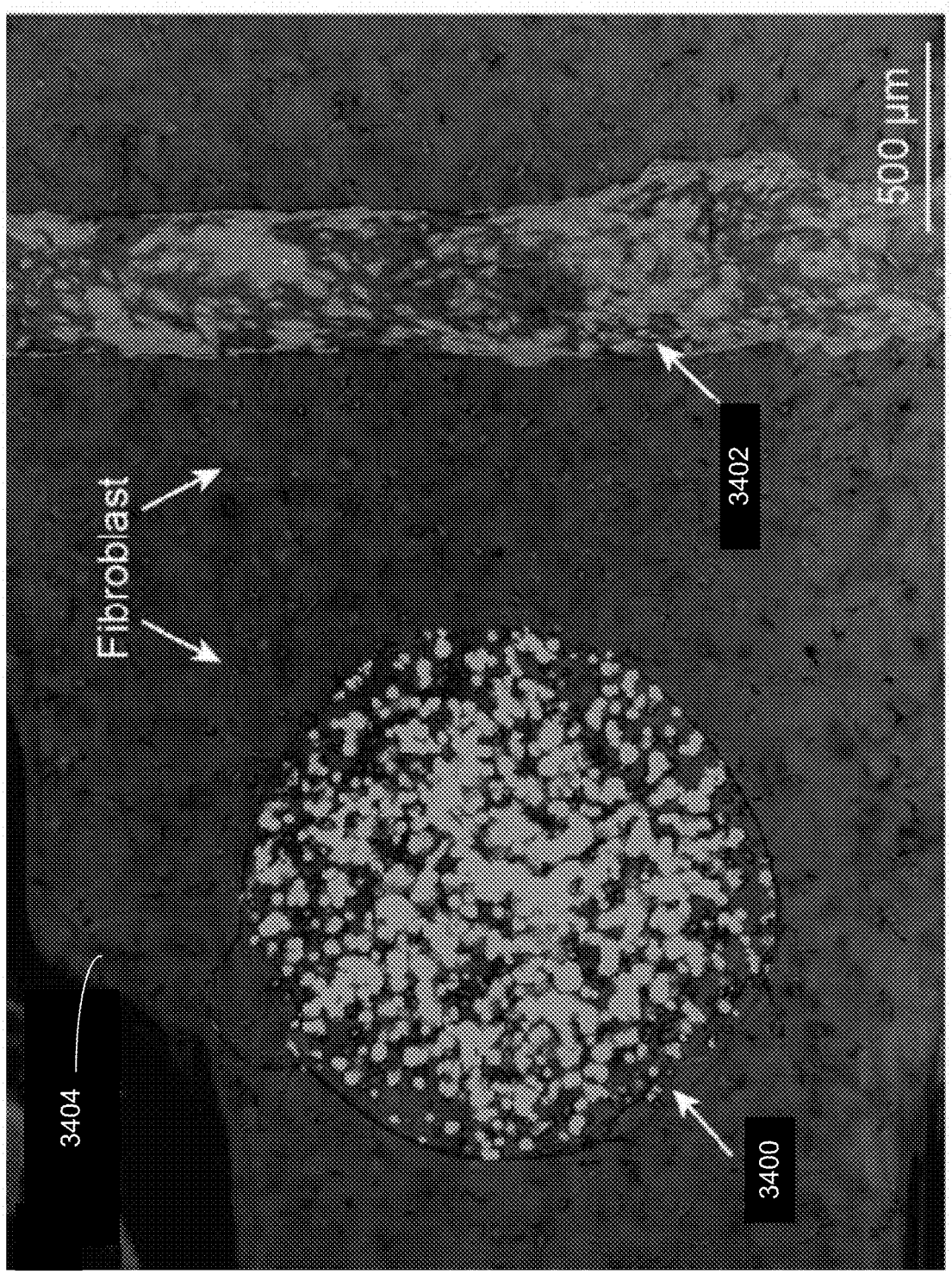
FIG. 34 is a composite image showing a prepared intravasation model before laser-triggered rupture of EGF- and VEGF-containing programmable-release capsules in an example vascularized 3D-printed culture chamber configured for cell intravasation in accordance with the examples of this disclosure.

FIG. 34 is a composite image showing a prepared intravasation model before laser-triggered rupture of EGF- and VEGF-containing programmable-release capsules in an example vascularized 3D-printed culture chamber configured for cell intravasation in accordance with the examples of this disclosure. In one example, a droplet of A549-laden fibrin 3400, simulating a primary tumor, was placed 1 mm away from the conduit 3402 within an example vascularized 3D-printed culture chamber 3404 configured for cell intravasation. EGF capsules were sequentially ruptured to guide tumor cell invasion and migration, while VEGF was released to modulate sprouting angiogenesis.

Figure 35:
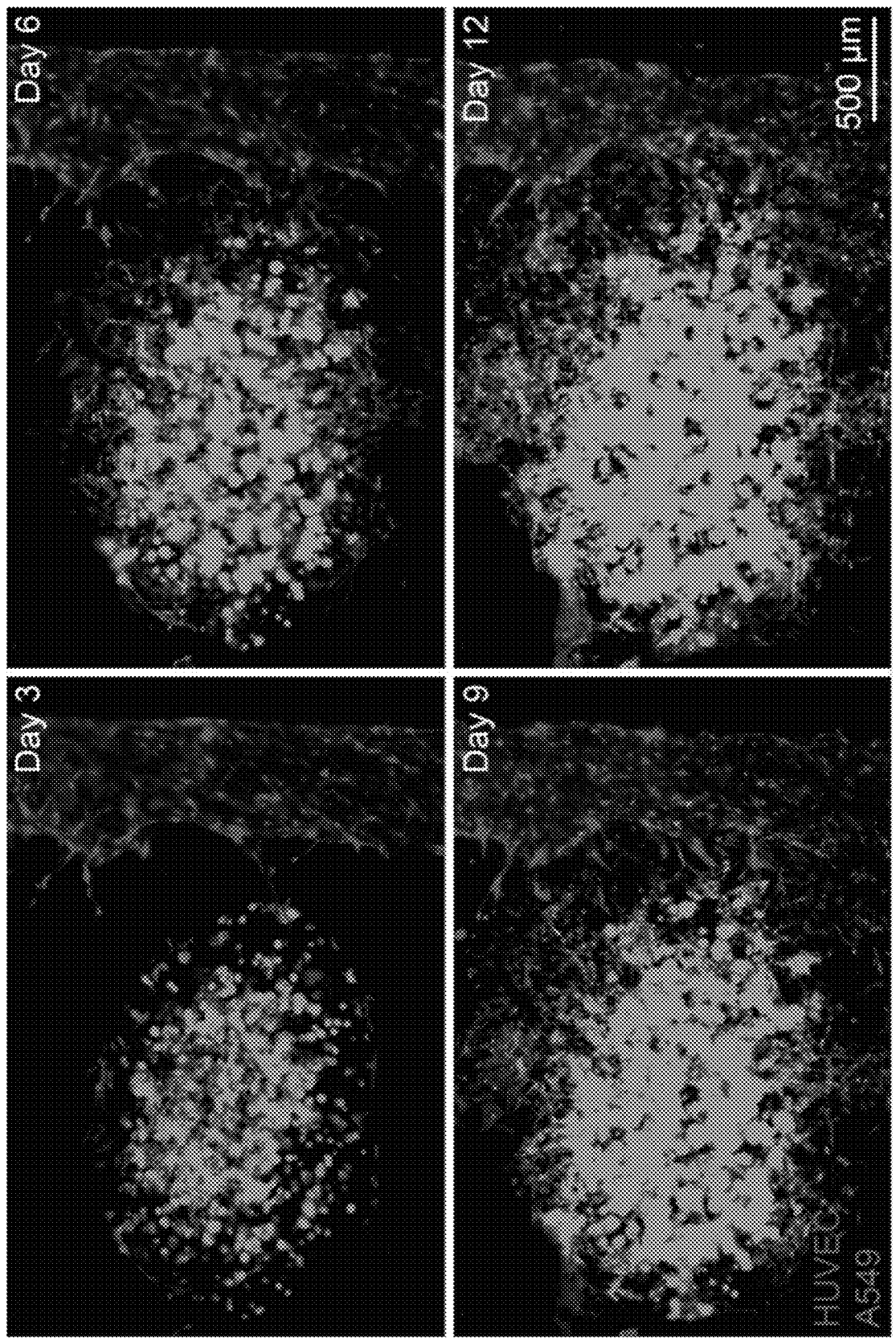
FIG. 35 is fluorescence images of an example vascularized 3D-printed culture chamber configured for cell intravasation on days 6, 9, and 12 following laser-triggered rupture of EGF-containing and VEGF-containing programmable-release capsules in the example of FIG. 34.

FIG. 35 is fluorescence images of an example vascularized 3D-printed culture chamber configured for cell intravasation on days 6, 9, and 12 following laser-triggered rupture of EGF- and VEGF-containing programmable-release capsules in the example of FIG. 34. FIG. 35 illustrates cellular migration patterns in response to these growth factors over time in the example of FIG. 34 and demonstrates that both tumor cell invasion and angiogenesis were directed toward one another. With time, more A549s migrated into the fibrin between the tumor cell droplet and the formed vasculature while a few tumor cells were found in the main conduit, indicating their intravasation into the main conduit. These guided behaviors of tumor and endothelial cells were also seen when fibroblasts were incorporated within the surrounding fibrin gel as tumor stroma.

Figure 36:
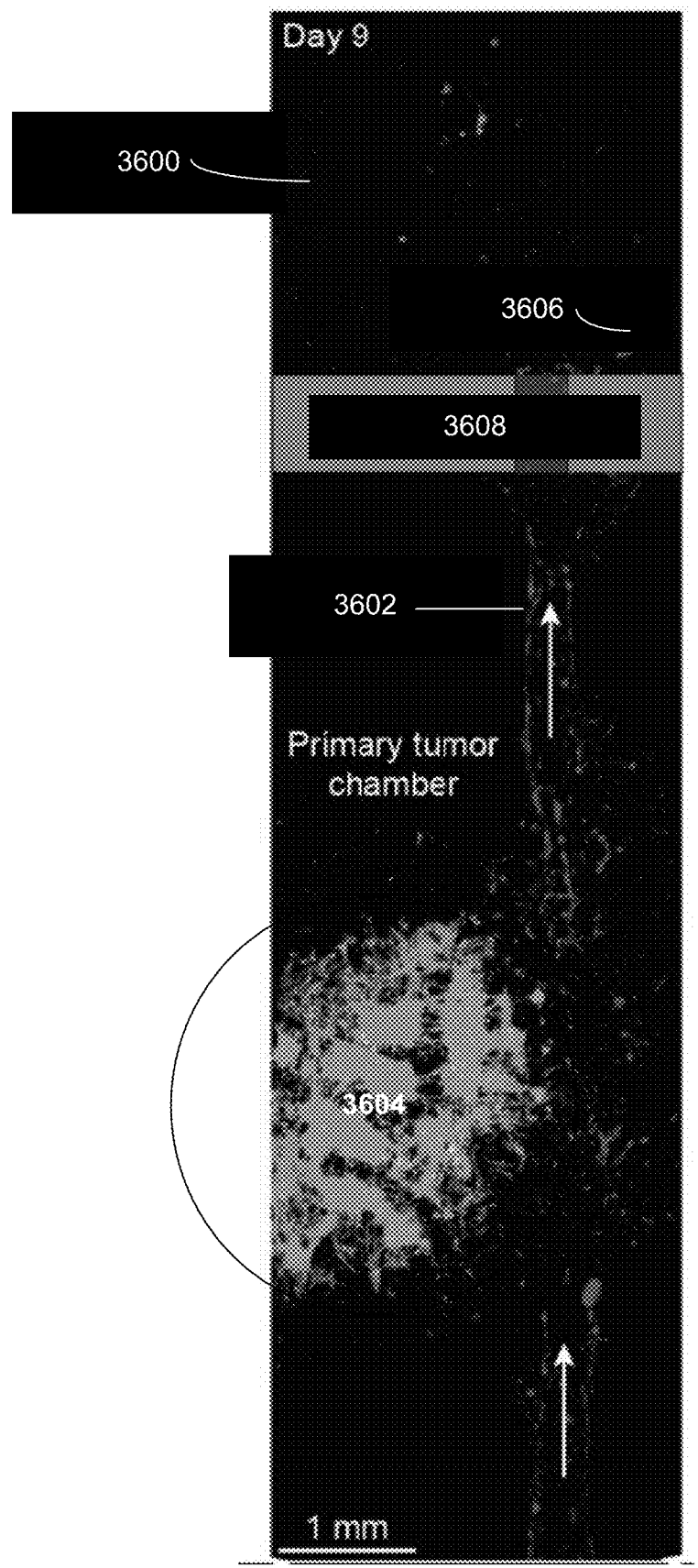
FIG. 36 is a panoramic fluorescence image of a vascularized 3D-printed culture chamber intravasation model on day 9 following rupture of VEGF- and EGF-containing capsules in accordance with examples of this disclosure.

FIG. 36 is a panoramic fluorescence image of a vascularized 3D-printed culture chamber intravasation model on day 9 following rupture of VEGF- and EGF-containing capsules. In some examples, the 3D-printed culture chamber of FIG. 36 may be similar to the 3D-printed culture chamber of FIG. 29. As illustrated in FIG. 36, the 3D-printed culture chamber includes a primary tumor chamber 3600 containing a model conduit 3602 and a model A549 primary tumor 3604. The culture chamber 3600 also includes a metastatic cell collection chamber 3606 positioned at one end of the model conduit 3602. The metastatic cell collection chamber 3606 was designed to access one end of the main conduit 3602, which was separated from the main chamber of the structured cell-laden gel by an impermeable silicone wall 3608. Since these metastatic cell collection chamber 3600 and the primary tumor chamber could only communicate through the endothelialized microchannel, the observation of A549s within the collection chamber 3600 indicated the intravasation of tumor cells 3604 originating from the primary bioprinted tumor droplet. Thus, the example vascularized 3D-printed culture chambers described herein may dynamically mimic the processes of invasion and intravasation and may enable the exploration of potential targets for future therapies. As discussed below with respect to FIG. 36A, the number of disseminated tumor cells may positively correlate to tissue culture time. This may be due to one or both metastasis and subsequent proliferation of disseminated cells, identifying an enriched population of metastatic cells that may be analyzed for specific CTC characteristics.

Figure 37A:
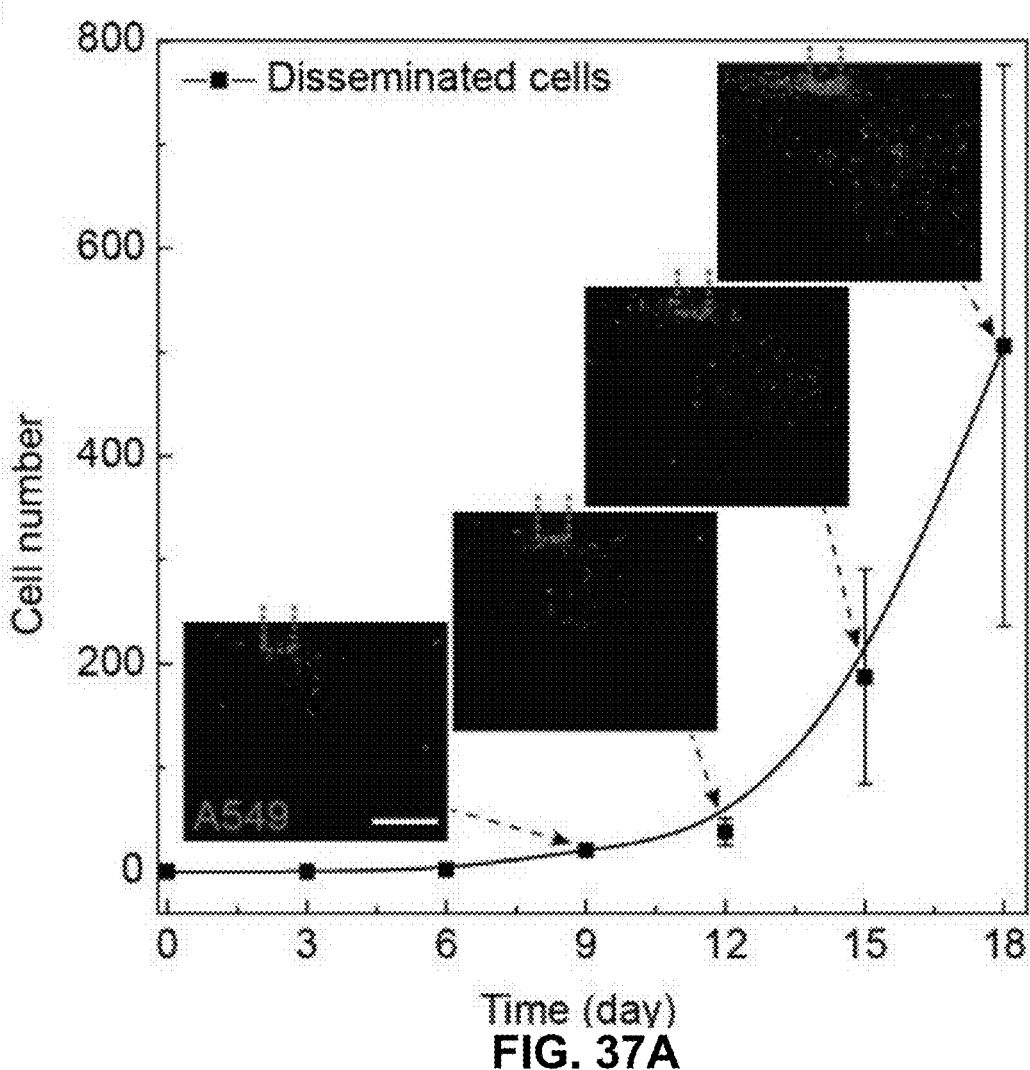
FIG. 37A is a graphical representation of an example population of disseminated A549s detected in a collection chamber vs time in the example vascularized 3D-printed culture chamber of FIG. 35.

FIG. 37A is a graphical representation of an example population of disseminated A549s detected in a collection chamber vs time in the example vascularized 3D-printed culture chamber of FIG. 35. FIG. 37A illustrates the population of disseminated A549s detected in the collection chamber vs time (mean±s.d., n=3 per group, inset: fluorescence images showing the disseminated A549s in the collection chamber, red dash frame showing the conduit position). Scale bar: 500 μm. The tumor cells that intravasated into the main vascular conduit started to travel with fluidic flow as CTCs and were collected the cell collection chamber.

Figure 37B:
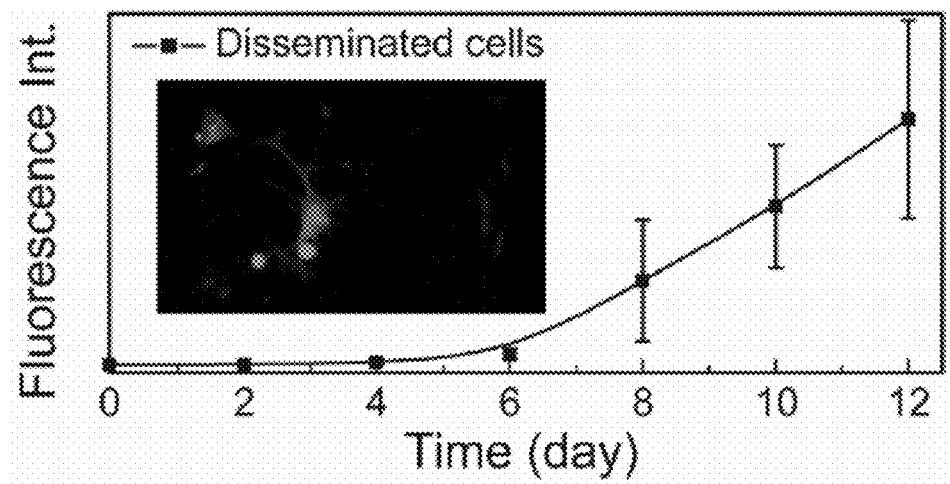
FIG. 37B is a graphical representation of another example population of disseminated A549s detected in the collection chamber vs time in an example vascularized 3D-printed culture chamber similar to the example of FIG. 35, in accordance with the examples of this disclosure.

FIG. 37B is a graphical representation of another example population of disseminated A549s detected in the collection chamber vs time in an example vascularized 3D-printed culture chamber similar to the example of FIG. 35, in accordance with the examples of this disclosure. As illustrated in FIG. 37B, fluorescence intensity, which is associated with the number of disseminated cells, increased over time, thus indicating of increasing metastasis and cell proliferation over time.

FIGS. 38A-41B illustrate an example vascularized 3D-printed model biological microenvironments (e.g., vascularized 3D-printed culture chambers) configured to recapitulate effects of a drug, other compound, or type of cell introduced via the model conduit on cells or compounds positioned outside of a model conduit within the vascularized 3D-printed culture chambers. In some examples, the vascularized 3D-printed culture chambers described with respect to FIGS. 38A-41B may be used as models for drug screening, such as anti-cancer drug screening. Such drug-screening models may be established in 3D-printed culture chambers having features that may be substantially similar to one or more features of the vascularized 3D-printed culture chambers of FIG. 23, FIG. 29, and/or the 3D-printed directional cell migration chamber of FIG. 10. For example, vascularized 3D-printed culture chambers used as models for drug screening may be substantially similar to the vascularized 3D-printed culture chamber of FIG. 29.

Although the example drug-screening models described below were configured to evaluate the effects of immunotoxins on tumor cells, the example vascularized 3D-printed culture chambers described herein may be adapted to test the effects of other substances or cells in biological models that represent other diseases or physiological conditions of interest. For example, such example vascularized 3D-printed culture chambers may be used in modeling a biological system, such as an immune system. In such an example, a vascularized 3D-printed culture chamber may be modified to circulate lymph fluid through the culture chamber via the model conduit in a controlled, closed loop. Vascularized 3D-printed culture chambers including a model immune system may enable testing of biological phenomena associated with the immune system, such as determination of immune cell response to stimuli. In some such examples, a model immune system may enable identification of immune cell types and/or biomolecules involved in anti-tumor response to tumor cells.

Figure 38:
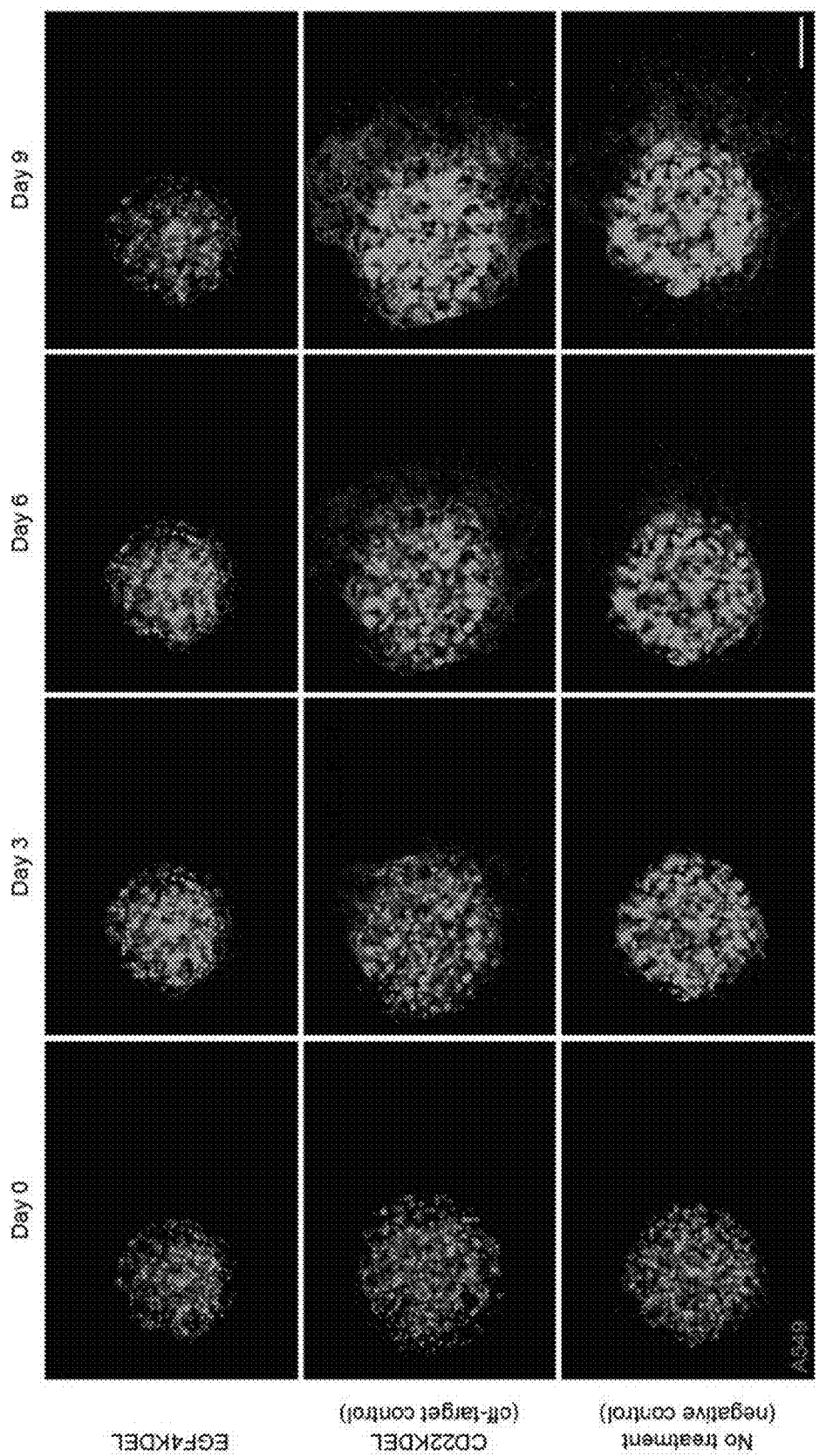
FIG. 38 is fluorescence images of printed A549s after immunotoxins were injected though a conduit within a fibroblast-laden fibrin gel of an example vascularized 3D-printed culture chamber configured for drug testing, showing drug effect over time, in accordance with examples of this disclosure.

FIG. 38 is fluorescence images of printed A549s after immunotoxins were injected though a conduit within a fibroblast-laden fibrin gel of an example vascularized 3D-printed culture chamber configured for drug testing, showing drug effect over time, in accordance with examples of this disclosure. The model conduits in the 3D-printed culture chambers used in such testing enabled recapitulation of in vivo drug delivery by the introduction of drugs through the model conduit. Two immunotoxin drugs that were developed in previous studies were tested. The first ligand-directed toxin, EGF4KDEL, consists of EGF and truncated *Pseudomonas* exotoxin with a C-terminus of Lys-Asp-Glu-Leu (KDEL) cloned as a single-chain molecule. Following the introduction of EGF4KDEL through the main conduit, the growth of tumor cells was significantly reduced compared to no drug treatment, and neither guided invasion nor migration was observed as illustrated in FIG. 38. EGF4KDEL demonstrates the potency of the engineered drug, while the truncated *Pseudomonas* exotoxin exhibits the competition between the EGF-linked toxin and the EGF released from printed capsules. Another ligand-directed toxin, CD22KDEL, was used as an off-target control. In CD22KDEL, the targeting domain is an anti-CD22 single-chain variable fragment that binds to the transmembrane protein CD22 specific to B cells. Since A549s do not express CD22, they were not affected by CD22KDEL, similar to the no-treatment negative control.

Figure 39A:
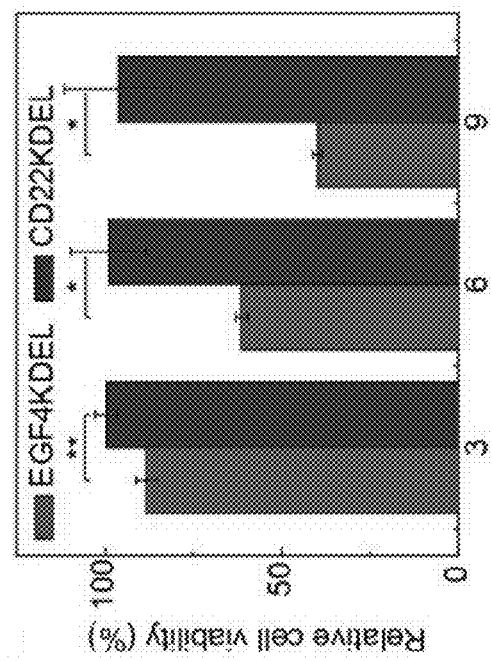
FIG. 39A is a graphical representation of cellular fluorescence intensity of A549s vs time without and with treatment of toxins in the example vascularized 3D-printed culture chamber of FIG. 38.

FIG. 39A is a graphical representation of cellular fluorescence intensity of A549s vs time without and with treatment of toxins in the example vascularized 3D-printed culture chamber of FIG. 38. Plots of cellular fluorescence intensity of A549s (normalized by intensity at day 0 before immunotoxins were added) are illustrated in FIG. 39A vs time without (squares) and with treatment of toxins (triangles: target; circles: off-target), demonstrating the effect of drugs on cell viability (mean±s.d., triangles: n=5, circles and squares: n=3 on each day).

Figure 39B:
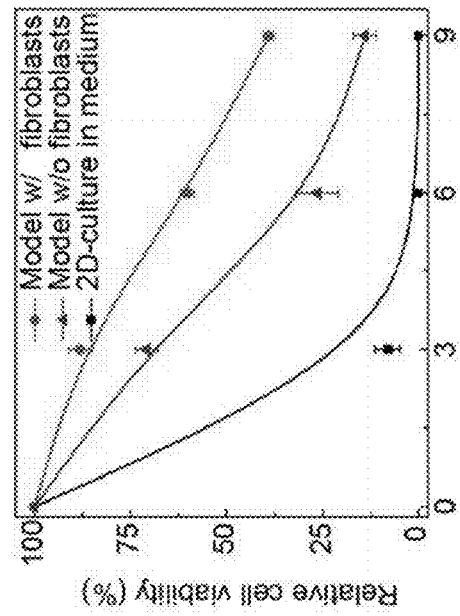
FIG. 39B is a graphical representation of the anti-cancer effect between immunotoxins over time in the example vascularized 3D-printed culture chamber of FIG. 38.

FIG. 39B is a graphical representation of the anti-cancer effect between immunotoxins over time in the example vascularized 3D-printed culture chamber of FIG. 38.

The bar graph of FIG. 39B illustrates a comparison of the anti-cancer effect of immunotoxins EGF4KDEL and CD22KDEL over time, showing the drug screening application of the model (mean±s.d., EGF4KDEL (bar on left in each pair): n=5, CD22KDEL (bar on right in each pair): n=3 on each day, *p<0.05, **p<0.005, day 3: p=0.002, day 6: p=0.025, day 9: p=0.023, unpaired, two-tailed Student's t test). These results indicate that 3D-printed tumor models, such as models established using example vascularized 3D-printed culture chambers described herein may be used as pre-clinical tools for drug screening.

Figure 39C:
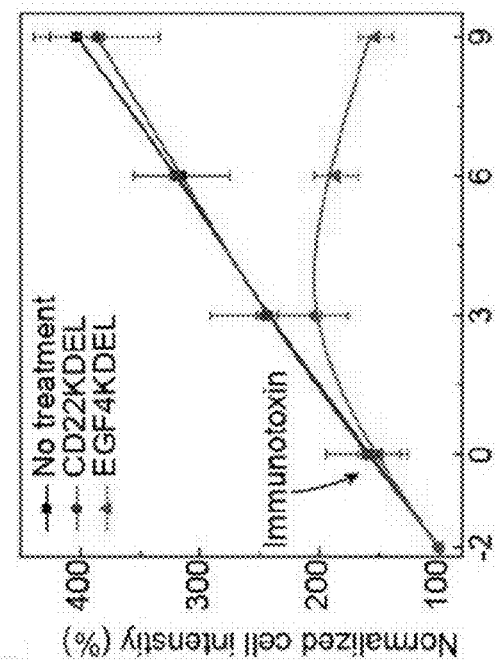
FIG. 39C is a graphical representation of an effect of toxins on an endothelial lining layer of a HUVEC-lined conduit of an example vascularized 3D-printed culture chamber in accordance with examples of this disclosure.

FIG. 39C is a graphical representation of an example effect of toxins on an endothelial lining layer of a HUVEC-lined conduit of a vascularized 3D-printed culture chamber in accordance with examples of this disclosure. The bar graph of FIG. 39C illustrates substantially no influence of either immunotoxin EGF4KDEL or CD22KDEL on HUVEC cell viability (mean±s.d., EGF4KDEL: n=5, CD22KDEL: n=3, *p>0.05, p=0.64, unpaired, two-tailed Student's t test). This results further indicates that 3D-printed tumor models, such as models established using example vascularized 3D-printed culture chambers described herein may be used as pre-clinical tools for drug screening.

Figure 39D:
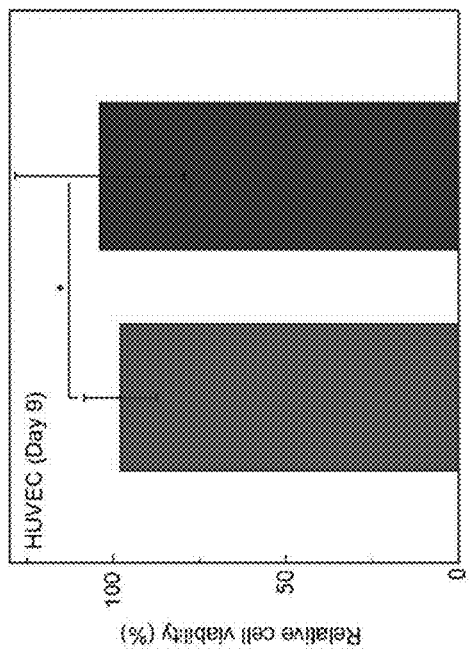
FIG. 39D is a graphical representation of relative cell viability of A549s vs time in the example vascularized 3D-printed culture chamber of FIG. 38.
Figure 40:
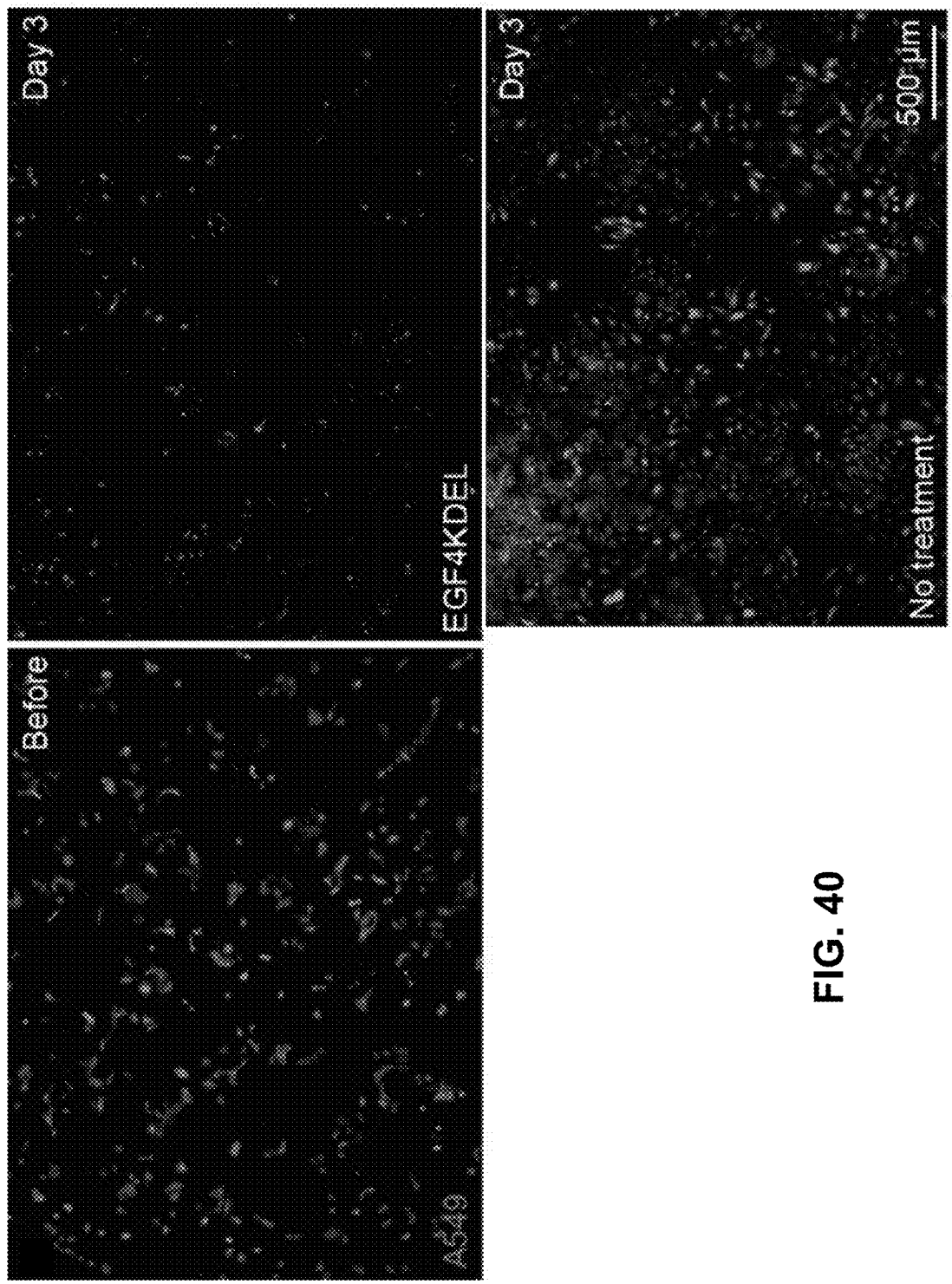
FIG. 40 is fluorescence images of 2D monolayer-cultured A549s before and 3 days after addition of immunotoxin in medium in an example vascularized 3D-printed culture chamber configured for drug testing in accordance with examples of this disclosure.

FIG. 39D is a graphical representation of relative cell viability of A549s vs time in the example vascularized 3D-printed culture chamber of FIG. 38. FIG. 40 is fluorescence images of 2D-monolayer cultured A549s before and 3 days after addition of immunotoxin in medium in an example vascularized 3D-printed culture chamber configured for drug testing in accordance with examples of this disclosure. To illustrate potential advantages of vascularized 3D-printed tumor models in simulating in vivo microenvironments for target cells, the anti-cancer effects of the immunotoxin in the 3D-printed tumor model of FIG. 38 was compared to the 2D monolayer-cultured A549s of FIG. 40. The plots in FIG. 39 illustrate relative tumor cell viability with the introduction of EGF4KDEL. The death rate of tumor cells in the 3D models was lower, compared to 2D monolayer-cultured cells on a flat plastic substrate, which may indicate that EGF4KDEL was less effective in the 3D model. This may be associated with the endothelial barrier and/or the stromal cells included in the vascularized 3D-printed tumor models described herein.

FIG. 41A is fluorescence images of printed A549s after the immunotoxin was injected into a fibroblast-free model though the built-in conduit in an example vascularized 3D-printed culture chamber, showing drug effect over time. FIG. 41B is a graphical representation of cellular fluorescence intensity of A549s vs time within fibroblast-laden models and fibroblast-free models, with and without toxin treatment in an example vascularized 3D-printed culture chamber configured for drug testing in accordance with examples of this disclosure.

As illustrated in FIGS. 39D, 41A, and 41B, tumor cells in the presence of fibroblasts exhibited lower proliferation and lower sensitivity to targeting toxins. This may imply a slower diffusion rate and/or a potential binding of drugs by fibroblasts when incorporated in the gel of the model (i.e., the fibroblasts may act as a drug sink). Thus, the vascularized 3D-printed culture chambers described herein may provide more meaningful insights into the in vivo cellular response to drugs, such as cell-cell and cell-ECM interactions, endothelial permeability of drugs, and/or the influence of stroma, relative to conventional 2D monolayer-culture. For example, such insights may help enable better determinations of in vivo drug efficacy and/or appropriate in vivo drug dosage than such determinations based on 2D monolayer-culture, which may translate to better clinical outcomes for patients treated with drugs screened using the 3D-printed models described herein.

FIGS. 42A-44H illustrate working examples of techniques for making components of example 3D-printed model biological microenvironments 4200. The components and techniques described below with respect to FIGS. 42A-44H may be incorporated into any of the example 3D-printed model biological microenvironments described above. In some examples, the example components and techniques described above may have one or more of the characteristics described below with respect to the working examples of FIGS. 42A-44H.

1) Optimizing the viability and morphology of cells for 3D bioprinting: The viability of DHSA-1426 canine vascular sarcoma cells, human fibroblasts 4206, and human HUVECs in different hydrogel matrices (i.e., gelatin methacrylate [GelMa], GelMa admixed with collagen, and Matrigel) was examined by printing them on culture dishes. The viability of the 3D-printed cells in the different matrices ranged from 75-95%.

2) Utilizing 3D silicone scaffolds 4204 for 3D bioprinting cancer cells 4202: Printed DHSA-1426 sarcoma cells were readily detectable along the channels in the 3D scaffold 4200. The DHSA-1426 sarcoma cells proliferated rapidly and organized themselves into tube-like structures 4208 in 3D space over a period of three days.

3) Creating a fluidic structure for vascular channels in a 3D hydrogel matrix: A 3D structure containing vascular channels with HUVECs in a human fibroblast-laden hydrogel matrix was built, which provides a model for printing cancer cells 4202 and for controlling chemical depots. This structure was tested using multiple hydrogels such as GelMa, GelMa admixed with collagen, and fibrinogen.

4) Creation of a model 4200 to address gaps in knowledge in sarcoma research: There is a paucity of models to understand the cellular and topological organization of sarcoma tumors, and the mechanisms of sarcoma cell movement and metastasis. The 3D tissue-mimics described herein provide a foundational model for discovery and hypothesis testing to address gaps in knowledge in these areas of sarcoma biology and pathogenesis.

Some of the models described below with respect to FIGS. 42A-44H may enable testing of the hypothesis that the topology of sarcoma tumors is not random, and that it is associated with distinct patterns of gene expression in the tumor, vascular, and stromal compartments that facilitate entry and exit of sarcoma cells into blood conduits in response to biological gradients. For example, vascularized models that more closely resemble the appearance and behavior of natural conduits through a "4D bioprinting" approach may be constructed, which may enable control over the cell alignment and to create structures that more closely mimic in vivo cancer tissues.

One example model and technique described below with respect to FIGS. 42A-44H was to create a novel biomimetic 3D in vitro tumor model to determine the role of cell migration in the 3D microenvironment 4200. For example, such models and techniques may model the interactions between sarcoma cells and non-malignant cells that compose the supporting stroma for these tumors (endothelial cells 4210 and fibroblasts 4206), thus providing more information on the mechanisms that drive the topological and anatomical organization of mesenchymal tumors (e.g., sarcomas).

Figure 42B:
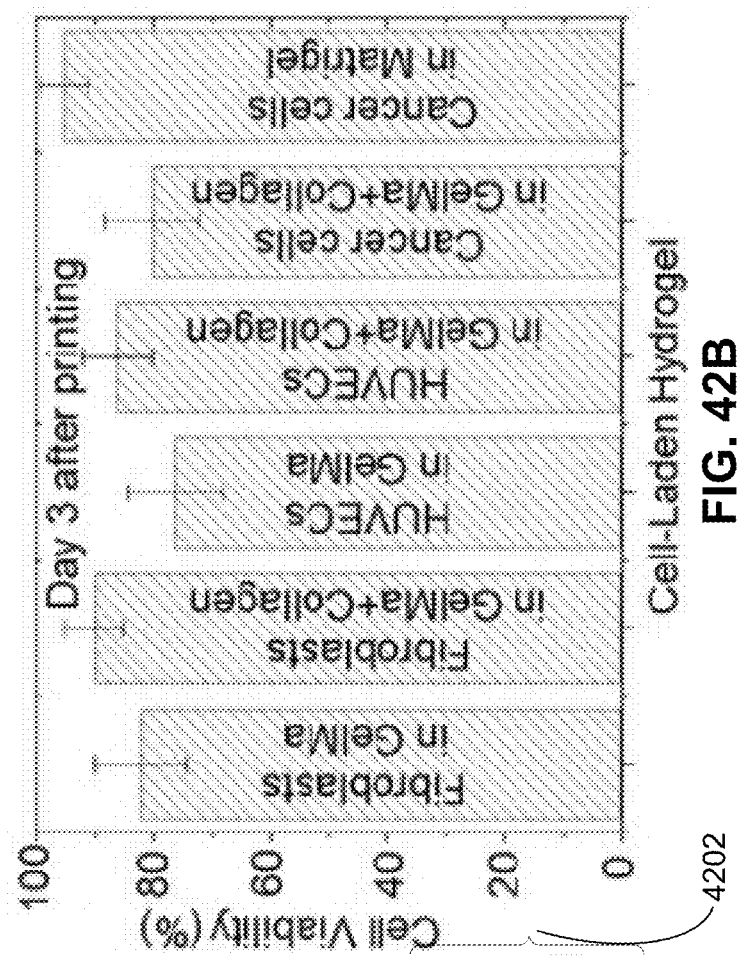
FIG. 42B is a graphical representation of example cell viability assay results of printed cell-laden hydrogels at day 3.
Figure 42A:
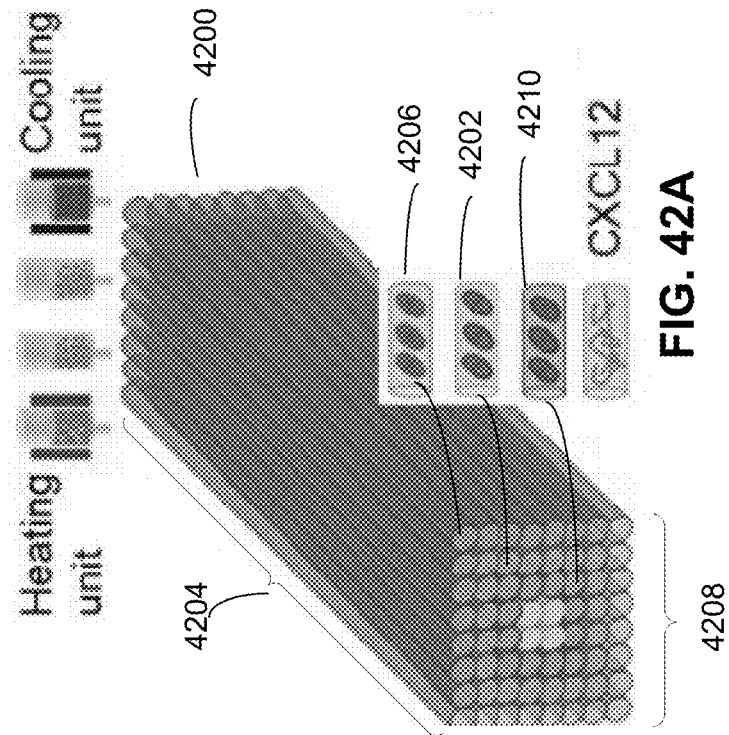
FIG. 42A is a graphical representation of example 3D architectures including multiple cells and biomolecules to form a 3D bio-mimetic tumor model in accordance with examples of this disclosure.

FIG. 42A is a graphical representation of example 3D architectures including multiple cells and biomolecules to form a 3D bio-mimetic tumor model in accordance with examples of this disclosure. As illustrated in FIG. 42A, multiple types of cells (sarcoma cancer cells 4202, endothelial cells 4210, and fibroblasts 4206) were precisely positioned together with biomolecules during the creation of custom 3D-bioprinted scaffolds 4204. First, the effect of bioprinting in different matrices on the viability and morphology of the printed cells was evaluated. To examine cell viability in hydrogel suspensions, 10,000 DHSA-1426 canine vascular sarcoma cells 4202, human fibroblasts 4206, or human umbilical vein endothelial cells (HUVECs) 4210 at a concentration of 2☐106 cells/ml (5 μL) were suspended in different hydrogels and printed on culture dishes. For cell suspensions (or cell-laden hydrogel matrices), gelatin methacrylate (GelMa) hydrogel was chosen due to its high cell adhesion and biocompatibility, together with a photo-initiator for crosslinking (5-10 s) under exposure to blue light. To increase cell viability and tune the stiffness of the matrix, GelMa was admixed with collagen and Matrigel.

FIG. 42B is a graphical representation of example cell viability assay results of printed cell-laden hydrogels at day 3. The viability of cells in each hydrogel mixture was assessed after 3 days using a Live/Dead staining kit. The viability of the cells in the different matrices ranged from 75-95% as illustrated in FIG. 42B, which is similar to what has been reported previously in 3D-hydrogels.

FIGS. 42C-42N are optical microscope, fluorescence, and photographic images of cells in different example matrices and scaffolds in accordance with examples of this disclosure. FIGS. 42C and 42D respectively are optical microscopic images of printed fibroblasts 4206 in GelMa admixed with collagen, and GelMa alone matrix at day 3.

FIGS. 42E and 42F respectively are fluorescence images of HUVECs 4210 in GelMa admixed with collagen, and a GelMa matrix at day 3.

FIGS. 42G-42J are fluorescence images of printed sarcoma cancer cells 4202 (FIG. 42G) in GelMa admixed with collagen; its zoomed-in optical image (FIG. 42H); in Matrigel (FIG. 42I) and its zoomed-in optical image at day 3 (FIG. 42J). FIG. 42K is a photograph of 3D bioprinting of cells on a scaffold, in which the dimension of each channel is ~150×150×5,000 (w×h×l)μm$^3$. FIGS. 42L and 42M respectively are optical images of 3D-printed sarcoma cancer cells in scaffolds at day 0 and at day 3. FIG. 42N is a fluorescence image of FIG. 42M.

To quantitatively analyze the morphology of the cells in the hydrogel matrices, fluorescence microscopy imaging (FIGS. 42C-42J) was conducted. Fibroblasts 4206 grown in GelMa admixed with collagen developed a more elongated morphology than fibroblasts 4206 grown in GelMa suspension alone (FIGS. 42C and 42D). In contrast, the morphology of HUVECs 4210 was similar when they were grown in GelMa admixed with collagen or in GelMa alone (FIGS. 42E and 24F).

The morphology of the sarcoma cancer cells 4202 also was similar whether they were grown in GelMa alone, in GelMa admixed with collagen, or in Matrigel. On the other hand, the patterns of tumor cell growth were distinct in the different matrices. DHSA-1426 sarcoma cells formed 3D spheres in each matrix; the spheres were similar in shape and size (diameter ~50 μm) to those that form when DHSA-1426 cells are grown in ultra-low attachment plates under serum-free conditions (i.e., hemangiospheres, FIGS. 42G-42J). In contrast, DHSA-1426 displayed vascular-like growth patterns in Matrigel (FIGS. 42I and 42J), which are characteristic of the original vascular tumor (hemangiosarcoma) and similar to the appearance of these cells under in vivo conditions in xenograft tumors. An advance was a developed ability to create formalin-fixed, paraffin-embedded blocks from the tissues grown in each of these matrices, providing material to enable assessment of topological relationships using histological methods. From these experiments, it may be inferred which hydrogel matrices are able to support all three cell types for 3D bioprinting, and how they can be modified to address distinct biological questions.

After optimization of the hydrogel matrices, 3D-printed scaffolds 4204 made of silicone to were utilized to construct ~150 μm sized channels 4212 (or barriers) where cells could be located and grown in the designed space. Sarcoma cancer cell-laden Matrigel was printed directly onto the designed silicone scaffold matrix FIG. 42K). The printed DHSA-1426 cells were readily detectable along the channels 4212 (FIG. 42L), proliferated rapidly, and organized themselves into tube-like structures 4208 in 3D space over a period of three days (FIGS. 42M and 42N). The results indicate that the 3D-bioprinting methods described herein may mimic the cellular function, and that the printed cancer cells may retain functional characteristics and responses to their microenvironment.

FIGS. 43A-43L illustrate a platform containing vascular channels to enable examination of sarcoma cell intravasation and extravasation in accordance with examples of this disclosure.

Figure 43A:
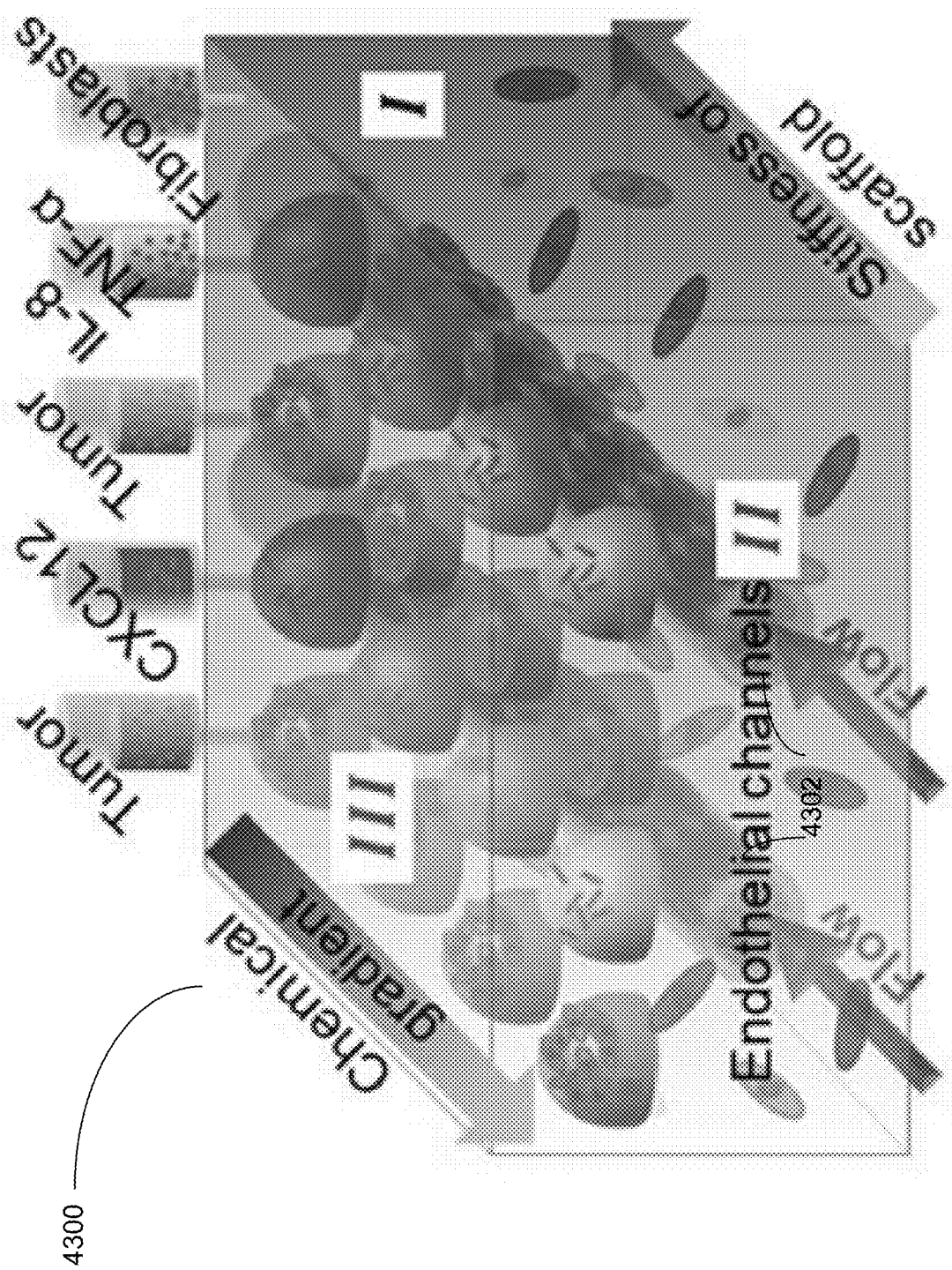

FIG. 43A is graphical representation of an example 3D bioprinted model tumor platform for cell migration in accordance with examples of this disclosure. The model tumor platform 4300 illustrated in FIG. 43A was designed (i) to build vascular channels 4302 with endothelial cells, and (ii) to position (e.g., 3D print) sarcoma cells within a 3D, fibroblast-laden matrix that would support a chemical depot.

FIG. 43A is a schematic illustration of an example 3D-bioprinted tumor platform 4300 for cell migration. FIGS. 43B and 43C respectively are optical images of a single HUVEC-lined vascular channel supporting a fibroblast cell-laden fibrinogen matrix and GelMa admixed with collagen matrix. FIG. 43D is a cross-sectional optical image of a HUVEC lined vascular network supporting a fibroblast cell-laden matrix. FIGS. 43E and 34F respectively are florescence microscope images of the vascular network at day 9 shown top-down, and shown in cross-section.

Figures 43K, 43L:
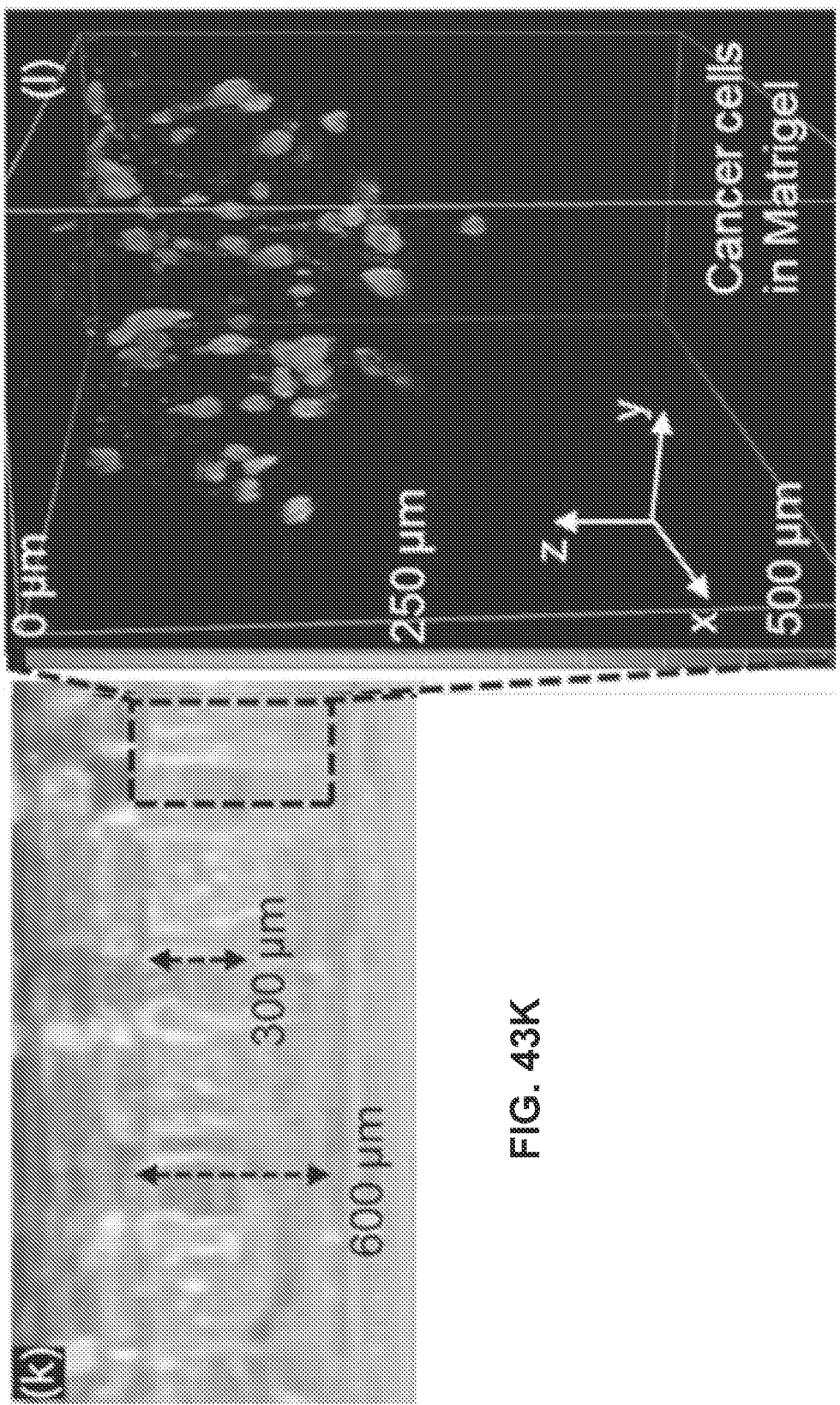

FIG. 43G is an optical image of 3D-bioprinted cancer cells with 400 μm interspacing in a 3D-scaffold channel. The dimension of each channel is ~150×300×5,000 (w×h×l) μm$^3$. FIGS. 43H-43J are confocal fluorescence images of two types of 3D-bioprinted sarcoma cancer cells (DHSA-1426 with GFP and COSB with RFP) in a 3D scaffold channel at day 3. FIG. 43K is an optical image of 3D-printed sarcoma cancer cells in a 3D scaffold channel filled with Matrigel. The dimension of the channel is ~300×600×5,000 (w×h×l) μm$^3$. FIG. 43L is a confocal image of 3D-bioprinted sarcoma cancer cells (droplet) within a 3D Matrigel matrix at day 3.

To create the model of FIGS. 43A-43J, vascular structures were constructed in 3D hydrogel chambers by adding a modified, templated micro-molding approach onto the bioprinting technology described above.

First, 3D-printed silicone chambers (volume of ~5×5×3 (w×l×h) mm$^3$) were built, and a needle was inserted through each chamber to create a channel. Then, the chambers were filled with a fibroblast-laden hydrogel (i.e., GelMa, GelMa admixed with collagen, or fibrinogen), as illustrated in FIGS. 43B and 43C, and in region I in FIG. 43A. This 3D structure was designed to mimic the 3D ECM with fibroblasts at a concentration of ~2×106 cells/ml and low elastic modulus (below 10-1 Pa), which is comparable to other ECM-like inks.

After allowing the system to stabilize for 3 days, the needles were removed from the chambers, creating perfusable channels within the 3D structures, as illustrated in FIGS. 43B and 43C. Subsequently, HUVECs in growth media were seeded into the templated, perfusable channels via a customized microfluidic system (flow rate ~0.5 ml/min).

HUVECs lined the channels and formed confluent monolayers (FIGS. 43D-43F and Region II in FIG. 43A). The medium was replaced every other day, and the HUVEC-channels remained confluent for at least 9 days. Cross-sectional views of representative conduits revealed that the cells formed lumina.

For cancer cell lines, the cells were printed in precise positions within the desired 3D architecture (FIGS. 43G-43L). To assess spatial control of cell organization and placement, two sarcoma cancer cell lines (DHSA-1426 modified to express GFP (4330 in FIG. 43H); and COSB modified to express RFP (4332 in FIG. 43I) were 3D-printed in a scaffold, prepared to print two types of cancer cells with 400 μm interspacing in a single channel (volume ~150× 300×5000 (w×h×l)μm$^3$) (FIG. 43G).

Next the cells and their placement were visualized using multiphoton confocal microscopy (FIG. 43H-43J). Next, the vertical positioning of cells in a single channel (volume of ~300×600×5,000 (w×h×l)μm$^3$) was evaluated. The channel was filled with Matrigel via 3D bioprinting, and then dispensed printed droplets of sarcoma cancer cell-laden hydrogel (diameter of ~300 μm) within the Matrigel matrix (FIG. 43K). The 3D confocal images showed that the printed cancer cells within the 3D Matrigel matrix were held in place for at least three days (FIG. 43L). These results allowed for spatial organization of different cells types and biomolecules in a complex arrangement, within a 3D hydrogel matrix containing templated micro-vascular structures (see Region III in FIG. 43A). Taken together, the developments using 3D bioprinting methods enable mimicry of cellular function as shown in FIG. 43A may provide a novel model to evaluate characteristics of sarcoma cell migration and inter-cellular interactions in real-time.

The techniques described herein may be used to build vascularized models that closely resemble the appearance and behavior of natural conduits (Region II in FIG. 43A). To achieve this, the orientation (or construction) of endothelial cells and smooth muscle cells can be controlled in the presence of other stromal elements, such as cancer cells and immune cells, as well as biomolecular gradients within the supporting 3D fibroblasts-laden ECM. This requires a "4D bioprinting" approach, as discussed below with respect to FIGS. 44A-44H. A step above 3D bioprinting, 4D printing technology can be defined as self-transformation in the form or function of 3D-printed objects upon exposure to predetermined stimuli, including pressure, heat, current, UV, or other energy sources. The 4D-bioprinting technologies described herein may provide better control over the cell alignment, in turn creating a structure that more closely mimics in vivo tissues.

FIGS. 44A-44H illustrate aspects of example 4D-printed vascular structures in accordance with examples of this disclosure.

Figure 44A:
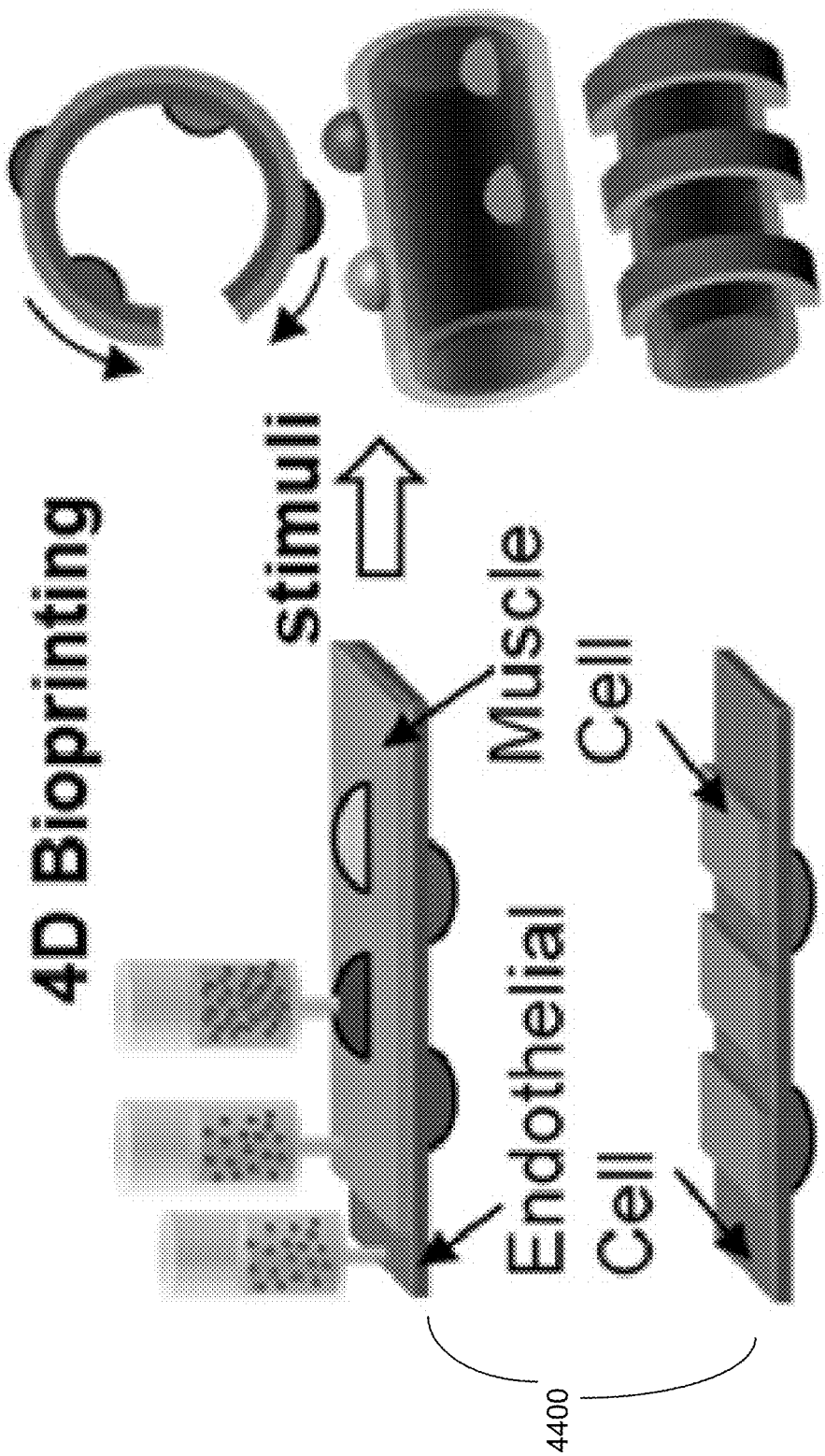

FIG. 44A is a schematic of 4D-printed vascular structures containing multiple cells and biomolecules. FIGS. 44B and 44C are optical images of self-folded PEGDA films in a sideview (FIG. 44B) and in cross-section (FIG. 44C). The diameter of the tubular structures is ~400 μm. FIG. 44D is an optical image of 3D-printed sarcoma cancer cell-laden GelMa admixed with collagen matrix. The dimensions of the structure are ~3×0.05×5 (w×h×l) mm$^3$.

FIG. 44E is florescence image of a part of the printed cancer cells at day 3. FIGS. 44F and 44G are top-down views of florescence images before (FIG. 44F) and after (FIG. 44G) removing a needle within a 3D hydrogel matrix. FIG. 44H is a cross-sectional view of FIG. 44G.

In principle, hydrogels are 3D polymer networks strongly imbibed with water. Hence, hydrogels can swell and shrink considerably (>10× in volume) when the amount of water in the polymer network changes. This can occur in response to different stimuli such as humidity, touch, heat, light, pH, ionic strength, among others. A biocompatible poly(ethylene glycol) diacrylate (PEGDA) matrix was used to establish a proof-of-principle for 4D bioprinting. To control the direction of self-folding, rectangular PEGDA films with a dimension of 3×5 (w×l) mm$^2$ with integrated ridge arrays on a glass substrate were 3D-printed (not shown here). The printed PEGDA film was maintained at 37° C. in PBS buffer for 1 hr, after which the film was swollen (the hydrogels used were 3D cross-linked hydrophilic polymers that swell readily in water) and released from the glass substrate. As the water evaporated, the structure gradually shrunk and eventually self-folded, as illustrated in FIGS. 44B and 44C.

The 4D-bioprinting technique illustrated in FIGS. 44A-44H was conducted using live cells at a concentration of ~10×106 cells/ml in GelMa admixed with collagen matrix. ~200 µm was the maximum thickness of the matrix (in an area of 3×5 mm$^2$) used to produce multiple layered structures 4400 in this example, where the thickness of a single printed layer was ~50 µm. Next, a single layer of sarcoma cancer cell-laden matrix was 3D-printed on a glass substrate, as illustrated in FIG. 44D. Although FIGS. 44A-44H illustrate 4D-bioprinting in an example using cancer cells, such techniques may be used with other cell types, such as with HUVECs.

The cells remained healthy and continued proliferating for 3 days, as illustrated in FIG. 44E, after which the freestanding printed structure was dried and folded along a needle of ~400 µm diameter. Drying the structure for 30 min did not significantly affect cell viability. Next, the structure was transferred to GelMa matrix, and an additional layer of the GelMa matrix was added to cover the structure, as illustrated in FIG. 44F, the matrix was cross-linked, and the needle was removed, thereby creating a vascular structure as illustrated in FIG. 44G. Cross-sectional views of representative conduits revealed that this process successfully resulted in the formation of lumina, as illustrated in FIG. 44H. In some examples, the techniques described herein for 4D-bioprinting may be applied to the 4D-bioprinting of multi-layered structures.

FIG. 45A illustrates a schematic image of a 3D bioprinted in vitro tumor model with multi-scale vascular networks for drug screening. FIG. 45A illustrates a schematic image of a 3D bioprinted in vitro tumor model 4500 with multi-scale vascular networks for drug screening. Tumor tissues 4502 with multiscale vascular networks are constructed as a drug screening tool for bispecific immunotoxins. First, a hydrogel droplet containing tumor cells 4502 and endothelial cells 4504 is printed next to the main vessel that is built using a pin-molding method. Small capillaries are formed by the endothelial cells 4504 within the printed tumor droplet, after the optimization of co-culture condition. Then, along with the guided angiogenesis of both capillaries within the droplet and the main vessel, the tumor droplet is connected to the main vessel via neovessels. Finally, a tumor model with perfusable multiscale vasculatures is achieved, providing a microenvironment to mimic in vivo drug delivery. Both tumor cells and tumor-generated capillaries within the printed droplet can be used as targets to screen anti-cancer drugs.

Two immunotoxins are employed to test the feasibility of the models. These two anti-cancer drugs share the same toxin fragments (truncated *Pseudomonas* toxin, 4506). The first one is a mono ligand-directed toxin, consisting of epidermal growth factor (EGF, green rhombus), and targets epidermal growth factor receptor (EGFR)-overexpressing carcinoma cells. The other drug is designed as bi-ligand directed. In addition to the EGF-toxin, the fragment of urokinase (also known as urokinase-type plasminogen activator, uPA, 4508) is also fused to the molecular chain as EGF-toxin-uPA. Urokinase receptor (uPAR) has been demonstrated as a cancer marker, which is overexpressed by tumor-generated vasculatures. Therefore, the second drug is expected to target both tumor cells and capillaries within the droplet. During the tests, each drug is introduced to an individual model through the main vessel and drug molecules diffuse into the tumor droplet via the vascular network.

FIG. 45B illustrates a composite microscope image (right) showing a representative tumor model. A fibrin gel droplet containing prostate cancer cell, CRW-R1 (4510), and HUVECs (4512) was printed next to the main vessel that was endothelialized by HUVECs (4512). Fibroblast-laden fibrin gel, mimicking tumor stoma, was used as the matrix for the model.

FIGS. 45C, 45D and 45E illustrate time-lapse fluorescence images (from Day 2 to Day 6) of a bioprinted model showing the formation of multi-scale vascular networks. FIGS. 45C, 45D and 45E illustrate time-lapse fluorescence images (from Day 2 to Day 6) of a bioprinted model showing the formation of multi-scale vascular networks (4510: A549, lung cancer cells; 4512: HUVECs). With the optimization of co-culture condition of tumor cells and endothelial cells, small capillaries are formed as a network within the printed tumor droplet. Simultaneously, daughter vessels sprouted out from main vessel towards tumor droplet. Along both angiogenesis of the capillaries within the droplet and sprouts of the main vessel, the tumor droplet was connected to the main vessel via neovessels after a certain time of culture. This process was guided by 3D printed hydrogel droplets (gelatin) containing relevant molecular factors on the top of the fibrin gel matrix.

FIG. 45F illustrates a fluorescence image showing the perfusability of the vascular network. FIG. 45G illustrates a fluorescence image showing the perfusability of the vascular network sprouts between the main conduit and the tumor droplet. FIG. 45H illustrates a fluorescence image showing the perfusability of the vascular network capillaries formed within the tumor droplet. FIGS. 45F, 45G and 45 H illustrate fluorescence image showing the multiscale and the perfusability of the vascular network. FIG. 45F shows that the main conduit and the tumor droplet were connected by neovessels from both capillaries within the droplet and sprouts of the main vessel. Within the model, the vasculature was developed as a multiscale network, ranging from venules (main vessel: several hundred micrometers; sprouts: 50 to 100 µm, FIG. 45G) to capillaries (10 to 20 µm, FIG. 45H). The perfusability of the vascular network was tested by injecting blue fluorescence beads (1 µm) into the main vessel (FIGS. 45F and 45G). A few beads could be observed within neovessels between the tumor droplet and main vessel (indicated by the white circle in FIG. 45G), suggesting the vascular network was perfusable.

The techniques described in this disclosure may be implemented, at least in part, using hardware, software, firmware or any combination thereof. For example, various aspects of the described techniques, such as 3D-bioprinting and/or laser application techniques, may be implemented under control of one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

Aspects of the techniques described in this disclosure, such as computerized control of 3D-bioprinting and/or laser application, may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform aspects of such techniques, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various aspects of the disclosure have been described. These and other aspects are within the scope of the following claims.

What is claimed is:

1. A 3D-printed in vitro model biological microenvironment, the 3D-printed microenvironment comprising:
   a platform;
   a gel matrix 3D-printed on the platform, wherein the gel matrix comprises a chemical composition configured to culture a first type of live cells;
   one or more culture medium chambers configured to contain cell culture medium for the first type of live cells;
   a target chemical disposed at one or more locations within the gel matrix, the target chemical forming a chemical depot from which a chemical gradient is created within the gel matrix; and
   a conduit disposed within the gel matrix, defining a lumen comprising a second type of live cells, and defining an inlet from outside of the gel matrix to the lumen, wherein the conduit is configured to enable at least some of the first type of live cells to migrate through the conduit and facilitate flow of at least: some of the live cells to an outlet of the conduit, and enable introduction of at least one of other cells, chemical mediators, or drugs into the 3D-printed microenvironment via the inlet of the conduit, and wherein at least a portion of the gel matrix is disposed between the conduit and the one or more culture medium chambers.

2. The 3D-printed microenvironment of claim 1, further comprising:
   a plurality of 3D-printed programmable-release capsules 3D-printed into the gel matrix.

3. The 3D-printed microenvironment of claim 2, wherein each programmable-release capsule comprises:
   a core 3D-printed into the gel matrix, wherein the core comprises at least one of a target chemical, a molecule, or one or more cells.

4. The 3D-printed microenvironment of claim 3, wherein each programmable-release capsule comprises: a shell coating that may comprise a plurality of localized surface plasmon resonance (LSPR) particles 3D-printed onto the core, wherein the shell coating is configured to be rupturable by laser irradiation with substantially a resonance wavelength of the LSPR particles, and wherein rupture of the shell coating releases the at least one of the target chemical, the molecule, or the one or more cells into the gel matrix such that the target chemical forms the chemical depot within the gel matrix.

5. The 3D-printed microenvironment of claim 1, further comprising the first type of live cells positioned within the 3D-printed microenvironment.

6. The 3D-printed microenvironment of claim 1, wherein the first type of live cells comprise at least one of cancer cells, immune system cells, or any cell with or without migratory properties.

7. The 3D-printed microenvironment of claim 1, wherein the second type of live cells line a conduit wall that defines the lumen of the conduit.

8. The 3D-printed microenvironment of claim 1, wherein the second type of cells comprise at least one of endothelial cells or other cell type that lines a tubular conduit in an organism.

9. The 3D-printed microenvironment of claim 1, wherein the plurality of the first type of live cells are positioned within the gel matrix.

10. The 3D-printed microenvironment of claim 1, wherein the plurality of the second type of live cells are positioned within the lumen of the conduit.

11. The 3D-printed microenvironment of claim 1, wherein the gel matrix comprises at least one of Fibrin or gelatin methacrylate.

12. The 3D-printed microenvironment of claim 1, wherein the target chemical comprises at least one of a signaling molecule, growth factor, a mediator, or DNA containing moiety.

13. The 3D-printed microenvironment of claim 1, further comprising a collection chamber at the outlet of the conduit and outside the gel matrix, wherein the collection chamber is configured to collect cells that migrated from the gel matrix, through the conduit, and into the lumen of the conduit.

14. The 3D-printed microenvironment of claim 1, wherein the one or more locations within the gel matrix at which the target chemical is disposed creates a chemical gradient in a direction with respect to the conduit.

15. A method of 3D-printing a 3D-printed microenvironment, the method comprising:
- 3D-printing a platform;
- 3D-printing a gel matrix scaffold on the platform, wherein the gel matrix comprises a chemical composition configured to culture a first type of live cells, and wherein the gel matrix and platform form one or more culture medium chambers configured to contain cell culture medium for the first type of live cells;
- introducing a conduit within the gel matrix defining a lumen comprising a second type of live cells, and defining an inlet from outside of the gel matrix to the lumen, wherein the conduit is configured to enable at least some of the first type of live cells to migrate through the conduit and facilitate flow of the at least: some of the live cells to an outlet of the conduit and enable introduction of at least one of other cells, chemical mediators, or drugs into the 3D-printed microenvironment via the inlet of the conduit, and wherein at least a portion of the gel matrix is disposed between the conduit and the one or more culture medium chambers; and
- sequentially introducing a target chemical to respective locations within the gel matrix, wherein the target chemical present at the respective locations creates at least one chemical gradient within the gel matrix.

16. The method of claim 15, wherein the first type of live cells are metastatic tumor cells.

17. The method of claim 15, wherein the second type of cells are endothelial cells.

18. The method of claim of 15, further comprising injecting a secondary chemical through the conduit.

19. The method of claim 15, further comprising collecting the cells that migrated through the conduit in a collection chamber at an outlet of the conduit.

20. The method of claim 15, further comprising 3D-printing a plurality of programmable-release capsules into the gel matrix, wherein 3D-printing each programmable-release capsule comprises:
- 3D-printing a core into the gel matrix, wherein the core comprises the target chemical; and
- 3D-printing a shell coating comprising a plurality of localized surface plasmon resonance (LSPR) particles 3D-printed onto the core, wherein the shell coating is configured to be rupturable by laser irradiation with substantially a resonance wavelength of the LSPR particles, and wherein rupture of the shell coating releases the target chemical into the gel matrix such that the target chemical forms a chemical depot within the gel matrix.

21. The method of claim 15, wherein sequentially introducing the target chemical comprises injecting the target chemical at the respective locations with at least one of an automated injection device, a 3D printer, or a pipette or a liquid dispenser.

22. The method of claim 15, further comprising positioning a plurality of a first type of live cells within the 3D-printed microenvironment.

23. The method of claim 22, further comprising positioning a model conduit defining a lumen and positioned within the gel matrix, wherein the model conduit comprises a plurality of a second type of live cells.

24. The method of claim 15, wherein the plurality of the first type of live cells are positioned within the gel matrix.

25. The method of claim 15, wherein the plurality of the first type of live cells are positioned within the lumen of the conduit.

26. The method of claim 15, wherein the 3D-printed microenvironment is a 3D-printed in vitro model biological microenvironment.

* * * * *